under 35 U.S.C. 154(b) by 351 days.

United States Patent
Nishino et al.

(10) Patent No.: US 8,767,919 B2
(45) Date of Patent: *Jul. 1, 2014

(54) RADIOGRAPHIC IMAGE CAPTURING SYSTEM AND RADIOGRAPHIC IMAGE CAPTURING METHOD

(75) Inventors: Naoyuki Nishino, Kanagawa-ken (JP); Yasunori Ohta, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 351 days.

This patent is subject to a terminal disclaimer.

(21) Appl. No.: 13/137,537

(22) Filed: Aug. 24, 2011

(65) Prior Publication Data

US 2012/0051522 A1   Mar. 1, 2012

(30) Foreign Application Priority Data

| Aug. 24, 2010 | (JP) | 2010-187303 |
| Aug. 24, 2010 | (JP) | 2010-187304 |
| Aug. 18, 2011 | (JP) | 2011-179096 |
| Aug. 18, 2011 | (JP) | 2011-179097 |

(51) Int. Cl.
    *H05G 1/44*   (2006.01)

(52) U.S. Cl.
    USPC .......................... 378/108; 378/62

(58) Field of Classification Search
    USPC .......................... 378/62, 92, 108
    See application file for complete search history.

(56) References Cited

U.S. PATENT DOCUMENTS

| 6,987,828 B2 * | 1/2006 | Horiuchi ........................ 378/16 |
| 7,768,002 B2 | 8/2010 | Kitamura et al. |
| 7,847,258 B2 | 12/2010 | Yaegashi et al. |
| 7,978,816 B2 * | 7/2011 | Matsuura et al. ............... 378/62 |
| 8,447,011 B2 * | 5/2013 | Ohta et al. ....................... 378/97 |
| 2009/0224162 A1 | 9/2009 | Inuiya et al. |

FOREIGN PATENT DOCUMENTS

| JP | 2000-105297 | 4/2000 |
| JP | 2007-103016 | 4/2007 |
| JP | 2009-032854 | 2/2009 |
| JP | 2009-212377 | 9/2009 |
| JP | 2009-212389 | 9/2009 |

OTHER PUBLICATIONS

National Institute of Advanced Industrial Science & Technology, "Development of Portable X-ray Sources Using Carbon Nanostructures" [online], Mar. 19, 2009, pp. 1-4.

* cited by examiner

*Primary Examiner* — Jurie Yun
(74) *Attorney, Agent, or Firm* — Edwards Neils PLLC; Jean C. Edwards, Esq.

(57) ABSTRACT

In a radiographic image-capturing system and radiographic image capturing method, a first image capturing process is performed, in which radiation is applied to a subject from at least one radiation source from among at least two radiation sources, whereby a first radiographic image is acquired. Based on the first radiographic image, respective doses of radiation to be emitted from the at least two radiation sources are weighted, and in accordance with such weighting, a second image capturing process is carried out, in which the respective radiation is applied to the subject from the at least two radiation sources.

11 Claims, 40 Drawing Sheets

FIG. 11

| REGION TO BE IMAGED (TECHNIQUE) | THICKNESS [mm] | RADIATION DOSE [mR] |
|---|---|---|
| CHEST (CAPTURING IMAGE OF FRONTAL CHEST) | ▽▽ | ◇◇ |
| HAND (CAPTURING IMAGE OF BACK OF HAND) | ▽▽▽ | ◇◇◇ |
| ... | ... | ... |

FIG. 12

| REGION TO BE IMAGED (TECHNIQUE) | NUMBER OF RADIATION SOURCES | WEIGHTING OF RADIATION DOSE ||||
|---|---|---|---|---|---|
| | | A | B | C | ... |
| CHEST (CAPTURING IMAGE OF FRONTAL CHEST) | 2 | ○○ | △△ | — | ... |
| | 3 | □□ | ×× | □□ | ... |
| | ... | ... | ... | ... | ... |
| HAND (CAPTURING IMAGE OF BACK OF HAND) | 2 | ○○ | △△ | — | ... |
| | 3 | □□ | ×× | □□ | ... |
| | ... | ... | ... | ... | ... |
| ... | | | | | |

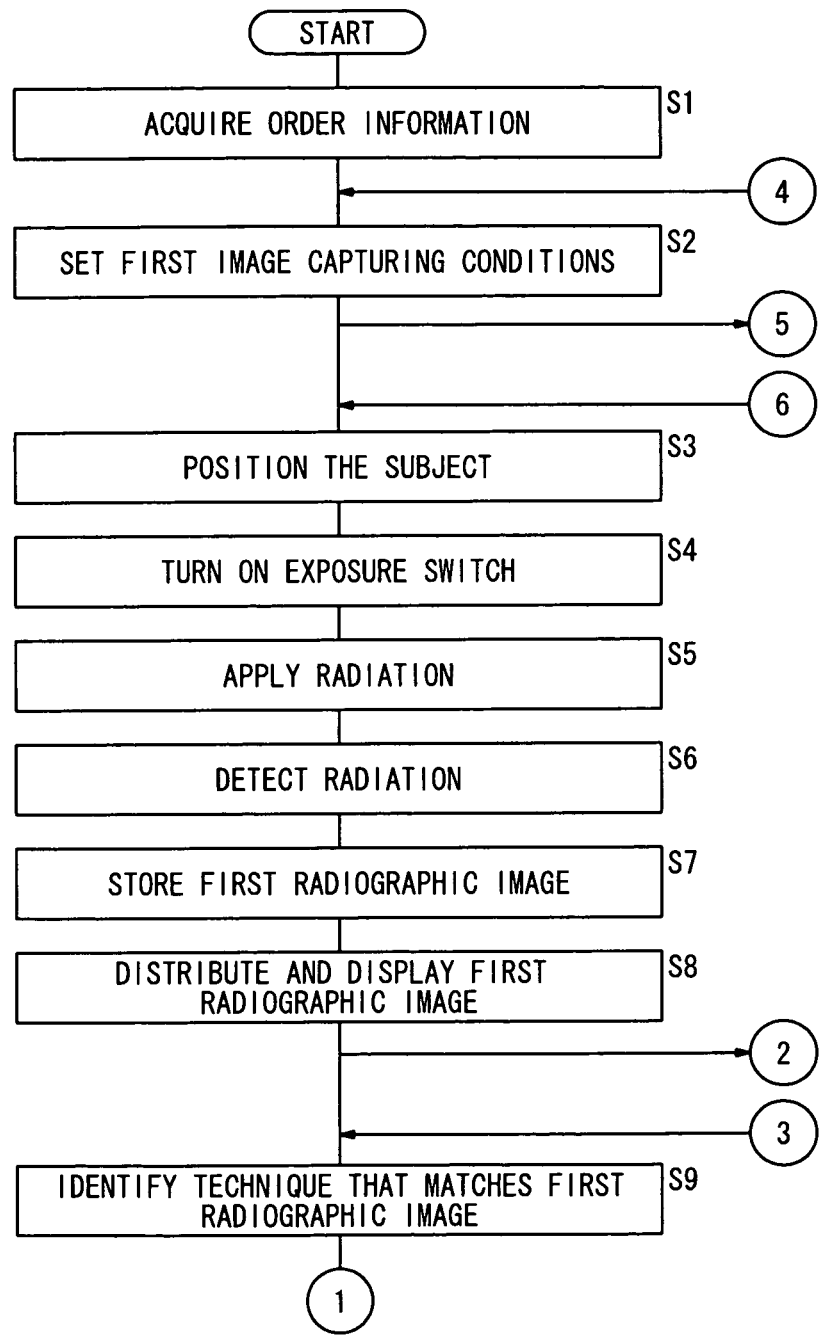

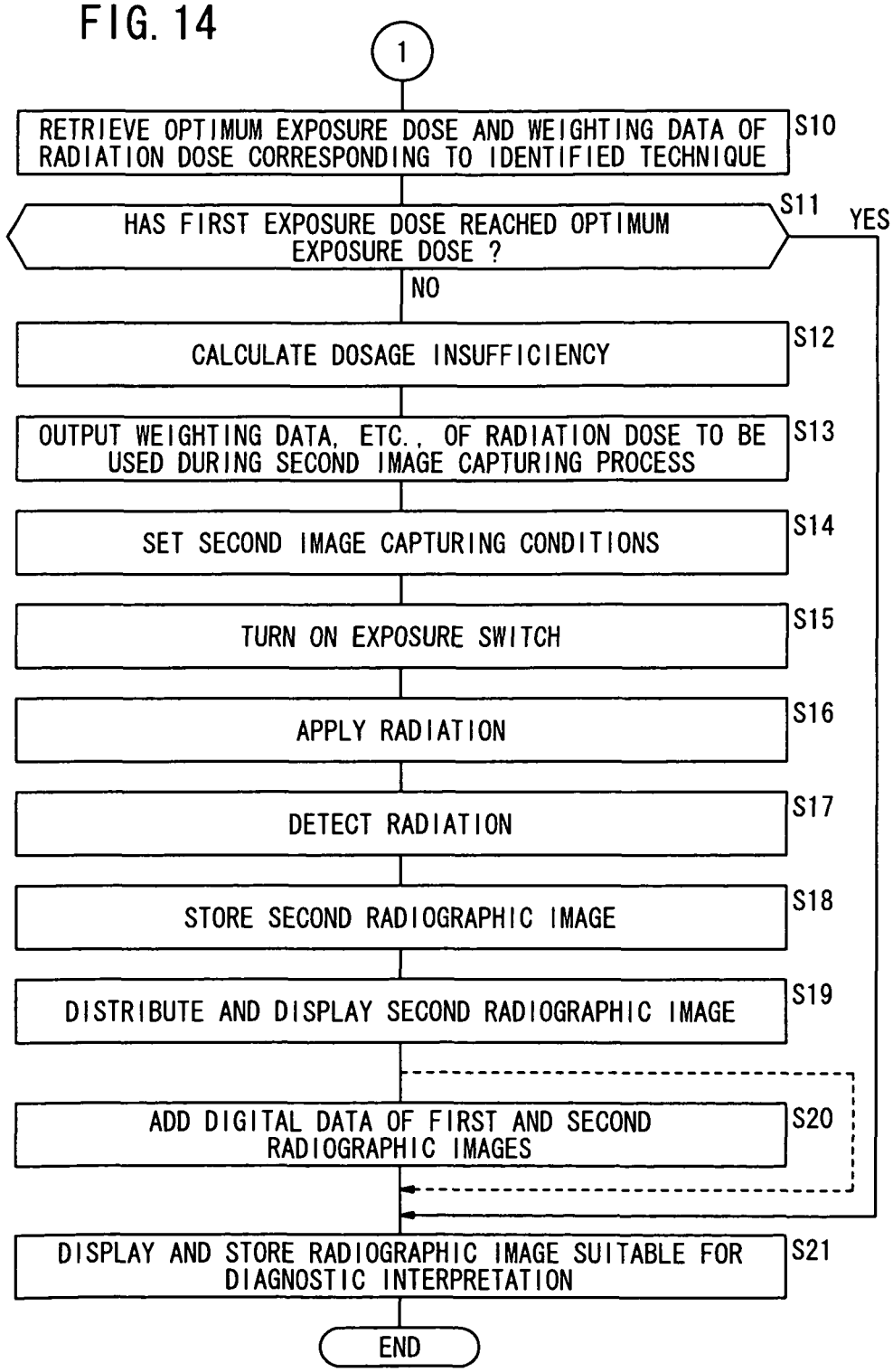

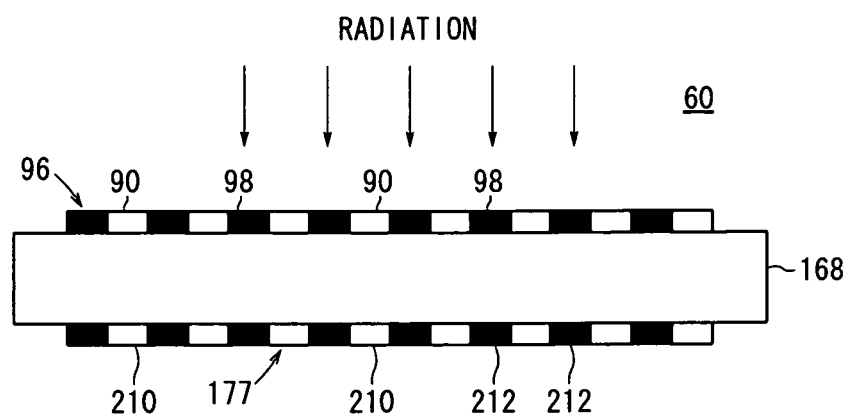

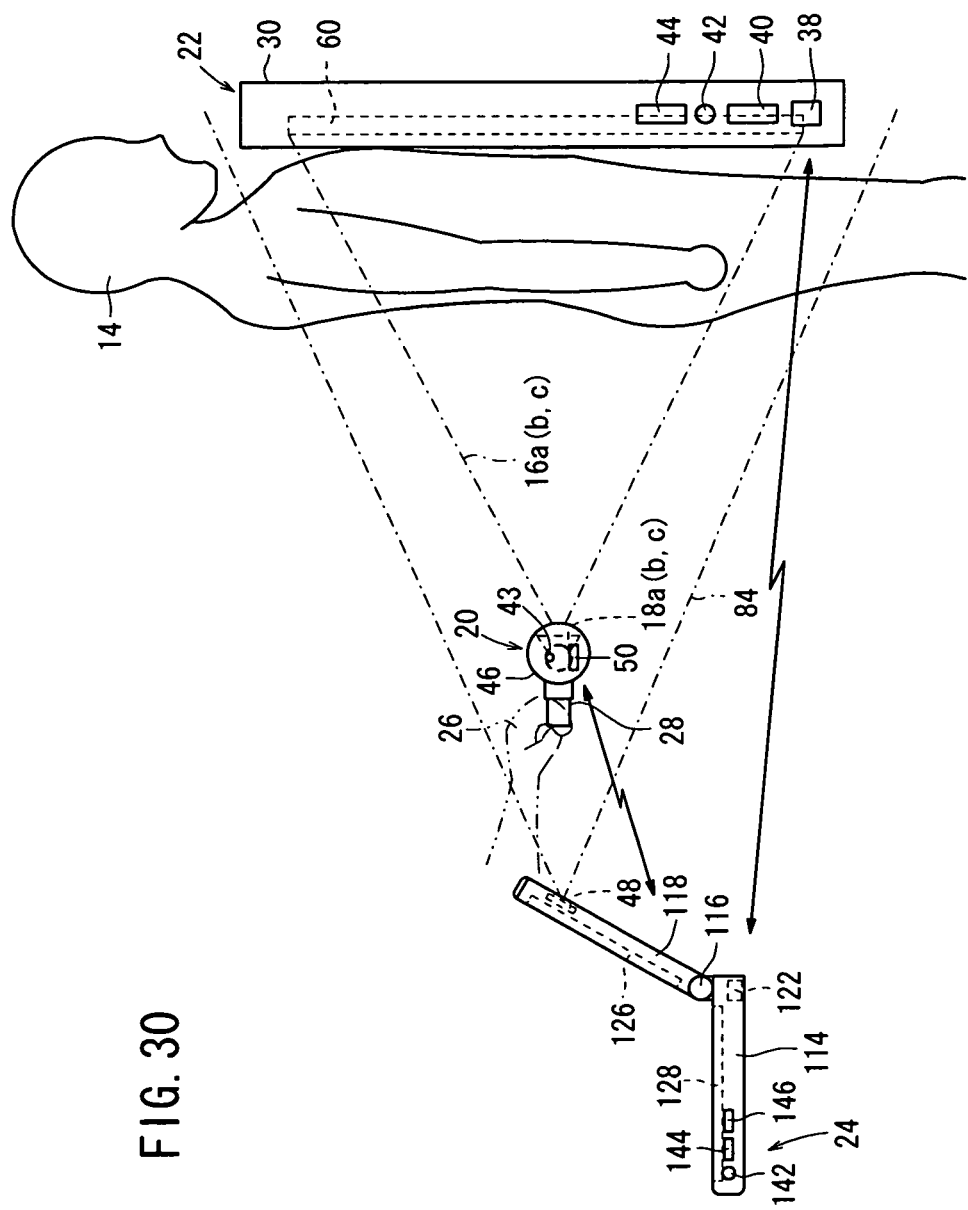

RADIOGRAPHIC IMAGE CAPTURING SYSTEM AND RADIOGRAPHIC IMAGE CAPTURING METHOD

CROSS-REFERENCE TO RELATED APPLICATION

This application is based upon and claims the benefit of priority from Japanese Patent Applications No. 2010-187303 filed on Aug. 24, 2010, No. 2010-187304 filed on Aug. 24, 2010, No. 2011-179096 filed on Aug. 18, 2011 and No. 2011-179097 filed on Aug. 18, 2011, of which the contents are incorporated herein by reference.

BACKGROUND OF THE INVENTION

1. Field of the Invention

The present invention relates to a radiographic image capturing system and a radiographic image capturing method for applying radiation from a plurality of radiation sources housed in a radiation output device to a subject, detecting radiation that has passed through the subject with a radiation detecting device, and converting the detected radiation into radiographic images.

2. Description of the Related Art

In the medical field, there have widely been used radiographic image capturing systems, which apply radiation from a radiation source to a subject and detect the radiation that has passed through the subject with a radiation detecting device in order to acquire a radiographic image of the subject. Radiographic image capturing systems that are installed in hospitals (medical organizations), for example, usually employ a thermionic emission radiation source, which is relatively large and heavy.

If such a radiographic image capturing system is directly used to capture radiographic images within hospitals while making rounds, or outside of hospitals, e.g., in medical checkup cars, at sites suffering from natural disasters, or at sites receiving home care services, then a large and heavy radiation source needs to be carried to such sites for capturing radiographic images. The process of carrying the radiation source to the site and setting up the radiation source at the site is quite burdensome for the doctor or radiological technician in charge. To solve this problem, Japanese Laid-Open Patent Publication No. 2007-103016 discloses a field-emission radiation source, which is smaller and lighter than a thermionic emission radiation source.

SUMMARY OF THE INVENTION

If a field-emission radiation source is operated at a site, it is highly likely that difficulties will be experienced in preparing an appropriate external power supply. Therefore, the field-emission radiation source should preferably be of a battery-powered design. However, a battery-powered field-emission radiation source, although it is small and lightweight, emits a small dose of radiation. It is customary for the doctor or radiological technician to keep the field-emission radiation source as closely to the subject as possible while capturing a radiographic image of the subject at a site, in order to reduce the source-to-image distance (SID) between the field-emission radiation source and the radiation detecting device. As a result, radiation emitted from the field-emission radiation source has a small irradiation range. Because of the small irradiation range, and also due to the small dose (exposure dose) of radiation applied to the subject, the field-emission radiation source may fail to capture a radiation image based on an exposure dose that is sufficiently large for a doctor to read radiation images correctly.

One solution is to install a plurality of field-emission radiation sources and to emit radiation from such field-emission radiation sources toward a subject in order to cover a desired irradiation range (a region to be imaged of the subject). According to another solution, while a single field-emission radiation source is being moved over the subject, radiation is emitted toward the subject from the field-emission radiation source, which has been moved to different positions in order to cover a desired irradiation range.

As long as a subject is irradiated with an optimum dose (exposure dose) of radiation depending on the subject, a radiographic image of the subject can be captured based on an exposure dose that is large enough for a doctor to read the resultant radiation image correctly, and the subject remains free of undue radiation exposure.

However, as noted above, if a field-emission radiation source simply applies radiation to a subject in order to cover a desired irradiation range, the subject may not necessarily be irradiated with an optimum dose of radiation.

An object of the present invention is to provide a radiographic image capturing system and a radiographic image capturing method, which are capable of easily increasing an irradiation range of radiation, and of applying an optimum dose of radiation to a subject, in the case that a radiographic image of the subject is captured using a field-emission radiation source at a short SID.

To accomplish the above object, in accordance with the present invention, there is provided a radiographic image capturing system comprising a radiation output device housing therein at least two radiation sources capable of emitting radiation with respect to a subject, a radiation detecting device for detecting radiation that has passed through the subject and converting the detected radiation into a radiographic image, and a control device for controlling the radiation output device and the radiation detecting device, wherein:

in a case that a first image capturing process is carried out, in which radiation is applied to the subject from at least one radiation source from among the at least two radiation sources, the radiation detecting device detects radiation that has passed through the subject, thereby acquiring a first radiographic image by the first image capturing process; and the control device carries out weighting on doses of radiation to be emitted from the at least two radiation sources based on the first radiographic image, and controls the radiation output device to carry out a second image capturing process, in which the respective radiation is applied to the subject from the at least two radiation sources, in accordance with the weighting.

According to the present invention, there also is provided a radiographic image capturing method comprising the steps of:

in a case that at least two radiation sources are housed in a radiation output device, performing a first image capturing process, in which radiation is applied to the subject from at least one radiation source from among the at least two radiation sources;

acquiring a first radiographic image by the first image capturing process, by detecting, with a radiation detecting device, radiation that has passed through the subject;

carrying out weighting on respective doses of radiation to be emitted from the at least two radiation sources based on the first radiographic image;

in accordance with the weighting, carrying out a second image capturing process, in which the respective radiation is applied to the subject from the at least two radiation sources; and acquiring a second radiographic image by the second image capturing process, by detecting, with the radiation detecting device, the respective radiation that has passed through the subject.

According to the present invention, radiation is applied (in the first image capturing process) to the subject from at least one radiation source from among the at least two radiation sources housed in the radiation output device, and based on the radiographic image obtained by the first image capturing process, respective doses of radiation emitted from the at least two radiation sources are weighted in the second image capturing process.

Accordingly, even if a second image capturing process is carried out with respect to the subject, the cumulative exposure dose to the subject by the first and second image capturing processes is made optimum. Stated otherwise, according to the present invention, the subject is not exposed to radiation unnecessarily.

In the foregoing manner, according to the present invention, an irradiation range of the radiation is not set simply by enabling a desired irradiation range (region to be imaged of the subject) to be covered, but rather, based on the first radiographic image, radiation doses of the respective radiation emitted from the respective radiation sources are weighted during the second image capturing process.

Accordingly, with the present invention, even if image capturing (the first and second image capturing processes) of a radiographic image is carried out with respect to the subject at a short SID using field-emission radiation sources, the irradiation range of the radiation can easily be enlarged, and radiation can be applied at an optimum radiation dose (exposure dose) with respect to the subject.

In the present invention, in a case that the radiation output device and the radiation detecting device face each other, the radiation output device houses therein the at least two radiation sources arranged in a linear array, or at least three radiation sources arranged in a two-dimensional matrix with respect to an irradiated surface of the radiation detecting device that is irradiated with radiation. In this case, capturing of radiographic images can be carried out effectively with respect to any type of region to be imaged.

Further, the present invention (the first invention and the second invention thereof) can be constituted in the following manner.

In the first invention, the control device carries out weighting on the doses of radiation to be emitted from the at least two radiation sources so as to supplement an insufficiency in the doses of radiation, in a case that the dose of radiation by the first image capturing process shown in the first radiographic image does not reach an optimum dose with respect to the subject.

In this case, if the dose of radiation (exposure dose) with respect to the subject shown in the radiographic image obtained by the first image capturing process does not reach the optimum radiation dose, the respective radiation doses of radiation emitted from the at least two radiation sources during the second image capturing process are weighted, in order to supplement any difference (insufficiency of the radiation dose) between the optimum radiation dose and the dose applied during the first image capturing process.

Accordingly, even if image capturing is carried out a second time with respect to the subject, the cumulative exposure dose with respect to the subject by the initial image capturing process and the retaken image capturing process (i.e., the first and second image capturing processes) is made to correspond with the optimum radiation dose.

More specifically, with the first invention, even in the event that image capturing is performed again with respect to the subject (in the second image capturing process) due to the fact that a desired radiographic image was not obtained by the first image capturing process, the subject is not exposed to radiation unnecessarily. Further, using the first radiographic image and the second radiographic image obtained from the second image capturing process, assuming desired image processing (e.g., an addition process) is performed, a radiographic image based on an exposure dosage suitable for diagnostic interpretation by a doctor can easily be obtained.

In the first invention, if the dose of radiation with respect to the subject shown in the first radiographic image has reached the optimum radiation dose, since a radiographic image based on an exposure dosage suitable for diagnostic interpretation by a doctor is already obtained thereby, naturally, the second image capturing process (recapturing) is rendered unnecessary.

On the other hand, in the second invention, the first image capturing process is a pre-exposure process for applying radiation to the subject from at least one of the at least two radiation sources, the radiographic image of the first image capturing process is a pre-exposure image which is a radiographic image formed by the pre-exposure process, the second radiographic image capturing process is a main exposure process for applying radiation respectively to the subject from the at least two radiation sources in accordance with the weighting. In this case, the control device controls the radiation output device to perform the main exposure process, and together therewith, controls the radiation detection device to detect the respective radiation that has passed through the subject and acquire a main exposure image, which is a radiographic image formed by the main exposure process.

According to the second invention, a pre-exposure process is carried out with respect to the subject from at least one of the at least two radiation sources, and based on the pre-exposure image obtained by the pre-exposure process, respective radiation doses output from the at least two radiation sources are weighted during the main exposure process.

In the foregoing manner, according to the second invention, an irradiation range of the radiation is not set simply by enabling a desired irradiation range (region to be imaged of the subject) to be covered, but rather, based on the pre-exposure image obtained by the pre-exposure process, which is carried out before the main exposure process, respective doses of radiation emitted from the respective radiation sources are weighted during the main exposure process. In addition, because the region to be imaged of the subject is reflected in the pre-exposure image, weighting of the respective doses of radiation is carried out depending on the region to be imaged.

Accordingly, with the second invention, even if image capturing of a radiographic image (the aforementioned main exposure process) is carried out with respect to the subject at a short SID using field-emission radiation sources, the irradiation range of the radiation can easily be enlarged, and radiation can be applied at an optimum radiation dose (exposure dose) with respect to the subject. In this manner, with the second invention, because radiation is applied to the subject at an optimum dose corresponding to the subject, a radiographic image (main exposure image) suitable for diagnostic interpretation by a doctor can be obtained, and unnecessary exposure of the subject to radiation can be avoided.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 11 is a diagram showing, by way of example, a table that is stored in the database shown in FIG. 8;

FIG. 12 is a diagram showing, by way of example, a table that is stored in the database shown in FIG. 8;

FIG. 13 is a flowchart of an operation sequence of the radiographic image capturing system according to the first embodiment;

FIG. 14 is a flowchart of an operation sequence of the radiographic image capturing system according to the first embodiment;

FIG. 22 is a side elevational view showing in outline a radiographic image capturing system according to a seventh modification;

FIG. 30 is a side elevational view showing a radiographic image capturing system according to an eleventh modification;

DESCRIPTION OF THE PREFERRED EMBODIMENTS

A radiographic image capturing system according to preferred embodiments of the present invention, in relation to a radiographic image capturing method, will be described in detail below with reference to FIGS. 1 through 40B.

Figure 1:
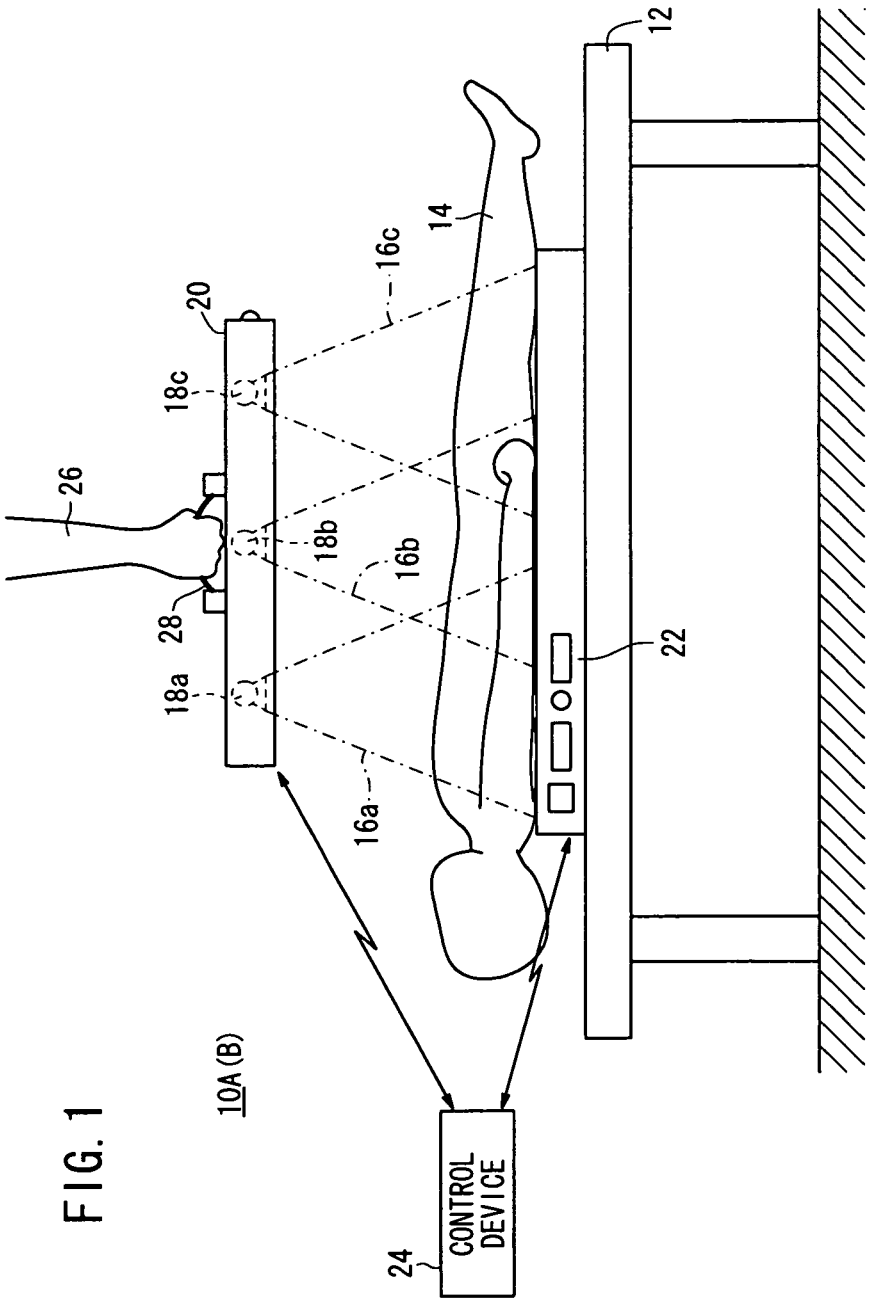
FIG. 1 is a schematic view of a radiographic image capturing system according to first and second embodiments of the present invention.

As shown in FIG. 1, a radiographic image capturing system 10A according to a first embodiment of the present invention includes a radiation output device 20 housing therein a plurality of radiation sources 18a through 18c, which are capable of applying radiation 16a through 16c to a subject 14 lying on an image capturing table 12 such as a bed or the like, a radiation detecting device 22 for detecting radiation (one source of radiation from among the radiation 16a through 16c) that has passed through the subject 14 and converting the detected radiation into radiographic images (a first radiographic image and a second radiographic image), and a control device 24 for controlling the radiation output device 20 and the radiation detecting device 22. The control device 24, the radiation output device 20, and the radiation detecting device 22 may send signals to each other and receive signals from each other by way of a wireless LAN according to standards such as UWB (Ultra-Wide Band), IEEE802.11.a/g/n. or the like, wireless communications using millimeter waves, or by wired communications using cables.

The radiographic image capturing system 10A may be applied in order to capture radiographic images of the subject 14 (patient) in an image capturing chamber of a radiological department of a hospital (medical organization), to capture radiographic images of the subject 14 (patient) in a patient's bedroom in a hospital at the time that the doctor 26 makes rounds, or to capture radiographic images of the subject 14 outside of the hospital. Capturing of radiographic images of the subject 14 outside of the hospital refers to capturing of radiographic images of the subject 14 (examinee) at the time that a medical checkup is carried out using a medical checkup car, capturing of radiographic images of the subject 14 (injured party) at a disaster site such as a natural disaster site, or capturing of radiographic images of the subject 14 (resident) at a home medical care site.

To realize such applications, each of the radiation sources 18a through 18c of the radiographic image capturing system 10A according to the first embodiment should preferably be a field-emission radiation source, as disclosed in Japanese Laid-Open Patent Publication No. 2007-103016. Further, the radiation output device 20, which houses therein the radiation sources 18a through 18c, has a grip 28 to be gripped by the doctor or radiological technician in charge (hereinafter simply referred to as "doctor"), on a side thereof remote from the side on which radiation 16a through 16c is emitted from the radiation sources 18a through 18c. Therefore, the radiation output device 20 comprises a portable device.

The radiation detecting device 22 comprises a portable electronic cassette incorporating either a radiation detector of an indirect conversion type including a scintillator for temporarily converting radiation that has passed through the subject 14 into visible light, or a solid-state detector (hereinafter also referred to as "pixels"), which is made of a substance such as amorphous silicon (a-Si) or the like, for converting visible light into electric signals. Alternatively, the radiation detecting device 22 comprises a radiation detector of a direct conversion type including a solid-state detector, which is made of a substance such as amorphous selenium (a-Se) or the like, for directly converting radiation that has passed through the subject 14 into electric signals.

The control device 24 should preferably be a portable information terminal such as a laptop personal computer (PC), a tablet PC, or a personal digital assistant (PDA), for example. If the radiographic image capturing system 10A is used in an image capturing chamber of the radiological department of a hospital, then the control device 24 may comprise a stationary console, while the radiation output device 20 and the radiation detecting device 22 may be portable devices.

Figure 2A:
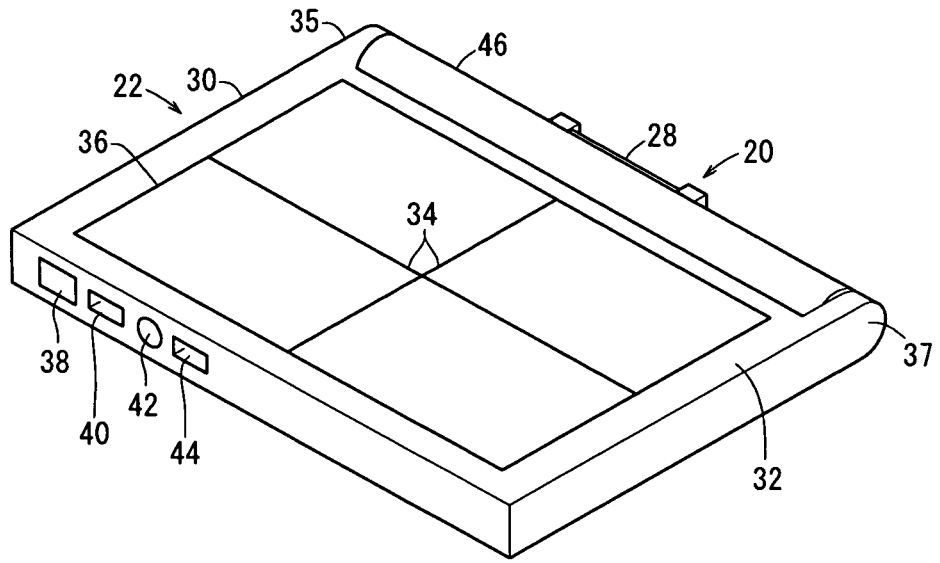
FIG. 2A is a perspective view of a radiation output device and a radiation detecting device shown in FIG. 1, which are integrally combined with each other.
Figure 2B:
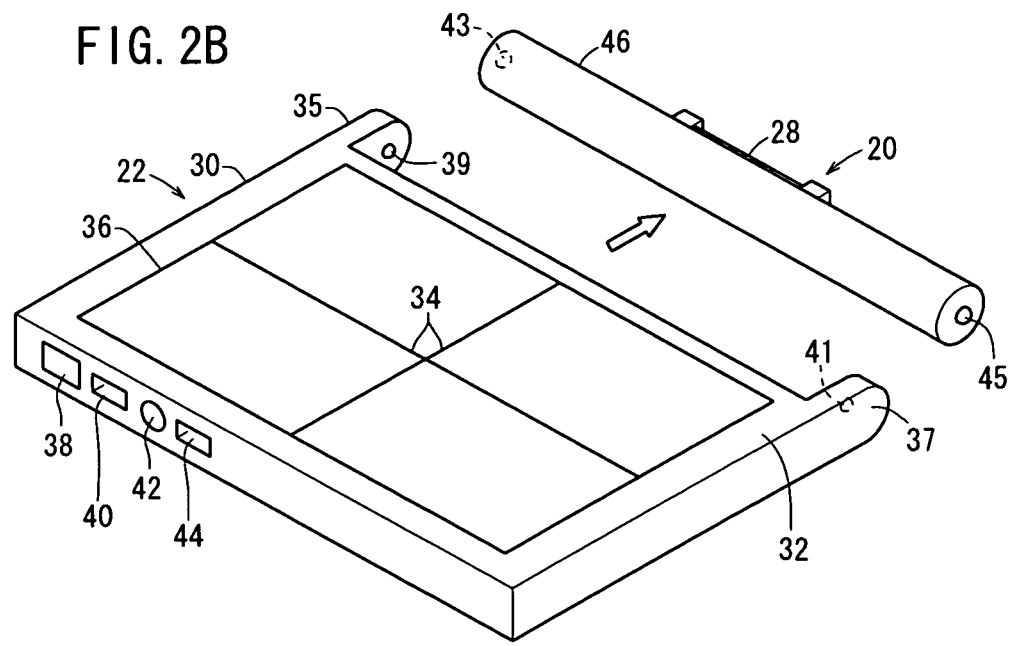
FIG. 2B is a perspective view of the radiation output device and the radiation detecting device, in a state of being separated from each other.

As shown in FIGS. 2A and 2B, the radiation detecting device 22 includes a rectangular housing 30 made of a material permeable to radiation 16a through 16c (see FIG. 1) and having a surface (upper surface) for positioning the subject 14 thereon, the surface serving as an irradiated surface 32, which is irradiated with radiation 16a through 16c. The irradiated surface 32 has guide lines 34 serving as a reference for an image capturing area and an image capturing position for the radiation 16a through 16c. The guide lines 34 provide an outer frame defining an imaging area 36, which can be irradiated with radiation 16a through 16c. One side of the housing 30 has a switch 38 for turning on and off the radiation detecting device 22, a card slot 40 for receiving a memory card (not shown) therein, an input terminal 42 for connection to an AC adapter, and a USB terminal 44 for connection to a USB cable (not shown).

The radiation detecting device 22 also includes holders 35, 37 that project outwardly from a side of the housing 30 remote from the side having the switch 38, the card slot 40, the input terminal 42, and the USB terminal 44. The holder 35 has a convex connection terminal 39 facing the holder 37, whereas the holder 37 has a concave connection terminal 41 facing the holder 35 (see FIGS. 2B to 3B). The aforementioned radiation output device 20 has a hollow cylindrical casing 46 including a concave connection terminal 43 on an end thereof for receiving therein the convex connection terminal 39 of the holder 35, and a convex connection terminal 45 on the other end thereof for being fitted into the concave connection terminal 41 of the holder 37 (see FIGS. 2B, 4A and 4B).

By interfitting engagement of the connection terminals 39, 43 and the connection terminals 41, 45, as shown in FIG. 2A, the radiation output device 20 is held between the holders 35, 37, and the connection terminals 39, 43 and the connection terminals 41, 45 are electrically connected to each other. In this manner, once the radiation output device 20 and the radiation detecting device 22 are integrally combined with each other, the doctor 26 can grip the grip 28, for example, and carry the radiation output device 20 and the radiation detecting device 22. Further, while the radiation output device 20 and the radiation detecting device 22 are integrally combined with each other, a location on the radiation output device 20 where radiation 16a through 16c is emitted faces toward a side surface of the housing 30 of the radiation detecting device 22.

On the other hand, by releasing the held state of the radiation detecting device 22 by the holders 35, 37 and the connection terminals 39, 41, 43, 45, and separating the radiation detecting device 22 from the radiation output device 20, the radiation output device 20 and the radiation detecting device 22 are no longer integrally combined with each other, and the connection terminals 39, 43 and the connection terminals 41, 45 are electrically disconnected from each other, respectively.

Figure 3B:
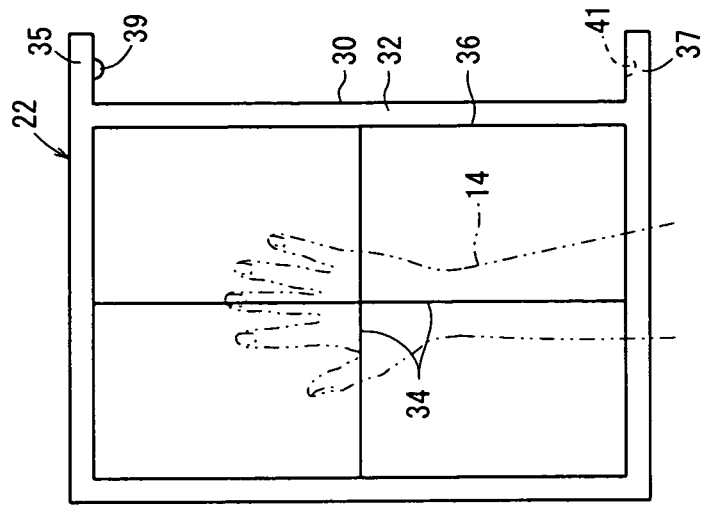
FIGS. 3A and 3B are plan views showing how regions to be imaged of a subject are positioned with respect to the radiation detecting device.
Figure 3A:
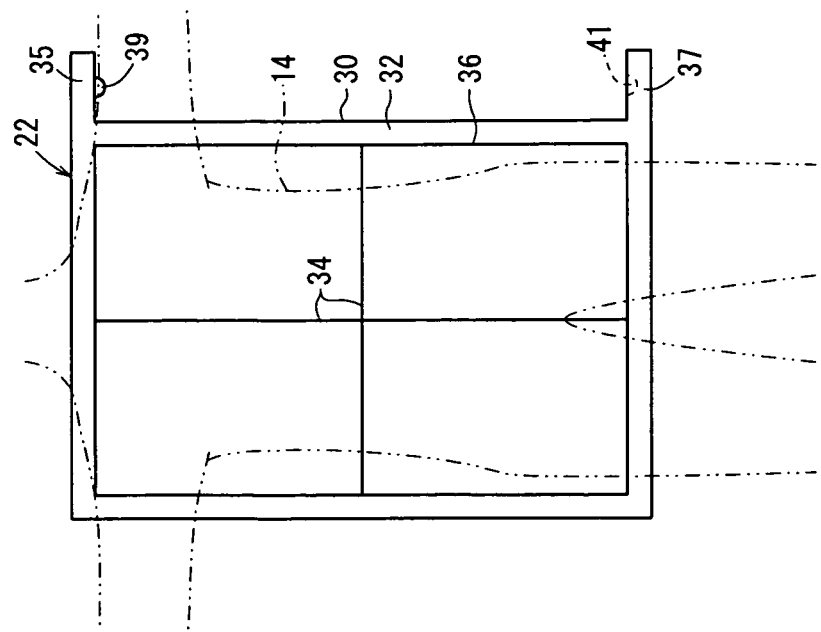

As shown in FIGS. 3A and 3B, for positioning the subject 14, as viewed in plan, a region to be imaged of the subject 14 is positioned such that a central position of the region to be imaged of the subject 14 and a central position (i.e., a point of intersection of the guide lines 34) of the imaging area 36 are kept in substantial alignment with each other, and the region to be imaged of the subject 14 falls within the imaging area 36. FIG. 3A shows the chest of the subject 14, which is positioned as a region to be imaged. FIG. 3B shows a right hand of the subject 14, which is positioned as a region to be imaged.

Figure 4A:
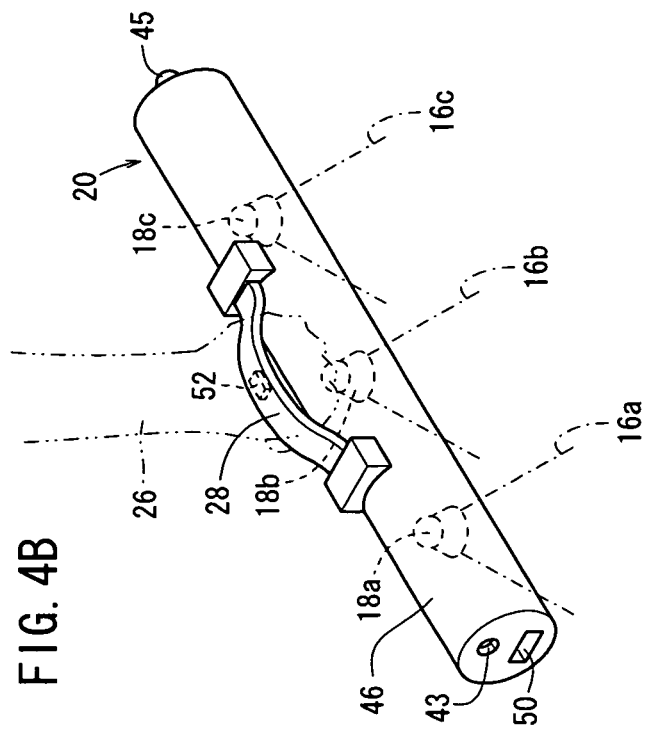
FIGS. 4A and 4B are perspective views of the radiation output device.
Figure 4B:
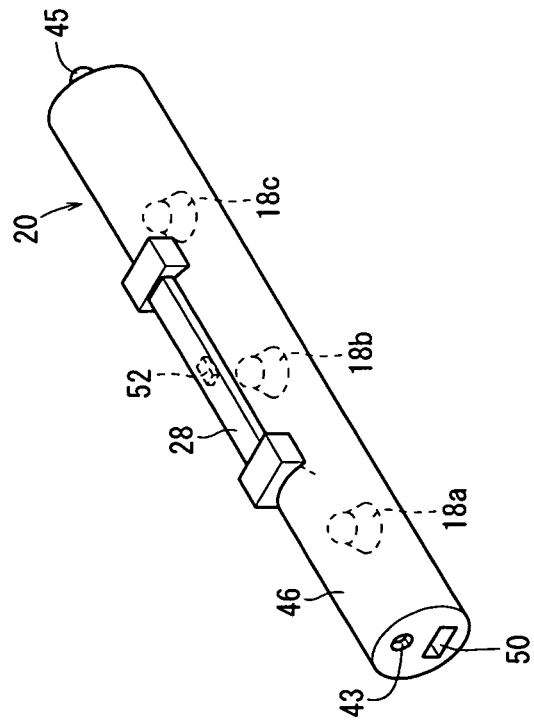

As shown in FIGS. 4A and 4B, the radiation output device 20 includes the hollow cylindrical casing 46, which is made of a material permeable to radiation 16a through 16c. Three field-emission radiation sources 18a through 18c are arranged along one direction, i.e., arranged as a linear array, in the casing 46. A USB terminal 50 for connection to a USB cable (not shown) and the connection terminal 43 are disposed on one end of the casing 46, whereas the connection terminal 45 is disposed on the other end of the casing 46. The aforementioned grip 28 is disposed on a side surface of the casing 46, and incorporates therein a touch sensor (gripped state sensor) 52.

The touch sensor 52 comprises an electrostatic capacitance sensor or a resistance-film contact sensor. In a case where the doctor 26 grips the grip 28 and contacts electrodes (not shown) of the touch sensor 52 with the hand, the touch sensor 52 outputs a detection signal indicating that the hand and the electrodes are held in contact with each other. The touch sensor 52 may alternatively be a mechanical switch such as a push switch or the like. If the touch sensor 52 is a mechanical switch, then in a case where the doctor 26 grips the grip 28 and contacts the mechanical switch, the touch sensor 52 outputs a detection signal indicating that the mechanical switch has been turned on or off.

In a case where the doctor 26 grips the grip 28 and orients the radiation output device 20 toward the subject 14, the radiation output device 20, in response to output of the detection signal from the touch sensor 52, enables radiation 16a through 16c to be emitted from at least one of the radiation sources 18a through 18c (see FIG. 4B). Further, in the case that emission of radiation 16a through 16c from the respective radiation sources 18a through 18c is enabled, the radiation output device 20 can emit radiation 16a through 16c simultaneously or sequentially from the radiation sources 18a through 18c. While the radiation output device 20 and the radiation detecting device 22 are integrally combined with each other by the holders 35, 37 and the connection terminals 39, 41, 43, 45, the radiation output device 20 does not permit the radiation sources 18a through 18c to emit radiation, i.e., the radiation sources 18a through 18c are prohibited from emitting radiation 16a through 16c, even if the doctor 26 grips the grip 28.

Figure 5A:
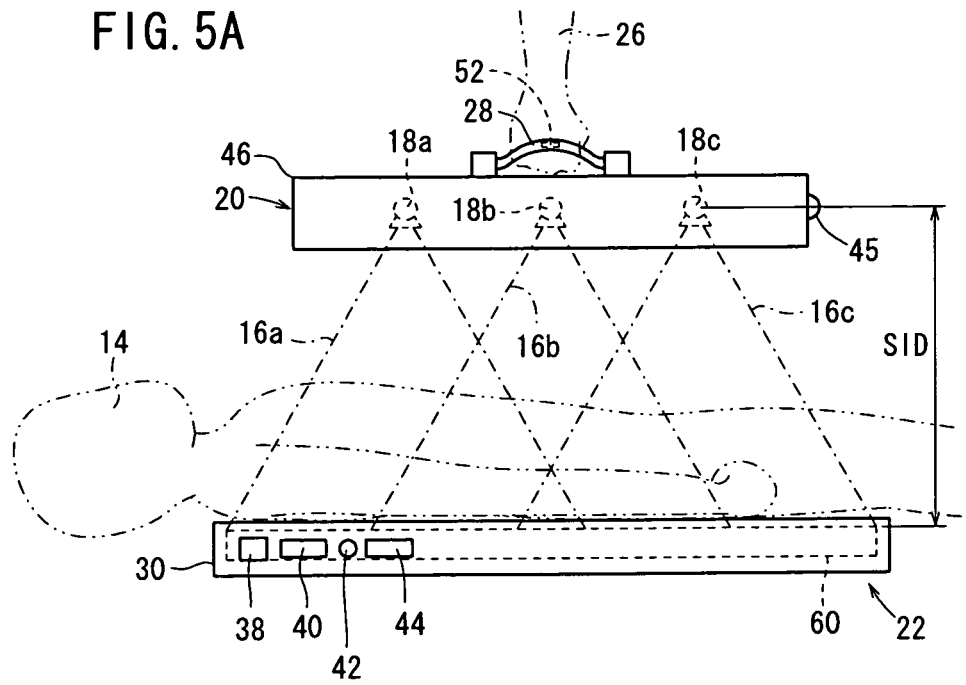
FIGS. 5A and 5B are side elevational views showing the manner in which a region to be imaged of the subject is irradiated.
Figure 5B:
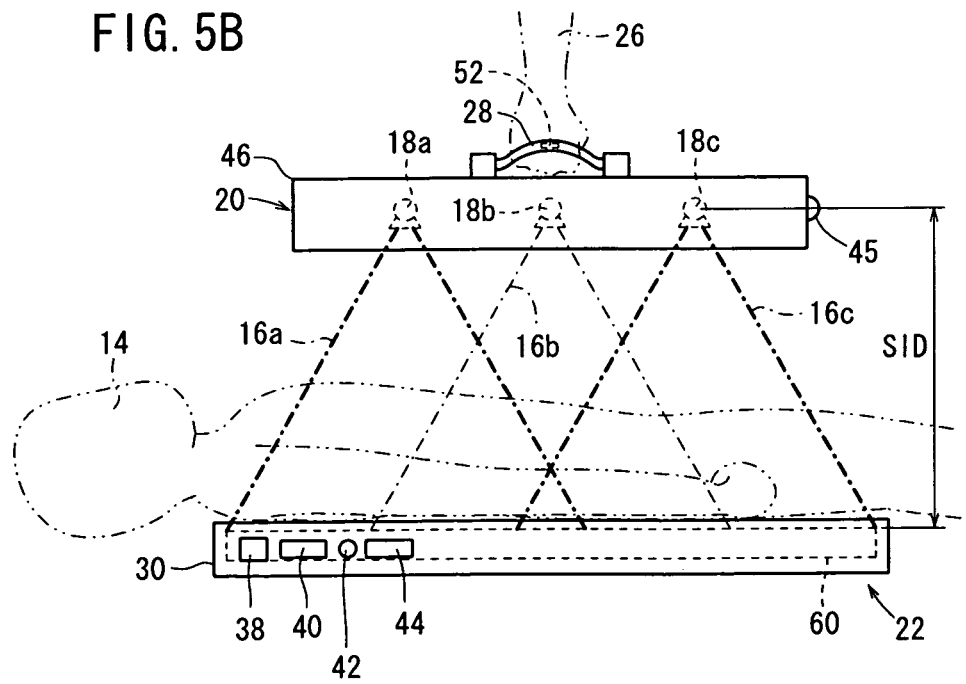
Figure 6A:
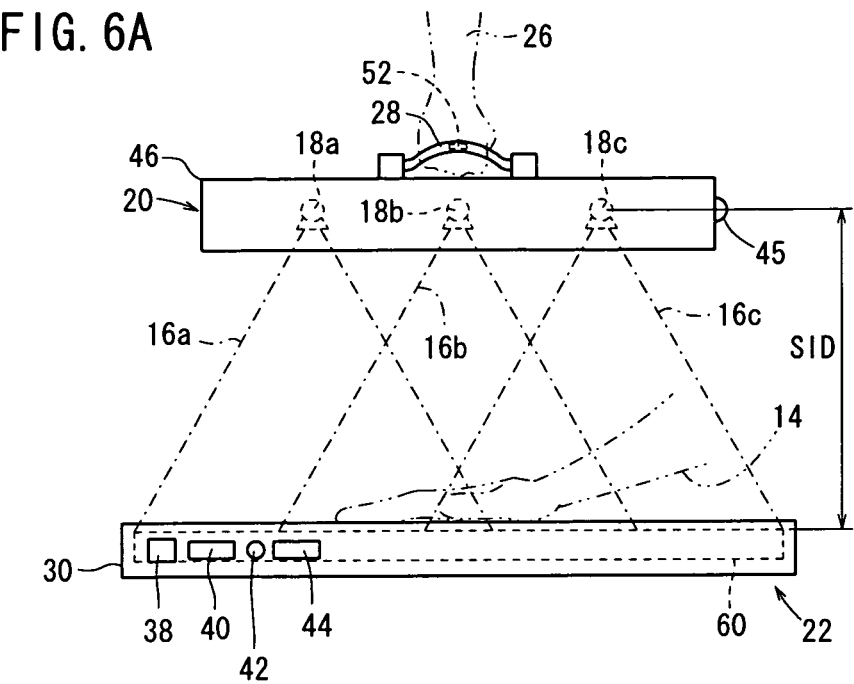
FIGS. 6A and 6B are side elevational views showing the manner in which a region to be imaged of the subject is irradiated.
Figure 6B:
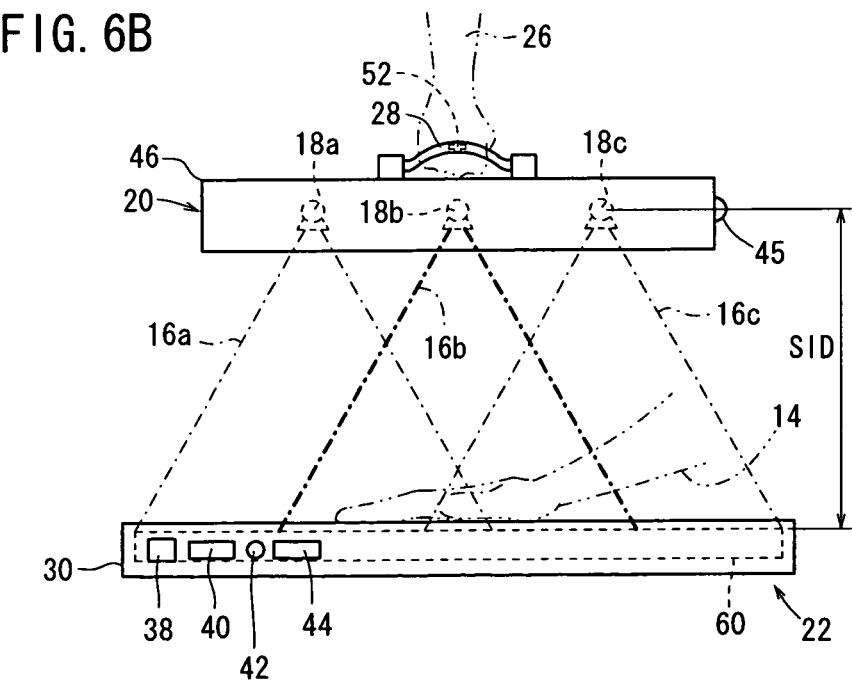

FIGS. 5A and 5B show the manner in which an image of the chest of the subject 14, which is a relatively large region to be imaged, is captured, whereas FIGS. 6A and 6B show the manner in which an image of a hand of the subject 14, which is a relatively small region to be imaged, is captured. In this case, the three radiation sources 18a through 18c are arranged in the casing 46 of the radiation output device 20 along a horizontal direction of FIGS. 5A through 6B, i.e., along the longitudinal direction of the casing 46. Further, in a case where radiation 16a through 16c is applied from at least one of the radiation sources 18a through 18c to the region to be imaged of the subject 14, such radiation 16a through 16c passes through the region to be imaged and then through the surface (the imaging area 36 in FIGS. 2 through 3B) of the housing 30 of the radiation detecting device 22, and the radiation is led to a radiation detector 60 housed in the interior of the housing 30. The radiation detector 60, which is either a radiation detector of an indirect conversion type or a radiation detector of a direct conversion type, detects radiation 16a through 16c and converts the radiation 16a through 16c into a radiographic image.

Incidentally, if the portable radiation output device 20 is operated in a hospital or at a site outside of a hospital, then since difficulty may be experienced in securing an appropriate external power supply, each of the radiation sources 18a through 18c of the radiation output device 20 should preferably be a battery-powered radiation source. Consequently, the field-emission radiation sources 18a through 18c should be small and lightweight radiation sources, for emitting a smaller dose of radiation than is possible with a thermionic emission radiation source, which typically is used in an image capturing chamber of the radiological department of the hospital.

In this case, at the site where the radiographic image capturing system is used, the doctor 26 is required to keep the radiation output device 20 as close to the subject 14 as possible, thereby reducing the source-to-image distance (SID) between the radiation sources 18a through 18c and the radiation detector 60 in the radiation detecting device 22, for capturing radiographic images of the subject 14. As a result, radiation 16a through 16c emitted from the respective radiation sources 18a through 18c is applied within a narrow irradiation range, and the doses (exposure doses) of radiation 16a through 16c applied to the subject 14 are small. Therefore, the radiographic image capturing system 10A may fail to capture radiation images based on an exposure dose, which is large enough to enable the doctor 26 to read radiation images correctly.

More specifically, in the case that a first image capturing process is performed with respect to a region to be imaged of the subject 14, because the radiation dose of the radiation 16a through 16c with respect to the region to be imaged is small, if one wishes to obtain a radiographic image of an exposure dose sufficient to enable diagnostic interpretation of the image, it is necessary to retake the images, i.e., to perform a second image capturing process. However, if the second image capturing process is carried out, in which radiation 16a through 16c of a large radiation dose is applied to the region to be imaged, then cases could occur in which the cumulative exposure dose of the second image capturing process (the first image capturing process and the second image capturing process) exceeds the exposure dose suitable for image diagnosis, and the subject 14 is exposed to radiation unnecessarily.

On the other hand, in the case that the subject 14 is irradiated with an optimum dose (exposure dose) of radiation depending on the region to be imaged of the subject 14 and the thickness of the region to be imaged, a radiographic image can be obtained based on an exposure dose, which is suitable to enable the doctor 26 to diagnostically interpret the resultant radiation image correctly, and together therewith, the subject 14 can avoid undue exposure to radiation.

With the first embodiment, at least two radiation sources (three radiation sources 18a through 18c as shown in FIGS. 4A to 6B) are disposed in the radiation output device 20.

Additionally, in the case that a radiographic image is to be captured of the subject 14, initially, the first radiographic image capturing process is performed, for applying radiation (radiation 16a through 16c shown in FIGS. 5A and 6A) of a predetermined dose to the subject 14 from at least one of the radiation sources (the radiation sources 18a through 18c shown in FIGS. 5A and 6A) among the at least two radiation sources. At least one source of radiation that has passed through the subject 14 is detected by the radiation detector 60, and converted into a radiographic image (first radiographic image) in the first image capturing process. In addition, the region to be imaged of the subject 14, which is reflected in the obtained first radiographic image, is identified.

Next, in the first embodiment, an optimum radiation dose with respect to the identified region to be imaged of the subject 14 (an exposure dose that produces a radiographic image suitable for diagnostic interpretation by the doctor 26) and a radiation dose with respect to the region to be imaged of the subject 14 applied during the first image capturing process shown in the first radiographic image are compared, and a judgment is made as to whether or not the radiation dose of the first image capturing process has reached the optimum radiation dose.

If the radiation dose of the first image capturing process has reached the optimum dose, then since the first radiographic image already is a radiographic image suitable for diagnostic interpretation by the doctor 26, retaking of the image is unnecessary. On the other hand, if the radiation dose of the first image capturing process has not reached the optimum dose, then since the first radiographic image is not a radiographic image suitable for diagnostic interpretation by the doctor 26, retaking of the image (the second image capturing process) is judged to be necessary.

Next, in the first embodiment, in the event that the second image capturing process is carried out, at first, the difference between the optimum radiation dose and the radiation dose of the first image capturing process is calculated as a dosage insufficiency. Next, based on the dosage insufficiency and the region to be imaged of the subject 14 identified from the first radiographic image, weighting is performed with respect to all of the radiation sources housed in the radiation output device 20. Thereafter, in accordance with the aforementioned weighting, application of radiation (the second image capturing process) is carried out with respect to the subject 14 from the respective radiation sources, whereby the radiographic image (second radiographic image) formed by the second image capturing process is acquired.

More specifically, with the second image capturing process being applied with respect to a comparatively large region (the chest region) as shown in FIG. 5B, it is necessary that radiation 16a through 16c be applied to a comparatively wide area (the entirety of the imaging area 36), such that radiation 16a through 16c is applied to the entire chest region. Additionally, it is necessary that the cumulative exposure dose with respect to the subject 14 be the optimum dose (i.e., an exposure does suitable for diagnostic interpretation by the doctor 26) corresponding to the chest region, the thickness thereof, etc.

Consequently, with the first embodiment, by means of the second image capturing process with respect to the comparatively large region to be imaged shown in FIG. 5B, weighting is carried out such that the doses of the radiation 16a, 16c emitted from the radiation sources 18a, 18c at both ends are maximum (shown by the thick one-dot-dashed line in FIG. 5B), whereas the dose of the radiation 16b emitted from the central radiation source 18b is smaller, of a degree sufficient to supplement any shortage of the maximum dose level (shown by the thin one-dot-dashed line in FIG. 5B). In accordance with such weighting, radiation 16a through 16c from the respective radiation sources 18a through 18c is irradiated simultaneously or sequentially.

In this case, as a matter of course, portions of the irradiation ranges of radiation (radiation 16a through 16c shown in FIG. 5B) emitted from adjacent radiation sources overlap mutually with each other, so that radiation is applied without gaps with respect to the region to be imaged of the subject 14.

On the other hand, with the second image capturing process being applied with respect to a comparatively small region (the right hand) as shown in FIG. 6B, since the right hand is positioned in a central portion inside of the imaging area 36, radiation 16a through 16c may be applied reliably only to a comparatively narrow area that includes the aforementioned central portion. In this case also, the cumulative exposure dose with respect to the subject 14 during the second image capturing process must be the optimum dose (i.e., an exposure does suitable for diagnostic interpretation by the doctor 26) corresponding to the right hand, the thickness thereof, etc.

Consequently, with the first embodiment, by means of the second image capturing process with respect to the comparatively small region to be imaged shown in FIG. 6B, weighting is carried out such that the dose of the radiation 16b emitted from the central radiation source 18b is maximum (shown by the bold one-dot-dashed line in FIG. 6B), whereas the doses of the radiation 16a, 16c emitted from the radiation sources 18a, 18c at both ends are smaller, of a degree sufficient to supplement any shortage of the maximum dose level (shown by the fine one-dot-dashed line in FIG. 6B). In accordance with such weighting, radiation 16a through 16c from the respective radiation sources 18a through 18c is irradiated simultaneously or sequentially.

In the above explanations, the maximum radiation dose is defined as a radiation dose that is comparatively largest in the case that the doses of radiation 16a through 16c are compared, and the small radiation dose is defined as a radiation dose that is comparatively smaller in the case that the doses of radiation 16a through 16c are compared, such that none of the dosages is in excess of the optimum radiation dose or the aforementioned dosage insufficiency. More specifically, according to the first embodiment, in the second image capturing process of FIGS. 5B and 6B, the doses of radiation 16a through 16c emitted from the respective radiation sources 18a through 18c are weighted, such that the cumulative exposure dose, at the time that the subject 14 is exposed to radiation by respectively applying the radiation 16a through 16c, becomes the optimum dose.

Furthermore, since the time needed for image capturing of the subject 14 is shortened thereby, it is preferable for radiation 16a through 16c to be applied simultaneously from the respective radiation sources 18a through 18c. However, cases are known to occur in which it is difficult for radiation 16a through 16c to be applied simultaneously, in accordance with the ability to supply electric power to the radiation sources 18a through 18c (consumption of electric power in the radiation output device 20), or the image capturing conditions (number of images to be captured) of the subject 14.

In such cases, the radiation sources 18a through 18c may sequentially apply radiation 16a through 16c respectively, so as to reliably capture a radiographic image of the subject 14. If the radiation sources 18a through 18c sequentially apply radiation 16a through 16c respectively, then a central portion of the region to be imaged, which has been positioned, may be irradiated initially, and thereafter, other portions may be irradiated, for thereby lessening blurring of the radiographic image, which may be caused by movement of the region to be imaged during the image capturing process. Alternatively, the region to be imaged may be irradiated initially with radiation, as indicated by the thick one-dot-dashed lines in FIGS. 5B and 6B, and then be irradiated with radiation, as indicated by the thin one-dot-dashed lines shown in FIGS. 5B and 6B.

Accordingly, with the first embodiment, simultaneous or sequential application of radiation 16a through 16c may be selected depending on the ability to supply electric power to the radiation sources 18a through 18c and image capturing conditions of the subject 14.

In the case that radiation 16a through 16c, the doses of which have been weighted in the foregoing manner, is applied to the image capturing region of the subject 14, radiation 16a through 16c that has passed through the image capturing region is detected by the radiation detector 60 and converted into the second radiographic image.

Figure 7:
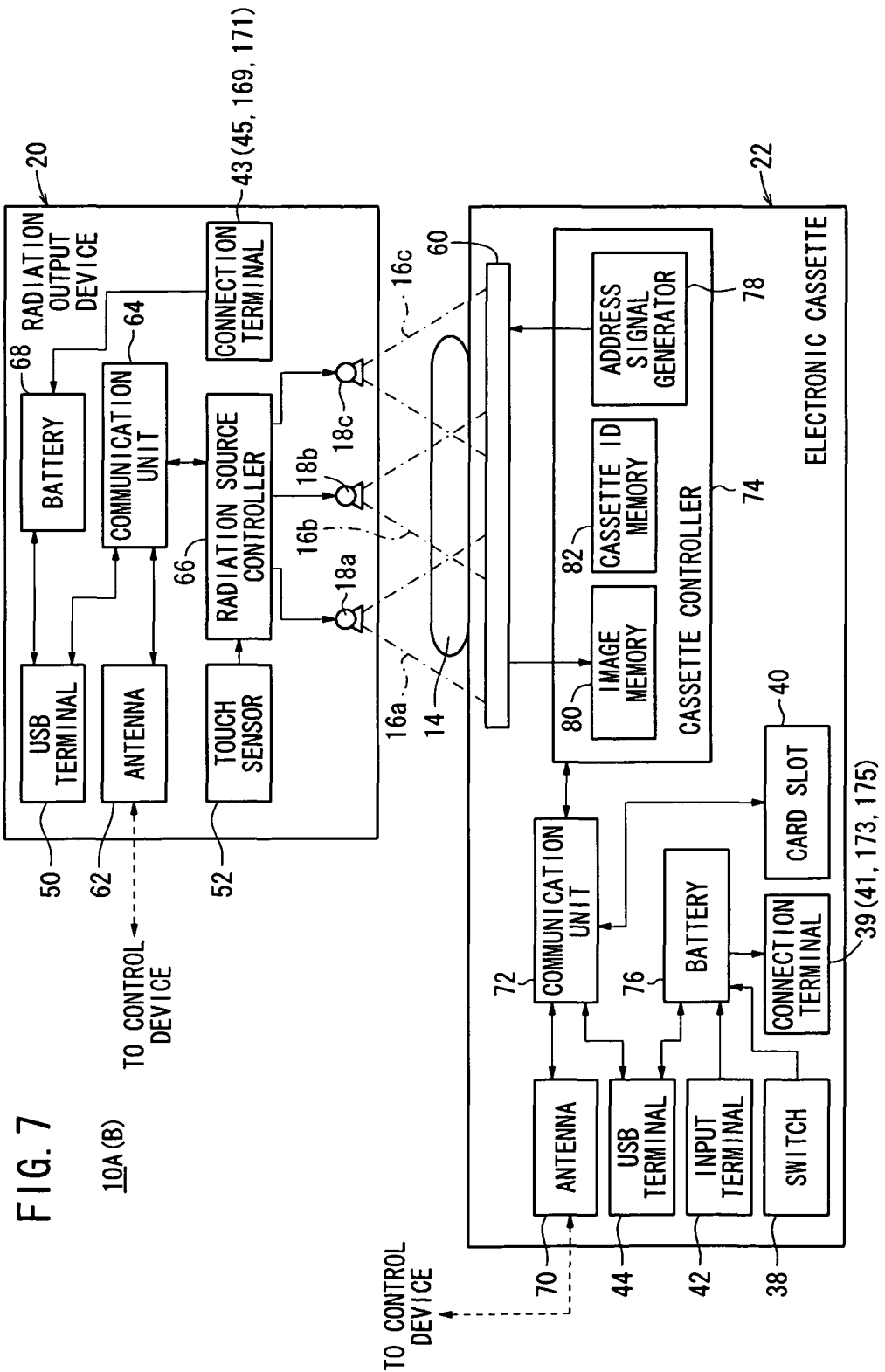
FIG. 7 is a block diagram of the radiation output device and the radiation detecting device shown in FIG. 1.

Internal details of the radiation output device 20, the radiation detecting device 22, and the control device 24 of the radiographic image capturing system 10A will be described in detail below with reference to the block diagrams shown in FIGS. 7 and 8 and the circuit diagram of FIG. 9.

The radiation output device 20 further includes a communication unit 64 for sending signals to and receiving signals from the control device 24 by way of wireless communications through an antenna 62, a radiation source controller 66 for controlling the radiation sources 18*a* through 18*c*, and a battery 68 for supplying electric power to various components of the radiation output device 20.

The battery 68 supplies electric power at all times to the touch sensor 52, the communication unit 64, and the radiation source controller 66. In a case where the touch sensor 52 outputs a detection signal to the radiation source controller 66, at a time that the doctor 26 grips the grip 28, the radiation source controller 66 controls the battery 68 in order to supply electric power to various components of the radiation output device 20.

In a state in which the connection terminals 39, 43 and the connection terminals 41, 45 are electrically connected to each other, and the radiation output device 20 and the radiation detecting device 22 are integrally combined with each other, the battery 68 can be charged by the battery 76 of the radiation detecting device 22. At this time, the radiation source controller 66 does not permit the battery 68 to supply, i.e., prohibits the battery 68 from supplying, electric power to the radiation sources 18*a* through 18*c*, even if a detection signal is received from the touch sensor 52. Accordingly, the radiation source controller 66 controls the battery 68 in order to start supply of electric power to the radiation sources 18*a* through 18*c*, in response to a detection signal received from the touch sensor 52 in a state where the connection terminals 39, 43 and the connection terminals 41, 45 are electrically disconnected from each other so that the radiation output device 20 and the radiation detecting device 22 are separated from each other.

If a cable (not shown) such as a communication cable, a USB cable, or a cable according to IEEE1394, is connected to the radiation output device 20, then the radiation output device 20 can send signals to and receive signals from an external circuit, or may be supplied with electric power via the cable. For example, if a USB cable (not shown) is connected to the USB terminal 50, for example, then the battery 68 can be charged by electric power supplied from an external circuit via the USB cable, and the communication unit 64 can send signals to and receive signals from an external circuit via the USB cable.

The radiation detecting device 22 further includes a communication unit 72 for sending signals to and receiving signals from the control device 24 by way of wireless communications through an antenna 70, a cassette controller (detector controller) 74 for controlling the radiation detector 60, and a battery 76 for supplying electric power to various components of the radiation detecting device 22.

The battery 76 supplies electric power at all times to the cassette controller 74 and the communication unit 72. If the doctor 26 operates (turns on) the switch 38, the battery 76 is capable of supplying electric power to various components of the radiation detecting device 22.

If a cable (not shown) such as a communication cable, a USB cable, or a cable according to IEEE1394, is connected to the radiation detecting device 22, then the radiation detecting device 22 can send signals to and receive signals from an external circuit, or can be supplied with electric power via the cable. For example, if a USB cable (not shown) is connected to the USB terminal 44, for example, then the battery 76 can be charged by electric power supplied from an external circuit via the USB cable, and the communication unit 72 can send signals to and receive signals from an external circuit via the USB cable.

The cassette controller 74 includes an address signal generator 78 for supplying address signals to the radiation detector 60 for reading a radiographic image, an image memory 80 for storing the radiographic image read from the radiation detector 60, and a cassette ID memory 82 for storing cassette ID information, which identifies the radiation detecting device 22.

A circuit arrangement of the radiation detecting device 22, in which the radiation detector 60 is of an indirect conversion type, will be described in detail below with reference to FIG. 9.

The radiation detector 60 comprises an array of thin-film transistors (TFTs) 98 arranged in rows and columns, and a photoelectric conversion layer 96 including pixels 90 and made of a material such as amorphous silicon (a-Si) or the like for converting visible light into electric signals. The photoelectric conversion layer 96 is disposed on the array of TFTs 98. In a case that radiation is applied to the radiation detector 60, the pixels 90, which are supplied with a bias voltage Vb from the battery 76 (see FIG. 7), generate electric charges by converting visible light into analog electric signals, and then store the generated electric charges. Then, as a result of the TFTs 98 being turned on along each row at a time, the stored electric charges can be read from the pixels 90 as an image signal.

The TFTs 98 are connected to respective pixels 90. Gate lines 92, which extend parallel to the rows, and signal lines 94, which extend parallel to the columns, are connected to the TFTs 98. The gate lines 92 are connected to a line scanning driver 100, and the signal lines 94 are connected to a multiplexer 102. The gate lines 92 are supplied with control signals Von, Voff for turning on and off the TFTs 98 along the rows from the line scanning driver 100. The line scanning driver 100 includes a plurality of switches SW1 for switching between the gate lines 92, and an address decoder 104 for outputting a selection signal for selecting one of the switches SW1 at a time. The address decoder 104 is supplied with an address signal from the address signal generator 78 (see FIG. 7) of the cassette controller 74.

The signal lines 94 are supplied with electric charges stored by the pixels 90 via the TFTs 98, which are arranged in columns. The electric charges supplied to the signal lines 94 are amplified by amplifiers 106, which are connected respectively to the signal lines 94. The amplifiers 106 are connected through respective sample and hold circuits 108 to the multiplexer 102. The multiplexer 102 includes a plurality of switches SW2 for successively switching between the signal lines 94, and an address decoder 110 for outputting a selection signal for selecting one of the switches SW2 at a time. The address decoder 110 is supplied with an address signal from the address signal generator 78 of the cassette controller 74. The multiplexer 102 has an output terminal connected to an A/D converter 112. A radiographic image signal, which is generated by the multiplexer 102 based on electric charges from the sample and hold circuits 108, is converted by the A/D converter 112 into a digital image signal representing radiographic image information, which is supplied to the cassette controller 74.

The TFTs 98, which function as switching devices, may be combined with another image capturing device, such as a CMOS (Complementary Metal-Oxide Semiconductor) image sensor or the like. Alternatively, the TFTs 98 may be replaced with a CCD (Charge-Coupled Device) image sensor for shifting and transferring electric charges with shift pulses, which correspond to gate signals in the TFTs.

Figure 8:
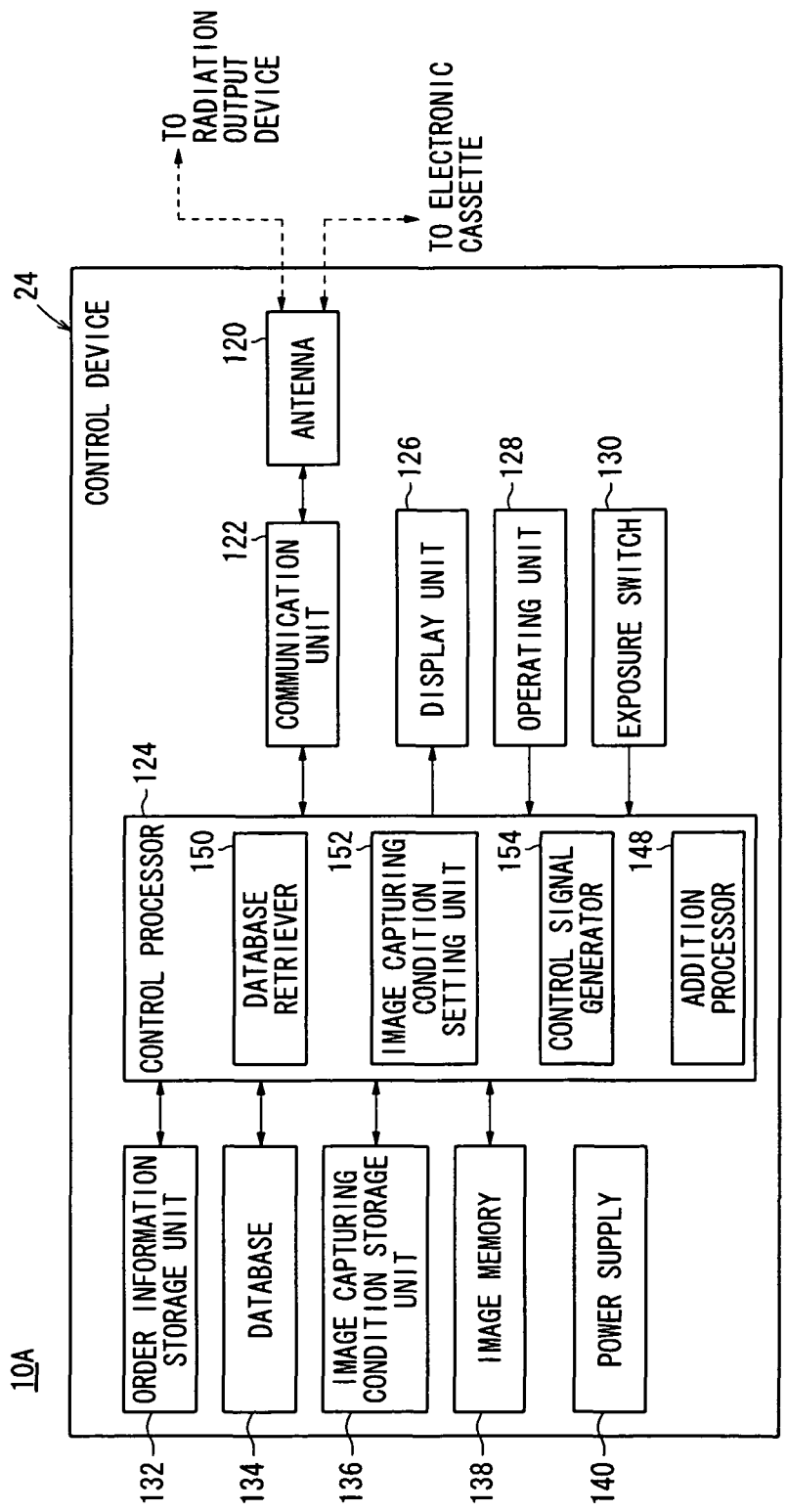
FIG. 8 is a block diagram of a control device of the first embodiment.
Figure 9:
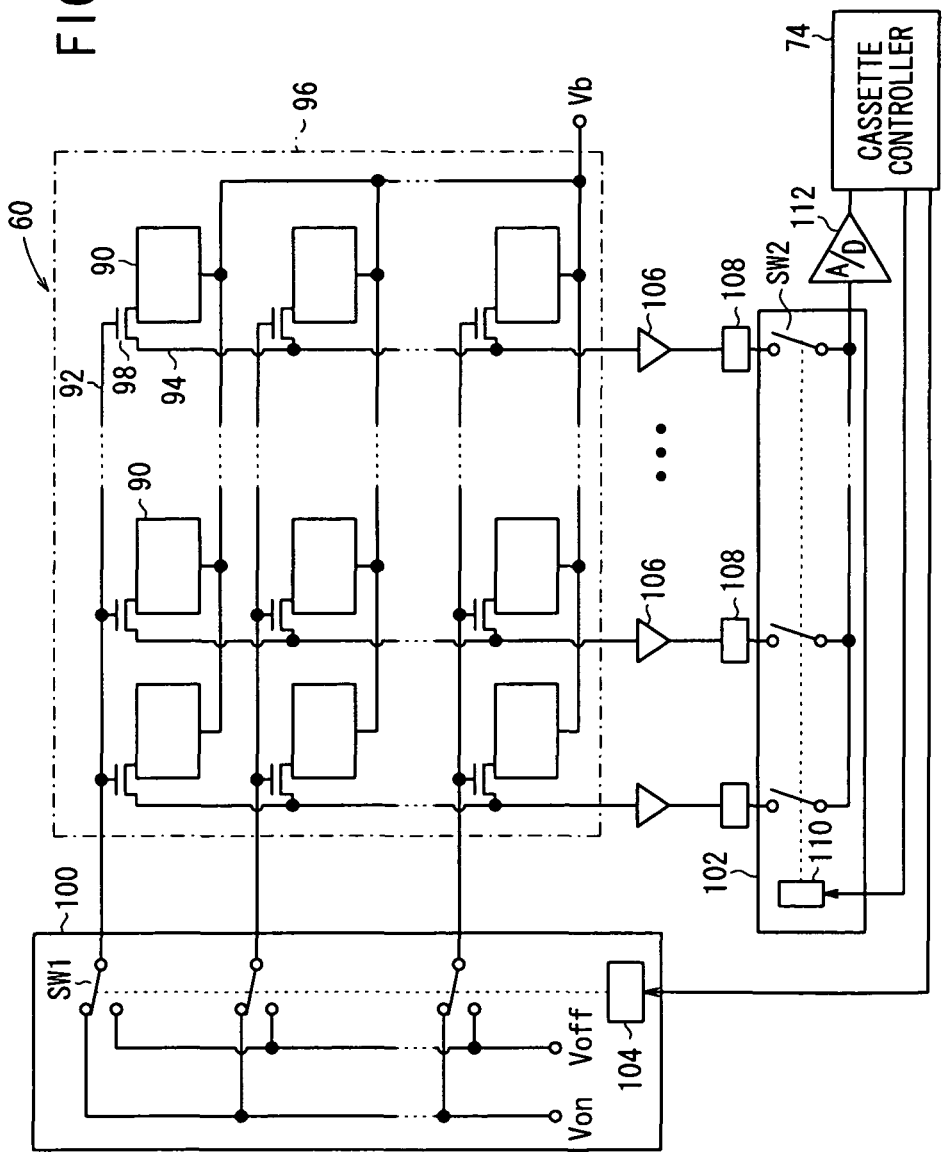
FIG. 9 is a diagram of a circuit arrangement of the radiation detecting device shown in FIG. 7.

As shown in FIG. 8, the control device 24 includes a communication unit 122, a control processor 124, a display unit 126 such as a display panel or the like, an operating unit 128 including a keyboard, a mouse, etc., an exposure switch 130, an order information storage unit 132, a database 134, an image capturing condition storage unit 136, an image memory 138, and a power supply 140.

The communication unit 122 sends signals to and receives signals from the communication unit 64 of the radiation output device 20 and the communication unit 72 of the radiation detecting device 22 by way of wireless communications through the antennas 62, 70, 120. The control processor 124 performs a prescribed control process on the radiation output device 20 and the radiation detecting device 22. The exposure switch 130 can be turned on by the doctor 26 in order to start emitting radiation 16a through 16c from the radiation sources 18a through 18c. The order information storage unit 132 stores order information requesting capture of a radiographic image of the subject 14. The database 134 stores various data concerning weighting of doses of radiation 16a through 16c. The image capturing condition storage unit 136 stores image capturing conditions (first image capturing conditions, second image capturing conditions) under which a region to be imaged of the subject 14 is to be irradiated with radiation 16a through 16c. The image memory 138 stores radiographic images (first radiographic image, second radiographic image) transmitted from the radiation detecting device 22 by way of wireless communications. The power supply 140 supplies electric power to various components of the control device 24.

The order information is generated by the doctor 26 for a radiology information system (RIS), not shown, which generally manages radiographic images and other information that are handled in the radiological department of the hospital, or for a hospital information system (HIS), not shown, which generally manages medical information in the hospital. Such order information includes subject information for identifying the subject 14, including the name, age, gender, etc., information concerning the radiation output device 20 and the radiation detecting device 22, which are used to capture radiographic images, and information concerning a region to be imaged of the subject 14. Such image capturing conditions refer to various conditions under which a region to be imaged of the subject 14 is irradiated with radiation 16a through 16c, including tube voltages and tube currents of the radiation sources 18a through 18c, radiation exposure times of the radiation 16a through 16c, etc.

Further, if the control device 24 comprises a console placed in the image capturing chamber of the radiological department, then the console (control device 24) acquires order information from the RIS or the HIS, and stores the acquired order information in the order information storage unit 132. If the control device 24 comprises a portable terminal, which is carried to and used at a site outside of the hospital, then (1) the doctor 26 may operate the operating unit 128 at the site to provisionally register order information in the order information storage unit 132, (2) order information may be acquired from the RIS or the HIS and then stored in the order information storage unit 132 in the hospital before the control device 24 is carried to the site, or (3) order information may be received from the hospital through a wireless link established between the control device 24 at the site and the hospital after the control device 24 has been carried to the site, and then stored in the order information storage unit 132.

The control processor 124 includes a database retriever 150, an image capturing condition setting unit 152, a control signal generator 154, and an addition processor 148.

The database retriever 150 retrieves desired data corresponding to the region to be imaged of the subject 14 from the database 134. The image capturing condition setting unit 152 sets image capturing conditions based on the data received by the database retriever 150 and the order information. The control signal generator 154 generates an exposure control signal for starting emission of radiation 16a through 16c from the radiation sources 18a through 18c in a case that the doctor 26 turns on the exposure switch 130. The addition processor 148 carries out addition processing on (digital data of) the first radiographic image and (digital data of) the second radiographic image, data of which are stored in the image memory 138, whereby a radiographic image is generated, which is suitable for diagnostic interpretation by the doctor 26.

Figure 10:
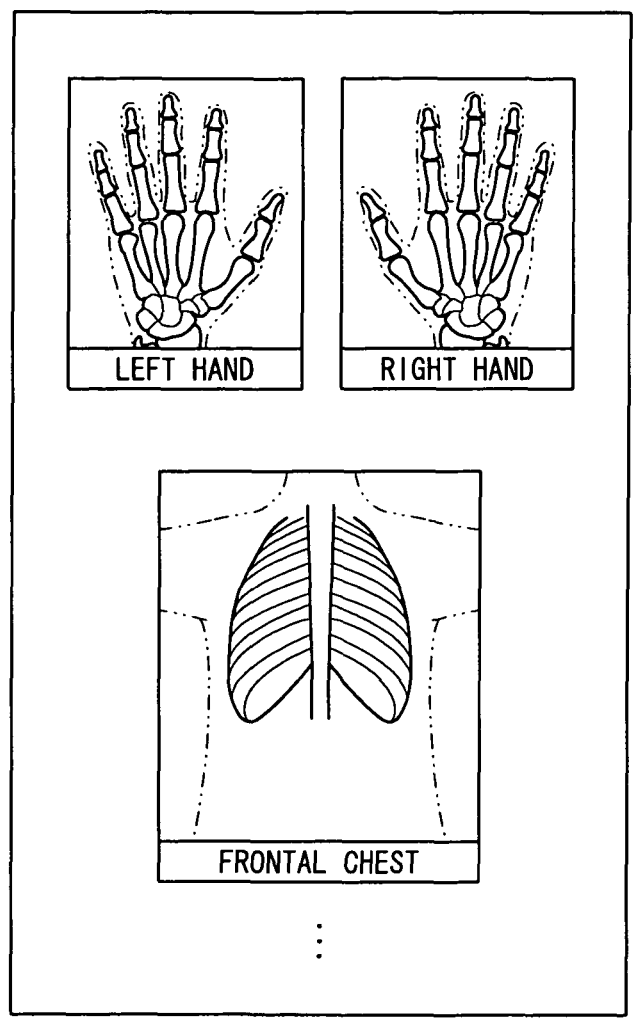
FIG. 10 is a diagram showing, by way of example, object data that is stored in a database shown in FIG. 8.

FIGS. 10 through 12 show object data representative of a plurality of regions to be imaged, and tables of various data concerning weighting of the doses of radiation 16a through 16c.

FIG. 10 shows object data representative of radiographic images of a plurality of regions to be imaged. The object data shown in FIG. 10 includes object data of a chest, as a relatively large region to be imaged, and object data of right and left hands, as relatively small regions to be imaged.

FIG. 11 shows a table that stores therein a plurality of regions to be imaged, thicknesses of the respective regions to be imaged, image capturing techniques for the respective regions to be imaged, and optimum radiation doses (optimum radiation dose data) therefor. The image capturing techniques refer to information representative of orientations of the regions to be imaged with respect to the radiation detecting device 22, and directions along which the regions to be imaged are irradiated with radiation 16a through 16c. Further, FIG. 11 shows by way of example data representing a chest, as a relatively large region to be imaged, data representing a hand, as a relatively small region to be imaged, image capturing techniques (a process for capturing a radiographic image of a frontal chest region, and a process for capturing a radiographic image of the back of the hand), thicknesses of the regions to be imaged, and optimum radiation dose (exposure dose) data therefor.

FIG. 12 shows a table storing a plurality of regions to be imaged and image capturing techniques for the respective regions to be imaged, the numbers of radiation sources housed in the radiation output device 20, and weighting data for doses of radiation to be emitted from the respective radiation sources. More specifically, so as to correspond to FIG. 11, FIG. 12 shows by way of example data representing a chest and a hand, and two and three radiation sources used to emit radiation. For example, if the number of radiation sources used is three, then the weighting data "A" corresponds to the radiation source 18a, the weighting data "B" corresponds to the radiation source 18b, and the weighting data "C" corresponds to the radiation source 18c. If the number of radiation sources used is greater than three, then the number of weighting data in the table shown in FIG. 13 increases depending on the number of radiation sources.

The database 134 (see FIG. 8) is capable of storing various data concerning image capturing processes that can be carried out by the radiographic image capturing system 10A. Data stored in the database 134 can be used even if the subject 14 to be imaged is changed, the region to be imaged of the subject 14 is changed, or a plurality of subjects 14 are imaged sequentially.

A region to be imaged of the subject 14, the thickness of the region to be imaged, and an image capturing technique are manually entered by the doctor 26 through the operating unit 128, or alternatively may be included in the order information of the subject 14. The region to be imaged, the thickness thereof, and the image capturing technique, which are manually entered by the doctor 26 through the operating unit 128, are stored as part of the order information in the order information storage unit 132, whereby the order information is edited.

For capturing a radiographic image of the region to be imaged of the subject 14 (image capturing technique), which is represented by the order information, the database retriever 150 performs the following processes:

In the case that a first radiographic image is obtained by a first image capturing process, the database retriever 150 automatically retrieves, from the database 134, object data that agree with the region to be imaged of the subject 14 reflected in the first radiographic image. The region to be imaged, which is represented by the object data that agree with the region to be imaged, is identified as a region to be imaged of the subject 14 during a process of capturing the second radiographic image. More specifically, the database retriever 150 matches the region to be imaged reflected in the first radiographic image and the respective object data according to a known pattern matching process, for example, and if a correlation (degree of coincidence) between the two images exceeds a predetermined threshold value, identifies a region to be imaged, which is represented by object data the degree of coincidence of which has exceeded the threshold value, as a region to be imaged of the subject 14 in the second radiographic image.

In a case where the database retriever 150 retrieves, from the database 134, a plurality of object data, which are highly likely to agree with the region to be imaged in the first radiograph image (i.e., a plurality of object data the degree of coincidence of which has exceeded the threshold value), then the database retriever 150 may display the first radiographic image and the plural object data on the display unit 126. In this case, the doctor 26 may confirm the content displayed on the display unit 126, and operate the operating unit 128 in order to select object data that appear to agree most closely with the region to be imaged in the first radiographic image. The database retriever 150 may then identify the region to be imaged, which is represented by the selected object data, as a region to be imaged of the subject 14.

The database retriever 150 also identifies the thickness of the region to be imaged of the subject 14, and an image capturing technique therefor. More specifically, if the region to be imaged of the subject 14, which is included in the order information stored in the order information storage unit 132, and the identified region to be imaged of the subject 14 are in agreement with each other, then the database retriever 150 identifies the thickness of the region to be imaged of the subject 14 and the image capturing technique therefor, which are included in the order information, as the thickness of the region to be imaged of the subject 14 and the image capturing technique therefor in the second image capturing process.

If the identified region to be imaged is not in agreement with the region to be imaged of the subject 14 that is included in the order information, or if the thickness of the region to be imaged and an image capturing technique therefor are desired to be reset, then the database retriever 150 may display the identified region to be imaged of the subject 14 and the order information on the display unit 126. In this case, the doctor 26 confirms the displayed content, and operates the operating unit 128 in order to enter a thickness of the region to be imaged and an image capturing technique therefor. Consequently, the database retriever 150 identifies the entered thickness of the region to be imaged of the subject 14 and the entered image capturing technique therefor, as the thickness of the region to be imaged of the subject 14 and the image capturing technique therefor in the second image capturing process. The database retriever 150 can also store the entered thickness of the region to be imaged and the entered image capturing technique therefor as part of the order information in the order information storage unit 132, thereby editing the order information.

The database retriever 150 also automatically retrieves, from the table shown in FIG. 11, optimum radiation dose data based on the identified region to be imaged of the subject 14, the thickness thereof, and the image capturing technique therefor. The database retriever 150 also automatically retrieves optimum weighting data based on the region to be imaged of the subject 14, the image capturing technique therefor, and the number of radiation sources used in the radiation output device 20.

In addition, the database retriever 150 determines whether or not the exposure dose with respect to the region to be imaged by the first image capturing process has reached the optimum radiation dose, by comparing the optimum radiation dose indicated by the retrieved optimum dose data and the dose of radiation at the location of the region to be imaged of the subject 14 reflected in the first radiographic image. Alternatively, in place of comparing radiation doses per se, the database retriever 150 may compare a value (pixel value) of the digital data of the radiographic image corresponding to the optimum radiation dose with a value (e.g., an average of the pixel value) of the digital data at the location of the region to be imaged in the first radiographic image, whereby it can be determined whether or not the exposure dose with respect to the region to be imaged by the first image capturing process has reached the optimum radiation dose.

If the exposure dose by the first image capturing process has reached the optimum dose, then since the first radiographic image is suitable to enable diagnostic interpretation thereof by the doctor 26, the database retriever 150 determines that it is unnecessary to recapture images (i.e., to perform the second image capturing process).

On the other hand, if the exposure dose by the first image capturing process has not reached the optimum dose, then since the first radiographic image is not suitable to enable diagnostic interpretation thereof, the database retriever 150 determines that it is necessary to perform image capturing a second time, and calculates the difference between the optimum exposure dose and the exposure dose of the first image capturing process as a radiation dosage insufficiency.

Then, the database retriever 150 outputs to the image capturing condition setting unit 152 the radiation dosage insufficiency, the retrieved optimum radiation dose data and the retrieved weighting data, together with the order information that was used to retrieve the data, which includes the region to be imaged of the subject 14, the thickness thereof, and the image capturing technique therefor.

If the database retriever 150 retrieves, from the database 134, a plurality of candidates as optimum radiation dose data and weighting data, then the database retriever 150 displays a plurality of candidates and the order information on the display unit 126. The doctor 26 may confirm the plural candidates and the order information displayed on the display unit 126, and operate the operating unit 128 in order to select data that appears to be optimum for the second exposure process. In this case, the database retriever 150 then outputs the optimum radiation dose data and the weighting data, which the doctor 26 has selected from among the plural candidates, and the order information to the image capturing condition setting unit 152. Together therewith, a difference between the optimum radiation dose indicated by the selected optimum dose data and the exposure dose during the first image capturing process is calculated, and the difference after calculation thereof is output to the image capturing condition setting unit 152 as a radiation dosage insufficiency.

In the first image capturing process, the image capturing condition setting unit 152 automatically sets image capturing conditions (first image capturing conditions) for the region to be imaged of the subject 14 during the first image capturing process, based on the order information, and stores the set first image capturing conditions in the image capturing condition storage unit 136. Further, in the second image capturing process, the image capturing condition setting unit 152 automatically sets the image capturing conditions (second image capturing conditions) with respect to the region to be imaged of the subject 14 during the second image capturing process, based on optimum radiation dose data and the weighting data retrieved by the database retriever 150, the order information, and the radiation dosage insufficiency, and stores the set second image capturing conditions in the image capturing condition storage unit 136.

At a time of carrying out the second image capturing process, the image capturing condition setting unit 152 may display the order information, the optimum radiation dose data and the weighting data retrieved by the database retriever 150, and the radiation dose insufficiency on the display unit 126. The doctor 26 may then confirm the content displayed on the display unit 126, and operate the operating unit 128 in order to change details of the weighting data depending on the order information, the state of the subject 14, or the image capturing technique. The image capturing condition setting unit 152 may then set the second exposure conditions based on the weighting data that have been changed.

Further, during the first image capturing process, the database retriever 150 may output to the image capturing condition setting unit 152 the optimum radiation dose data corresponding to the region to be imaged of the subject 14, the thickness thereof and the image capturing technique, and the image capturing condition setting unit 152 may set the first image capturing conditions based on the order information and the optimum radiation dose data.

In the foregoing description, a case has been explained in which the database retriever 150 retrieves optimum radiation dose data from the database 134, and the image capturing condition setting unit 152 sets the second image capturing conditions based on the retrieved optimum radiation dose data and the like. However, in place of this explanation, after the region to be imaged of the subject 14, which is reflected in the first radiographic image, has been identified, the database retriever 150 can calculate the optimum radiation dose corresponding to the region to be imaged, based on the image, which shows therein the identified region to be imaged. In this case, the database retriever 150 outputs to the image capturing condition setting unit 152 optimum radiation dose data indicated by the calculated optimum radiation dose, the weighting data retrieved from the database 134, the order information including the region to be imaged of the subject 14, and the radiation dosage insufficiency, whereupon the image capturing condition setting unit 152 sets the second image capturing conditions based on such information.

[Operations of the First Embodiment]

The radiographic image capturing system 10A according to the first embodiment is basically constructed as described above. Next, operations (a radiographic image capturing method) of the radiographic image capturing system 10A shall be described below with reference to the flowcharts shown in FIGS. 13 and 14. Together with this explanation of operations, as necessary, FIGS. 1 through 12 may also be referred to.

Herein, an explanation shall be made of a case in which first image capturing conditions are set based solely on the order information, and thereafter, the first image capturing process is carried out according to the first image capturing conditions, and next, because the exposure dose indicated by the region to be imaged in the first radiographic image has not reached the optimum radiation dose, a second image capturing process is carried out.

First, in step S1 shown in FIG. 13, the control processor 124 (see FIG. 8) of the control device 24 acquires order information from an external source, and stores the acquired order information in the order information storage unit 132. If the control device 24 is a console located in the image capturing chamber of a radiological department, then the control device 24 may acquire order information from the RIS or the HIS. Further, if the control device 24 is a portable terminal that can be carried to and used at a site outside of the hospital, then the doctor 26 at the site (refer to FIGS. 1, 4B, and 5A through 6B) may operate the operating unit 128 in order to register order information, or order information may be acquired from the RIS or the HIS in the hospital before the control device 24 is carried to the site. Alternatively, order information may be received from the hospital through a wireless link established between the control device 24 at the site and the hospital, after the control device 24 has been carried to the site.

In step S2, based on the order information, the image capturing condition setting unit 152 sets the first image capturing conditions, and stores the set first image capturing conditions in the image capturing condition storage unit 136.

If the order information does not include the thickness of the region to be imaged and the image capturing technique therefor in step S2, then the doctor 26 operates the operating unit 128 in order to enter the thickness of the region to be imaged and the image capturing technique therefor. The order information storage unit 132 stores the entered thickness of the region to be imaged and the entered image capturing technique therefor as part of the order information, thereby editing the order information in the order information storage unit 132.

Next, in step S3, if the doctor 26 turns on the switch 38 of the radiation detecting device 22 (see FIGS. 2A, 2B, 5A through 6B, and 7), then the battery 76 supplies electric power to various components inside the radiation detecting device 22, thereby activating the radiation detecting device 22 in its entirety. Owing thereto, the cassette controller 74 sends an activation signal, which indicates that the radiation detecting device 22 has been activated in its entirety, via a wireless link to the control device 24 (see FIGS. 1 and 8). The battery 76 also applies a bias voltage Vb to the respective pixels 90 (see FIG. 9) of the radiation detector 60.

Based on receipt of the activation signal via the antenna 120 and the communication unit 122, the control processor 124 of the control device 24 sends the first image capturing conditions, which are stored in the image capturing condition storage unit 136, to the radiation detecting device 22 by way of wireless communications. The cassette controller 74 records therein the first image capturing conditions, which are received via the antenna 70 and the communication unit 72.

Incidentally, in the case that the radiation output device 20 and the radiation detecting device 22 are carried to a site, the connection terminals 39, 43 are held in interfitting engagement with each other, and the connection terminals 41, 45 also are held in interfitting engagement with each other. Therefore, the radiation output device 20 is held between the holders 35, 37 of the radiation detecting device 22, and the radiation output device 20 and the radiation detecting device 22 are integrally combined with each other (see FIG. 2A). At this time, the battery 76 charges the battery 68 through the connection terminals 39, 41, 43, 45.

For positioning the region to be imaged of the subject 14, the doctor 26 releases the connection terminals 39, 43 from interfitting engagement with each other, and also releases the connection terminals 41, 45 from interfitting engagement with each other. The radiation output device 20 is separated from the radiation detecting device 22, whereby the radiation output device 20 and the radiation detecting device 22 become disconnected from each other (see FIG. 2B). At this time, the battery 76 stops charging the battery 68.

Then, the doctor 26 positions the region to be imaged of the subject 14, such that the central position of the region to be imaged of the subject 14 and the central position of the imaging area 36 become aligned with each other, and the region to be imaged of the subject 14 is included within the imaging area 36 (see FIGS. 3A and 3B). Thereafter, the doctor 26 grips the grip 28 and orients the radiation output device 20 toward the region to be imaged of the subject 14, so that the distance between the radiation output device 20 and the radiation detecting device 22 become equal to a distance depending on the SID, whereupon the touch sensor 52 outputs a detection signal to the radiation source controller 66. Based on the input of the detection signal, the radiation source controller 66 controls the battery 68 in order to supply electric power to various components of the radiation output device 20, thereby activating the radiation output device 20. Further, the radiation source controller 66 sends an activation signal, which indicates that the radiation output device 20 has been activated, via a wireless link to the control device 24.

Based on receipt of the activation signal via the antenna 120 and the communication unit 122, the control processor 124 of the control device 24 sends the first image capturing conditions stored in the image capturing condition storage unit 136 to the radiation output device 20 by way of wireless communications. The radiation source controller 66 records the first image capturing conditions, which are received via the antenna 62 and the communication unit 64.

Provided that the above preparatory actions have been completed, the doctor 26 grips the grip 28 with one hand and turns on the exposure switch 130 with the other hand (step S4). The control signal generator 154 generates an exposure control signal for starting emission of radiation 16a through 16c from the radiation sources 18a through 18c, and sends the exposure control signal via a wireless link to the radiation output device 20 and the radiation detecting device 22. The exposure control signal at the first image capturing process is a synchronization control signal for capturing the first radiographic image of the region to be imaged of the subject 14, as a result of synchronizing start of emission of radiation 16a through 16c from the radiation sources 18a through 18c and the detection and conversion of such radiation 16a through 16c into a radiographic image by the radiation detector 60.

Upon receipt of the exposure control signal by the radiation source controller 66, the radiation source controller 66 controls the radiation sources 18a through 18c in order to apply prescribed doses of radiation 16a through 16c to the subject 14 according to the first image capturing conditions. The radiation sources 18a through 18c emit radiation 16a through 16c, which is output from the radiation output device 20 and applied to the region to be imaged of the subject 14, for a given exposure time (irradiation time) based on the first image capturing conditions (step S5).

In step S6, radiation 16a through 16c passes through the subject 14 and reaches the radiation detector 60 in the radiation detecting device 22. If the radiation detector 60 is of an indirect conversion type, then the scintillator of the radiation detector 60 emits visible light having an intensity depending on the intensity of the radiation 16a through 16c. The pixels 90 of the photoelectric conversion layer 96 (see FIG. 9) convert the visible light into electric signals and store the electric signals as electric charges therein. The electric charges, which are stored in the pixels as representing a radiographic image (first radiographic image) of the subject 14, are read as address signals, which are supplied from the address signal generator 78 of the cassette controller 74 (see FIG. 7) to the line scanning driver 100 and the multiplexer 102.

More specifically, in response to the address signal supplied from the address signal generator 78, the address decoder 104 of the line scanning driver 100 outputs a selection signal to select one of the switches SW1, which supplies the control signal Von to the gates of the TFTs 98 connected to the gate line 92 that corresponds to the selected switch SW1. In response to the address signal supplied from the address signal generator 78, the address decoder 110 of the multiplexer 102 outputs a selection signal to successively turn on the switches SW2 to switch between the signal lines 94, for thereby reading through the signal lines 94 the electric charges stored in the pixels 90 connected to the selected gate line 92.

The electric charges of the first radiographic image, which are read from the pixels 90 connected to the selected gate line 92, are amplified respectively by the amplifiers 106, sampled by the sample and hold circuits 108, supplied to the A/D converter 112 via the multiplexer 102, and converted into digital signals. The digital signals, which represent the first radiographic image, are stored in the image memory 80 of the cassette controller 74 (step S7).

Similarly, the address decoder 104 of the line scanning driver 100 successively turns on the switches SW1 to switch between the gate lines 92, according to the address signals supplied from the address signal generator 78. The electric charges stored in the pixels 90 connected to the successively selected gate lines 92 are read through the signal lines 94, processed by the multiplexer 102, and converted into digital signals by the A/D converter 112. The digital signals are stored in the image memory 80 of the cassette controller 74 (step S7).

The first radiographic image, which is stored in the image memory 80, and the cassette ID information, which is stored in the cassette ID memory 82, are sent to the control device 24 wirelessly via the communication unit 72 and the antenna 70. The control processor 124 of the control device 24 stores the first radiographic image and the cassette ID information, which are received via the antenna 120 and the communication unit 122, in the image memory 138, and displays the first radiographic image on the display unit 126 (step S8). Consequently, the doctor 26, by observing the displayed content on the display unit 126, can confirm that the first radiographic image has been obtained.

Next, in step S9, the database retriever 150 retrieves automatically from the database 134 object data that matches with the region to be imaged, which is reflected in the first radiographic image. The region to be imaged, which is indicated by the object data that agree with the aforementioned region to be imaged, is identified as a region to be imaged of the subject 14 in the second image capturing process.

Next, the database retriever 150 identifies the thickness and the image capturing technique in relation to the identified region to be imaged of the subject 14. In this case, if the region to be imaged of the subject 14 that is included in the order information stored in the order information storage unit 132 and the region to be imaged of the subject 14 identified by the database retriever 150 agree with one another, then the database retriever 150 identifies, as is, the thickness and the image capturing technique within the order information as the thickness and image capturing technique for the region to be imaged of the subject 14 in the second image capturing process.

In step S9, if a plurality of object data are retrieved, having a degree of coincidence with the region to be imaged reflected in the first radiographic image that has exceeded a predetermined threshold value, then the database retriever 150 may display the first radiographic image and the plural object data on the display unit 126. The doctor 26 may confirm the content displayed on the display unit 126, and can operate the operating unit 128 in order to select object data, which appear to be in agreement most closely with the region to be imaged in the first radiographic image. The database retriever 150 then identifies the region to be imaged, which is represented by the object data selected by the doctor 26, as the region to be imaged of the subject 14.

Further, in step S9, if the region to be imaged of the subject 14, which is reflected in the first radiographic image, is not in agreement with the region to be imaged of the subject 14, which is included in the order information, or if the thickness of the region to be imaged of the subject 14 and the image capturing technique therefor are to be reset, then the database retriever 150 may display on the display unit 126 the identified region to be imaged of the subject 14 and the order information. The doctor 26 can then confirm the content displayed on the display unit 126, and operate the operating unit 128 in order to enter a thickness of the region to be imaged of the subject 14, and an image capturing technique therefor. As a consequence, the database retriever 150 can identify the entered thickness of the region to be imaged of the subject 14 and the entered image capturing technique therefor, as the thickness of the region to be imaged of the subject 14 and the image capturing technique therefor in the second image capturing process. Further, the database retriever 150 can store the entered thickness of the region to be imaged of the subject 14 along with the entered image capturing technique therefor, as part of the order information in the order information storage unit 132, thereby editing the order information store in the order information storage unit 132.

In step S10, as shown in FIG. 14, the database retriever 150 (see FIG. 8) automatically retrieves, from the database 134, a region to be imaged of the subject 14, a thickness thereof and image capturing technique therefor, which correspond to the region to be imaged of the subject 14 (see FIGS. 1, 3A, 3B and 5A through 7), the thickness thereof, and the image capturing technique therefor that have been identified in step S9 of FIG. 13, along with optimum radiation dose data corresponding to such items of information. Further, the database retriever 150 also automatically retrieves from the database 134 weighting data corresponding to the region to be imaged of the subject 14 that has been identified in step S9, and the image capturing technique therefor.

Next, in step S11, the database retriever 150 compares the optimum radiation dose indicated by the retrieved optimum radiation dose data with the radiation dose at the location of the region to be imaged of the subject 14 in the first radiographic image, and determines whether or not the exposure dose of the region to be imaged in the first image capturing process has reached the optimum radiation dose. In this case, if the exposure dose during the first image capturing process has not reached the optimum radiation dose (step S11: NO), then since a first radiographic image has not been produced which is suitable for diagnostic interpretation by the doctor 26, the database retriever 150 judges that it is necessary to carry out the second image capturing process, and calculates the difference between the optimum exposure dose and the exposure dose during the first image capturing process as a radiation dosage insufficiency (step S12).

Additionally, the database retriever 150 outputs to the image capturing condition setting unit 152, as various data necessary for the second image capturing process, the dosage insufficiency, the retrieved optimum radiation dose data and weighting data, the region to be imaged of the subject 14 used for retrieval, and the order information including the thickness of the region to be imaged and the image capturing technique therefor (step S13).

In step S10, if the database retriever 150 retrieves a plurality of candidates for the optimum radiation dose data and the weighting data, then the database retriever 150 may display the plural candidates and the order information on the display unit 126. In this case, the doctor 26 can confirm the content displayed on the display unit 126, and can operate the operating unit 128 in order to select a candidate (data) that appears to be most optimum for the second image capturing process. The database retriever 150 then regards the optimum radiation dose data and the weighting data, which the doctor 26 has selected from among the plural candidates, as data necessary for the second image capturing process. Together therewith, the database retriever 150 can calculate the difference between the optimum radiation dose indicated by the selected optimum radiation dose data and the exposure dose of the first image capturing process as the radiation dosage insufficiency (step S12).

In step S14, the image capturing condition setting unit 152 sets the second image capturing conditions under which the region to be imaged of the subject 14 is to be irradiated with radiation 16a through 16c emitted from the radiation sources 18a through 18c, based on the entered optimum radiation dose data, the entered weighting data, the order information, and the dosage insufficiency.

If the region to be imaged of the subject 14 is a chest, as shown in FIG. 5B, then the image capturing condition setting unit 152 (see FIG. 8) sets the second image capturing conditions (tube voltages, tube currents, and irradiation times) according to the contents of the above data, such that the doses of radiation 16a, 16c emitted from the radiation sources 18a, 18c at the ends are of a maximum dose level, and the dose of radiation 16b emitted from the radiation source 18b at the center is of a lower dose level, sufficient to supplement any shortage of the maximum dose level, and stores the set second image capturing conditions in the image capturing condition storage unit 136.

Further, if the region to be imaged of the subject 14 is a hand (right hand), as shown in FIG. 6B, then the image capturing condition setting unit 152 (see FIG. 8) sets the second image capturing conditions (tube voltages, tube currents, and irradiation times) according to the above data, such that the dose of radiation 16b emitted from the radiation source 18b at the center is of a maximum dose level, and the doses of radiation 16a, 16c emitted from the radiation sources 18a, 18c at the ends are of a lower dose level, sufficient to supplement any shortage of the maximum dose level, and stores the set second image capturing conditions in the image capturing condition storage unit 136.

In addition, the control processor 124 sends the set second image capturing conditions to the radiation output device 20 and the radiation detecting device 22 (see FIG. 7) wirelessly via the communication unit 122 and the antenna 120. The radiation source controller 66 of the radiation output device 20 registers the second image capturing conditions received via the antenna 62 and the communication unit 64, whereas the cassette controller 74 of the radiation detecting device 22 registers the second image capturing conditions received via the antenna 70 and the communication unit 72.

In step S14, the image capturing condition setting unit 152 may display the entered optimum radiation dose data, the entered weighting data, the order information, and the dosage insufficiency on the display unit 126. The doctor 26 may then confirm the content displayed on the display unit 126, and by operating the operating unit 128, can change details of the weighting data depending on the order information, the state of the subject 14, or the image capturing technique for the subject 14, as well as setting desired second image capturing conditions in accordance with the contents of such data, which have been changed. In this case, the image capturing condition setting unit 152 stores the set second image capturing conditions in the image capturing condition storage unit 136.

Further, in the case that, in step S9 of FIG. 13, the database retriever 150, after having identified the region to be imaged of the subject 14 reflected in the first radiographic image, calculates an optimum radiation dose corresponding to the region to be imaged based on the image in which the region to be imaged is displayed, and retrieves weighting data from the database 134, then in step S14 of FIG. 14, the image capturing condition setting unit 152 (see FIG. 8) sets the second image capturing conditions based on the order information including the region to be imaged of the subject 14, the optimum radiation dose data indicated by the calculated optimum radiation dose, the dosage insufficiency, and the retrieved weighting data.

Provided that the above preparatory actions have been completed, the doctor 26 grips the grip 28 with one hand and turns on the exposure switch 130 with the other hand (step S15). The control signal generator 154 generates an exposure control signal for starting emission of radiation 16a through 16c from the radiation sources 18a through 18c, and sends the exposure control signal via a wireless link to the radiation output device 20 and the radiation detecting device 22. The exposure control signal of the second image capturing process is a synchronization control signal for capturing a second radiographic image of the region to be imaged of the subject 14, as a result of synchronizing start of emission of radiation 16a through 16c from the radiation sources 18a through 18c and the detection and conversion of such radiation 16a through 16c into a radiographic image by the radiation detector 60.

Upon receipt of the exposure control signal by the radiation source controller 66, the radiation source controller 66 controls the radiation sources 18a through 18c in order to apply prescribed doses of radiation 16a through 16c to the subject 14 according to the second image capturing conditions. The radiation sources 18a through 18c respectively emit radiation 16a through 16c, which is output externally from the radiation output device 20 and applied to the region to be imaged of the subject 14, for a given exposure time (irradiation time) based on the second image capturing conditions (step S16).

In this case, if the region to be imaged of the subject 14 is a chest, as shown in FIGS. 3A and 5B, then the chest is irradiated with large doses of radiation 16a, 16c from the radiation sources 18a, 18c at both ends, whereas the region to be imaged is irradiated with a lower dose of radiation 16b from the central radiation source 18b, sufficient to supplement any shortage of the large dose level.

Further, if the region to be imaged of the subject 14 is a right hand, as shown in FIGS. 3B and 6B, then the region to be imaged of the subject 14 is irradiated with a large dose of radiation 16b from the central radiation source 18b, whereas the right hand of the subject 14 is irradiated with lower doses of radiation 16a, 16c from the radiation sources 18a, 18c at both ends, sufficient to supplement any shortage of the large dose level.

Additionally, in step S17, after the radiation 16a through 16c has passed through the subject 14 and reached the radiation detector 60 of the radiation detecting device 22, in the case that the radiation detector 60 is a detector of an indirect conversion type, the scintillator constituting the radiation detector 60 emits visible light of an intensity corresponding to the intensity of the radiation 16a through 16c, whereupon the respective pixels 90 of the photoelectric conversion layer 96 convert the visible light into electric signals, which are stored as charges. Then, the electric charge information, which is stored in each of the pixels 90 as representing a radiographic image (second radiographic image) of the subject 14, are read as address signals, which are supplied from the address signal generator 78 of the cassette controller 74 to the line scanning driver 100 and the multiplexer 102.

In addition, the second radiographic image made up of the read electric charge information is stored in the image memory 80 of the cassette controller 74 (step S18), and the second radiographic image, which is stored in the image memory 80, and the cassette ID information, which is stored in the cassette ID memory 82, are sent to the control device 24 wirelessly via the communication unit 72 and the antenna 70. The control processor 124 of the control device 24 stores the second radiographic image and the cassette ID information, which are received via the antenna 120 and the communication unit 122, in the image memory 138, and displays the second radiographic image on the display unit 126 (step S19).

Processing of steps S17 through S19 concerning the second radiographic image are basically the same as steps S6 through S8 concerning the first radiographic image. More specifically, since steps S17 through S19 can be reproduced simply by replacing terms relating to image capturing of the first radiographic image in the explanations of steps S6 through S8 with terms relating to image capturing of the second radiographic image, detailed explanations of steps S17 through S19 have been omitted.

Next, the addition processor 148 carries out a predetermined addition process to add the digital data of the first radiographic image and the digital data of the second radiographic image stored in the image memory 138, whereby a radiographic image is generated, which is suitable for diagnostic interpretation thereof by the doctor 26 (step S20). The generated radiographic image is displayed on the display unit 126, together with being stored in the image memory 138 (step S21). In step S21, if desired, in addition to the aforementioned radiographic image, the first radiographic image and the second radiographic image, which were the subjects of the addition processing, may be displayed together therewith.

After having confirmed that a radiographic image suitable for enabling diagnostic interpretation has been obtained by visually checking the content displayed on the display unit 126, the doctor 26 releases the subject 14 from the positioned condition, and removes the hand from the grip 28. Owing thereto, the touch sensor 52 stops outputting the detection signal, and the radiation source controller 66 stops supplying electric power from the battery 68 to the various components of the radiation output device 20. As a result, the radiation output device 20 is brought into a sleep mode or is shut down. Further, if the doctor 26 presses (turns off) the switch 38, then the battery 76 stops supplying electric power to the various components of the radiation detecting device 22, and the radiation detection device 22 is brought into a sleep mode or is shut down.

Then, the doctor 26 brings the connection terminals 39, 43 into interfitting engagement with each other, and also brings the connection terminals 41, 45 into interfitting engagement with each other, thereby holding the radiation output device 20 between the holders 35, 37, so as to integrally combine the radiation output device 20 and the radiation detecting device 22 with each other (see FIG. 2A).

Moreover, in step S11, if the dose of radiation at the location of the region to be imaged in the first radiographic image has reached the optimum radiation dose indicated by the optimum radiation dose data retrieved by the database retriever 150, in this case, the database retriever 150 judges that a radiographic image has been obtained, only by carrying out the first image capturing process, which is suitable for diagnostic interpretation by the doctor 26 (step S11: YES), and thereafter, the first radiographic image is displayed again on the display unit 126 as the radiographic image suitable for enabling image diagnosis, together with being stored in the image memory 138 (step S21).

Further, in the case that the size of the dosage insufficiency is so large as to come near to the optimum dose, as a result of the dose indicated by the first radiographic image being excessively small, then the control processor 124, as shown by the broken line in FIG. 14, does not implement the addition process (step S20) by the addition processor 148, and the process of step S21 is carried out, such that the second radiographic image, in its present state, is regarded as being a radiographic image suitable to enable diagnostic interpretation thereof by the doctor 26.

[Advantages of the First Embodiment]

As described above, with the radiographic image capturing system 10A and the radiographic image capturing method according to the first embodiment, among the at least two radiation sources (i.e., the three radiation sources 18a through 18c, as shown in FIGS. 4A through 6B) housed in the radiation output device 20, the first image capturing process is carried out with respect to the subject 14 by at least one of the radiation sources (i.e., the radiation source 18b shown in FIGS. 4A through 6B). If the radiation dose with respect to the region to be imaged of the subject 14 indicated in the first radiographic image obtained from the first image capturing process does not reach the optimum dose (i.e., an exposure dose that produces a radiographic image suitable for diagnostic interpretation by the doctor 26), then the doses of radiation (radiation 16a through 16c) emitted from the at least two radiation sources in the second image capturing process are weighted, so as to supplement the difference (dosage insufficiency) between the optimum dose and the dose of the first image capturing process.

Accordingly, even though image capturing is carried out a second time with respect to the region to be imaged of the subject 14, the cumulative exposure dose applied to the region to be imaged of the subject 14 by the initial image capturing process and the repeated image capturing process (the first image capturing process and the second image capturing process) becomes equivalent to the optimum dose.

In other words, with the first embodiment, even in the case that image capturing is performed again (second image capturing process) with respect to the subject 14 due to the fact that a desired radiographic image could not be obtained by the first image capturing process, the subject 14 is not exposed to radiation unnecessarily.

Further, assuming that the addition processor 148 performs addition processing to add the digital data of the first radiographic image and the digital data of the second radiographic image, a radiographic image can easily be obtained of an exposure dosage sufficient to enable diagnostic interpretation of the obtained radiographic image by the doctor 26.

In this manner, according to the first embodiment, an irradiation range of the radiation 16a through 16c is not established simply by enabling a region to be imaged of the subject 14 to be covered, but rather, based on the first radiographic image, radiation doses of radiation 16a through 16c emitted from the respective radiation sources 18a through 18c are weighted during the second image capturing process. Additionally, because the region to be imaged of the subject 14 is reflected in the first radiographic image, the doses of radiation 16a through 16c are weighted according to the region to be imaged of the subject 14.

According to the first embodiment, therefore, even if a radiographic image of the subject 14 is captured (by the first and second image capturing processes) at a short SID using field-emission radiation sources, the irradiation range of radiation 16a through 16c can easily be enlarged, and the subject 14 can be irradiated with an optimum dose (exposure dose) of radiation 16a through 16c.

Further, in the first embodiment, if the dose of radiation 16a through 16c indicated in the first radiographic image has reached the optimum radiation dose, since the first radiographic image already is a radiographic image of an exposure dose sufficient for diagnostic interpretation by the doctor 26, then naturally, carrying out of the second image capturing process (recapturing) becomes unnecessary.

Further, the database retriever 150 identifies the region to be imaged of the subject 14, which is represented by the object data that agree with the region to be imaged of the subject 14 and which is reflected in the first radiographic image, as a region to be imaged of the subject 14 for the second image capturing process. The database retriever 150 then retrieves optimum radiation dose data depending on the identified region to be imaged of the subject 14, the thickness thereof, and the image capturing technique therefor, and together therewith, retrieves weighting data depending on the region to be imaged of the subject 14 and the image capturing technique therefor. If the radiation dose of the region to be imaged indicated in the first radiographic image does not reach the optimum radiation dose of the optimum radiation dose data, the database retriever 150 judges that the second image capturing process is needed and calculates the dosage insufficiency, and thereafter, outputs the retrieved optimum radiation dose data, the retrieved weighting data, the order information, and the dosage insufficiency to the image capturing condition setting unit 152. The image capturing condition setting unit 152 is thus capable of setting the second image capturing conditions accurately and efficiently. As a result, as long as the radiation output device 20 applies radiation 16a through 16c from the respective radiation sources 18a through 18c to the region to be imaged of the subject 14 according to the second image capturing conditions, a second radiographic image, which is sufficient to enable diagnostic interpretation thereof by the doctor 26, can be acquired reliably.

Further, after the database retriever 150 has identified the region to be imaged of the subject 14 reflected in the first radiographic image, because it is possible to calculate an optimum radiation dose corresponding to the region to be imaged based on the image in which the identified region to be imaged is shown, in the case that the optimum radiation dose data is not stored in the database 134, or even if desired optimum radiation dose data cannot be retrieved from the database 134, the optimum radiation dose for the second image capturing process can be identified, and based on the identified optimum radiation dose, the second image capturing conditions can be set in the image capturing condition setting unit 152.

Further, in the first image capturing and second image capturing processes, because the region to be imaged of the subject 14 is positioned in a central portion of the imaging area 36 (see FIGS. 3A and 3B), and is irradiated with radiation 16a through 16c, which is directed toward the region to the imaged of the subject 14 from the respective radiation sources 18a through 18c of the radiation output device 20, which confront the central portion, a radiographic image that contains the region to be imaged therein can be acquired reliably.

The image capturing condition setting unit 152 may change details of the weighting data retrieved by the database retriever 150, depending on the order information, the state of the subject 14, or the image capturing technique for the subject 14. Thus, more accurate first radiation capturing conditions can be set depending on the actual image capturing technique for the subject 14.

Furthermore, with the first embodiment, if three radiation sources 18a through 18c are housed in the radiation output device 20, during the second image capturing process, concerning the radiation 16a through 16c emitted from the respective radiation sources 18a through 18c, weighting of the radiation doses thereof can be performed depending on the region to be imaged of the subject 14 in the following manner.

As shown in FIG. 5B, if the second image capturing process is performed on a relatively large region to be imaged of the subject 14 (e.g., the chest of the subject 14), then the doses of radiation 16a through 16c emitted from the radiation sources 18a through 18c are weighted such that the doses of radiation 16a, 16c emitted from the radiation sources 18a, 18c at the ends are of a maximum dose level, whereas the dose of radiation 16b emitted from the radiation source 18b at the center is of a lower dose level.

As shown in FIG. 6B, if the second image capturing process is performed on a relatively small region to be imaged of the subject 14 (e.g., a hand of the subject 14), then the dose of radiation 16b emitted from the radiation source 18b at the center is of a maximum dose level, whereas the doses of radiation 16a, 16c emitted from the radiation sources 18a, 18c at the ends are of a lower dose level.

With the doses of radiation 16a through 16c weighted in the foregoing manner, even if a radiographic image of the subject 14 is captured at a short SID using field-emission radiation sources 18a through 18c, the irradiation range of the radiation 16a through 16c can easily be enlarged, and the subject 14 can be irradiated with an optimum dose (exposure dose) of radiation 16a through 16c. Since the subject 14 is irradiated with an optimum dose of radiation depending on the subject 14, by the addition processor 148 carrying out addition processing on the first radiographic image and the second radiographic image, it is possible to acquire a radiographic image suitable for diagnostic interpretation by the doctor 26, while also preventing the subject from being exposed to radiation unnecessarily.

In the example shown in FIG. 5B, image capturing of the second radiographic image with respect to a relatively large region to be imaged can be carried out efficiently. In the example shown in FIG. 6B, image capturing of the second radiographic image with respect to a relatively small region to be imaged can be carried out efficiently.

The grip 28 is mounted on the side of the radiation output device 20, which is remote from the side where radiation 16a through 16c is emitted from the radiation sources 18a through 18c. Consequently, while holding the grip 28 with one hand, the doctor 26 can orient the radiation output device 20 toward the subject 14 and the radiation detecting device 22. Further, the doctor 26 can confirm images and data displayed on the display unit 126, and operate the operating unit 128 or the exposure switch 130 with the other hand. In a case where radiation 16a through 16c is emitted from the radiation sources 18a through 18c while the doctor 26 grips the grip 28, the doctor 26 is reliably prevented from being irradiated with (exposed to) radiation 16a through 16c.

Further, in the case that the doctor 26 brings the connection terminals 39, 43 and the connection terminals 41, 45 respectively into interfitting engagement with each other, thereby holding the radiation output device 20 between the holders 35, 37 and integrally combining the radiation output device 20 and the radiation detecting device 22 with each other, the doctor 26 can easily carry the radiation output device 20 and the radiation detecting device 22 together. At this time, since the connection terminals 39, 43 and the connection terminals 41, 45 are electrically connected respectively to each other, the battery 76 of the radiation detecting device 22 can charge the battery 68 of the radiation output device 20.

Still further, while the radiation output device 20 and the radiation detecting device 22 are integrally combined with each other, the radiation source controller 66 can prohibit the battery 68 from supplying electric power to the radiation sources 18a through 18c, for thereby preventing radiation 16a through 16c from being emitted while the radiation output device 20 and the radiation detecting device 22 are being carried. Also, since the side of the radiation output device 20 where radiation 16a through 16c is emitted from the radiation sources 18a through 18c faces toward the side of the housing 30 of the radiation detecting device 22 while the radiation output device 20 and the radiation detecting device 22 are integrally combined with each other, the doctor 26 is reliably prevented from being exposed to radiation 16a through 16c, even if such radiation 16a through 16c is emitted in error.

The control device 24 sends signals to and receives signals from the radiation output device 20 and the radiation detecting device 22 via a wireless link. Inasmuch as the radiation output device 20, the radiation detecting device 22, and the control device 24 are connected wirelessly via the same wireless link, and since no cables (USB cables) are required for signals to be sent and received therebetween, the doctor 26 can carry out work free of obstacles. Therefore, the doctor 26 can efficiently work on the radiographic image capturing system 10A in an obstacle-free environment. In addition, the radiographic image capturing system 10A is made up of a relatively small number of parts, since no cables are required for connection between the radiation output device 20, the radiation detecting device 22, and the control device 24. According to the first embodiment, signals may be sent and received via optical wireless communications using infrared rays or the like, rather than by means of conventional wireless communications.

According to the first embodiment, the control device 24 can also send signals to and receives signals from the radiation output device 20 and the radiation detecting device 22 via a wired link. For example, the radiation output device 20, the radiation detecting device 22, and the control device 24 may be electrically connected by USB cables (not shown), so that the power supply 140 of the control device 24 can charge the battery 68 of the radiation output device 20 and the battery 76 of the radiation detecting device 22. Further, the control device 24 can reliably send exposure control signals and image capturing conditions to the radiation output device 20 and the radiation detecting device 22, and the radiation detecting device 22 can reliably send radiographic images to the control device 24. Accordingly, such a wired link enables signals to be sent and received reliably, and also allows the batteries 68, 76 to be charged reliably.

The batteries 68, 76 may be charged to a power level, which depends on at least the number of radiographic images to be captured of the subject 14. Consequently, during the radiographic image capturing process, a number of radiographic images of the subject 14 can reliably be captured.

In this case, the batteries 68, 76 may be charged within a time zone in which radiographic image capturing process is not being carried out. In this manner, the batteries 68, 76 are not charged during the radiographic image capturing process, and the captured radiographic images are transmitted after completion of the radiographic image capturing process. Therefore, during the radiographic image capturing process, noise due to charging of the batteries 68, 76 is prevented from being added to the generated electric charges (analog signals), or from being added to radiographic images while the radiographic images are being transmitted.

More specifically, the batteries 68, 76 may be charged within a time zone, except for a period (storage period) during which radiation 16a through 16c having passed through the subject 14 is converted into electric signals by the radiation detector 60 and the electric signals are stored as electric charges in the pixels 90, a period (readout period) during which the electric charges stored in the pixels 90 are read, or a conversion period during which the read electric charges (analog signals) are converted into digital signals by the A/D converter 112, or a period covering two or more of the aforementioned storage, readout, and conversion periods, or a period covering all of the storage, readout, and conversion periods.

More specifically, in the above three periods, i.e., in the storage, readout, and conversion periods, the image signals (radiographic image) are highly susceptible to noise. Particularly during the storage and readout periods, the electric charges generated by the pixels 90 are so small that they will be adversely affected by noise. Further, during the conversion period, the analog signals representing the electric charges are less resistant to noise than digital signals prior to A/D conversion thereof, and any noise added to the analog signals tends to be converted into digital signals and appear in the image data.

A portion of the storage period includes a time during which the radiation sources 18a through 18c apply radiation 16a through 16c to the subject 14. After the storage period has started, radiation should start being applied as quickly as possible, and after radiation has stopped being applied, the readout period should start immediately thereafter. Any time lag between these events should be minimized, so as to reduce dark current and to increase the quality of the generated radiographic image. Further, the readout period is a period during which the TFTs 98 are turned on to supply signals through the amplifiers 106, etc., and to the A/D converter 112. Although the readout period and the conversion period occur substantially at the same time, the readout period actually starts slightly earlier than the conversion period.

Since the batteries 68, 76 are prohibited from being charged while a radiographic image of the subject 14 is being captured and transmitted, the radiation detector 60 can detect radiation 16a through 16c accurately and with high quality.

The amount of electric power supplied to the batteries 68, 76 within a time zone during which the radiographic image capturing process is not carried out may be predicted as described below. The batteries 68, 76 may be charged with a predicted amount of electric power, in order to allow (a required number of) radiographic images to be captured reliably.

More specifically, amounts of electric power that are consumed by the radiation output device 20 and the radiation detecting device 22 are calculated from charging conditions for the batteries 68, 76, and from previous and present image capturing conditions (the numbers of captured radiographic images, mAs values, etc.). Amounts of electric power that are consumed by the radiation output device 20 and the radiation detecting device 22 in the present image capturing process, or amounts of electric power that are consumed by the radiation output device 20 and the radiation detecting device 22 in the previous image capturing process are predicted from the calculated amounts of electric power.

By charging the batteries 68, 76 to respective power levels, which are commensurate with amounts of electric power expected to be consumed during the present image capturing process, or with amounts of electric power consumed during the previous image capturing process, the present image capturing process can reliably be carried out.

Further, if the batteries 68, 76 are to be charged during intervals between a plurality of radiographic image capturing events, then the amounts of electric power to be consumed by the radiation output device 20 and the radiation detecting device 22 are calculated from charging conditions and image capturing conditions for radiographic images to be captured at the present time, from among the present image capturing conditions (numbers of captured radiographic images, mAs values, etc.), except for radiographic images that have already been captured, and amounts of electric power to be consumed for radiographic images to be captured at the present time are predicted based on the calculated image capturing conditions.

In this case as well, since the batteries 68, 76 are charged to a power level commensurate with the amounts of electric power to be consumed for radiographic images to be captured at the present time, any remaining radiographic images to be captured can reliably be captured.

Moreover, in the first embodiment, explanations have been made in which signals are sent and received by way of wireless communications and/or wired communications. However, if the subject 14 is held in contact with the radiation output device 20 and the radiation detecting device 22 at a short SID, then signals may be sent and received between the radiation output device 20 and the radiation detecting device 22 by way of human body communications via the subject 14. Further, if the doctor 26 is held in contact with both the radiation output device 20 and the control device 24, then signals may be sent and received between the radiation output device 20 and the control device 24 by way of human body communications via the doctor 26.

In the first embodiment, the control signal generator 154 generates an exposure control signal for synchronizing emission of radiation 16a through 16c from the radiation sources 18a through 18c and conversion of such radiation 16a through 16c into a radiographic image (the first radiographic image or the second radiographic image) by the radiation detector 60, and the communication unit 122 sends the exposure control signal to the radiation output device 20 and the radiation detecting device 22. Therefore, the radiation sources 18a through 18c and the radiation detector 60 can reliably be synchronized with each other during the radiographic image capturing process (the first image capturing process or the second image capturing process).

Further, in the first embodiment, the radiation detecting device 22 includes the rectangular housing 30. However, the radiation detecting device 22 may be in the form of a flexible sheet including at least the radiation detector 60. Since such a flexible sheet is capable of being wound into a roll, the radiation detecting device 22 in the form of a flexible sheet can be made compact.

Furthermore, the first embodiment is applicable to acquisition of radiographic images using a light-readout-type radiation detector. Such a light-readout-type radiation detector operates as follows. If radiation is applied to a matrix of solid-state detecting devices, then the solid-state detecting devices store an electrostatic latent image, which is dependent on the dose of applied radiation. For reading the stored electrostatic latent image, reading light is applied to the solid-state detecting devices in order to cause the solid-state detecting devices to generate an electric current representing radiation image information. If erasing light is applied to the radiation detector, then radiographic image information representing a residual electrostatic latent image is erased from the radiation detector, whereby the radiation detector can be reused (see Japanese Laid-Open Patent Publication No. 2000-105297).

Still further, in order to prevent the radiographic image capturing system 10A from being contaminated with blood and bacteria, the radiation output device 20 and the radiation detecting device 22 may have a water-resistant and hermetically sealed structure, and may be sterilized and cleaned as necessary so that the radiographic image capturing system 10A can be used repeatedly.

The first embodiment is not limited to capturing of radiographic images in the art of medicine, but also may be applied to the capture of radiographic images in various nondestructive tests.

[Modifications of the First Embodiment]

Modifications (first through eleventh modifications) of the first embodiment will be described below with reference to FIGS. 15A through 30.

Parts of such modifications, which are identical to those shown in FIGS. 1 through 14, are denoted by identical reference characters, and such features will not be described in detail below.

[First Modification]

Figure 15A:
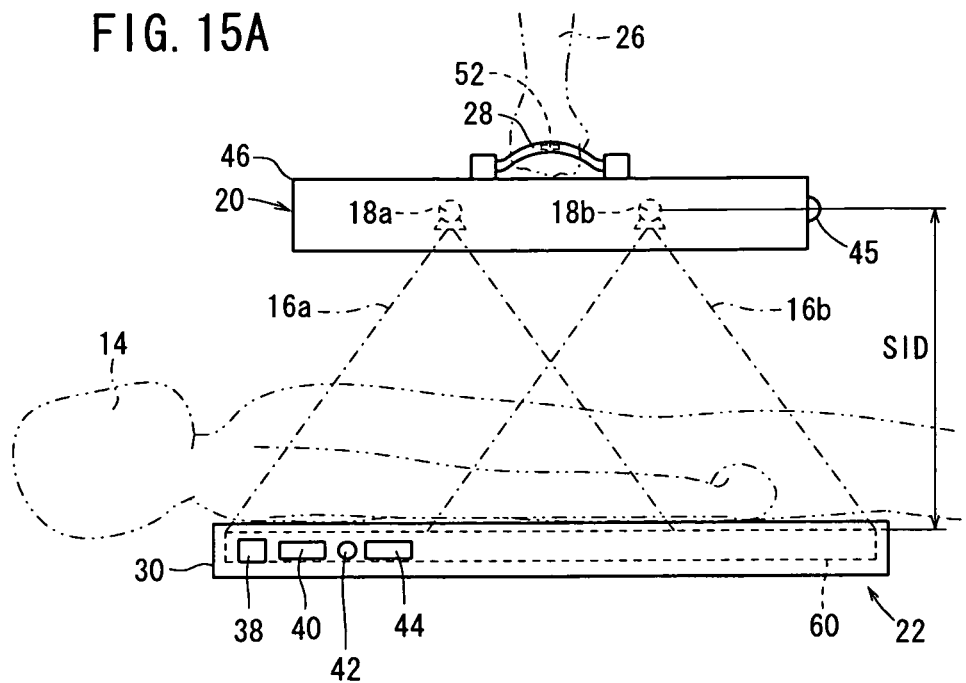
FIGS. 15A and 15B are side elevational views of a radiographic image capturing system according to a first modification.
Figure 15B:
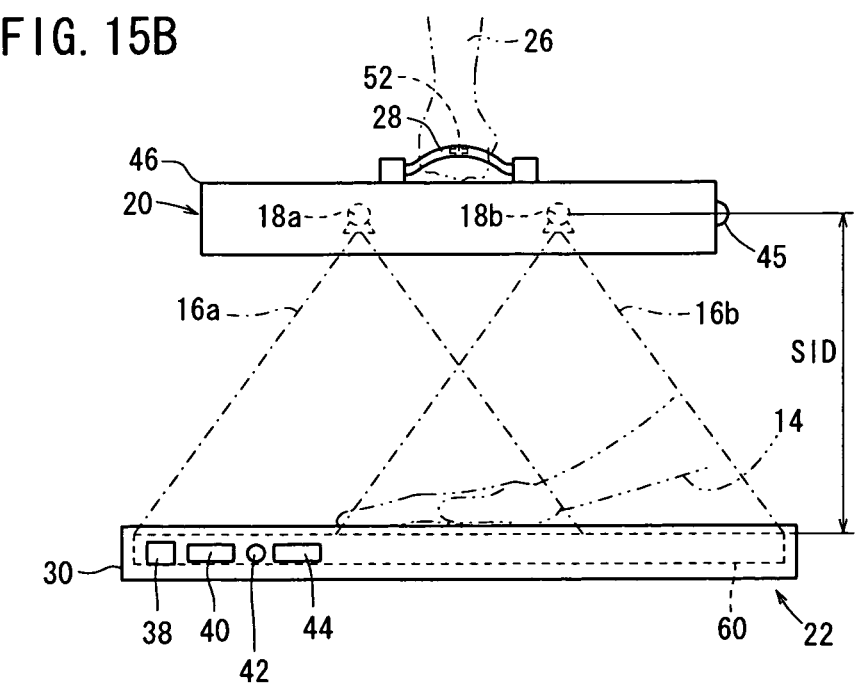

According to a first modification, as shown in FIGS. 15A and 15B, a radiation output device 20 houses two radiation sources 18a, 18b therein.

In this case, the radiation sources 18a, 18b apply radiation 16a, 16b respectively to the subject 14. During the second image capturing process, doses of radiation 16a, 16b are weighted based on the first radiographic image.

In this manner, in the case of the first modification, in which only two radiation sources 18a, 18b are housed in the radiation output device 20, by performing the aforementioned first image capturing process to acquire the first radiographic image, the same advantages as those of the first embodiment can be obtained.

As described above, according to the first embodiment and the first modification thereof, a first radiographic image is acquired, and doses of radiation emitted from two radiation sources 18a, 18b or three radiation sources 18a, 18b, 18c are weighted. However, the first radiographic image may be acquired, and doses of radiation emitted from four or more radiation sources may be weighted based on the principles of the first embodiment and the first modification thereof, thereby offering the same advantages as those of the first embodiment and the first modification.

[Second Modification]

Figure 16A:
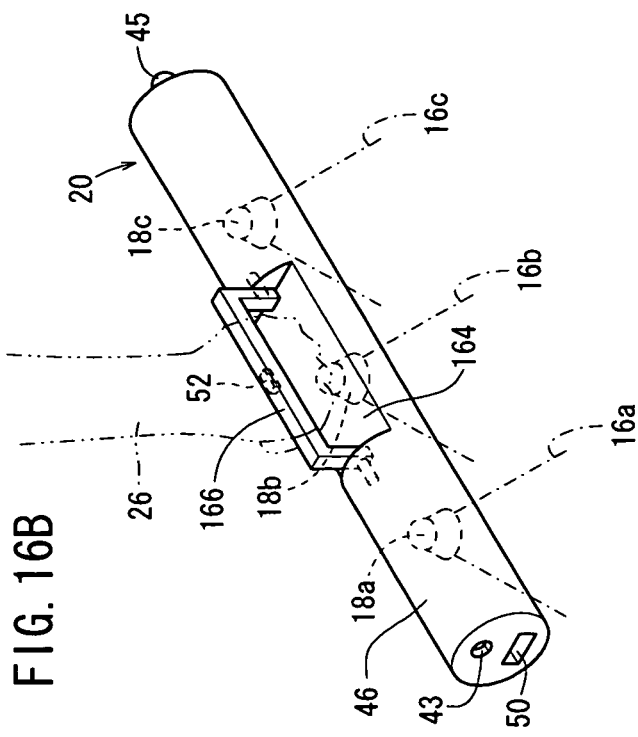
FIGS. 16A and 16B are perspective views of a radiographic image capturing system according to a second modification.
Figure 16B:
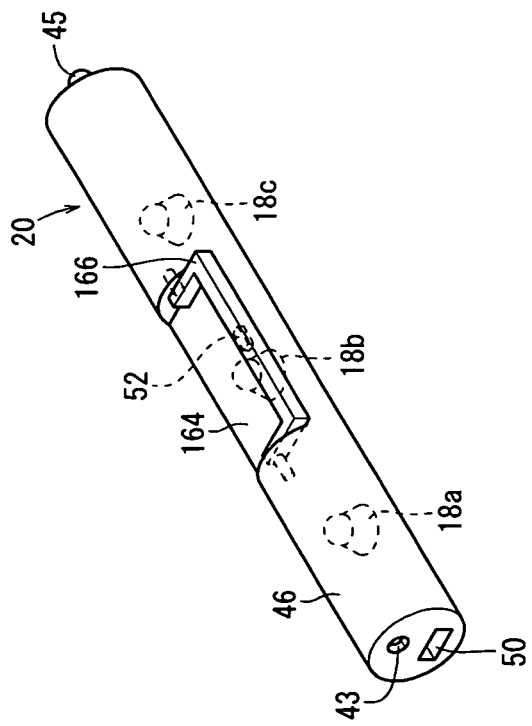

According to a second modification, as shown in FIGS. 16A and 16B, a casing 46 of the radiation output device 20 includes a recess 164 defined in a side thereof remote from the side at which radiation 16a through 16c is emitted from the radiation sources 18a through 18c. A collapsible grip 166 is pivotally movably disposed for storage in the recess 164. A touch sensor 52 is incorporated in the grip 166.

In the case that the doctor 26 is not carrying the radiation output device 20, the grip 166 is accommodated flatwise in the recess 164, as shown in FIG. 16A. If the doctor 26 turns the grip 166 about the pivoted end, then the grip 166 is raised out from the recess 164, so that the doctor 26 can grip the grip 166 (see FIG. 16B). The grip 166 and the touch sensor 52 offer the same advantages as those of the grip 28 and the touch sensor 52 according to the first embodiment. Further, in a case where the grip 166 is turned about the pivoted end back into the recess 164, the grip 166 is placed flatwise in the recess 164, thereby keeping the electrodes of the touch sensor 52 out of contact with the hand of the doctor 26. Therefore, the radiation output device 20 is prevented from being activated, and hence the radiation sources 18a through 18c are prevented from emitting radiation 16a through 16c in error.

[Third Modification]

Figure 17A:
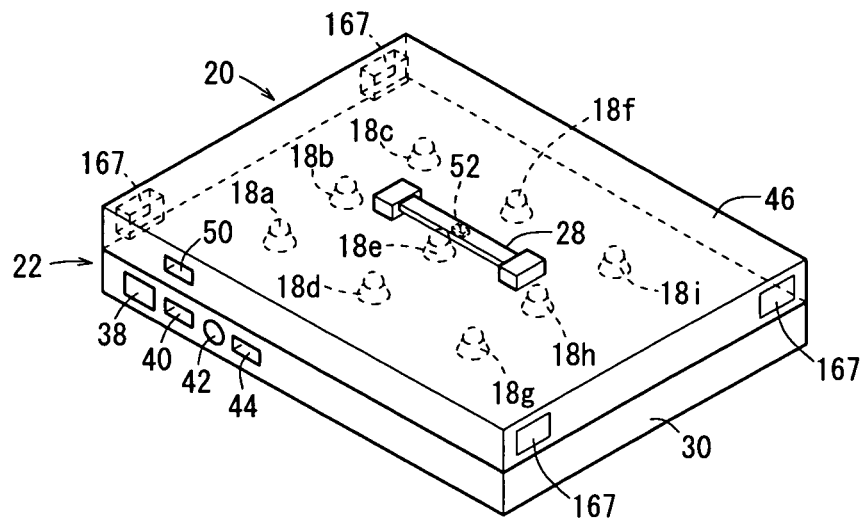
FIGS. 17A and 17B are perspective views of a radiographic image capturing system according to a third modification.
Figure 17B:
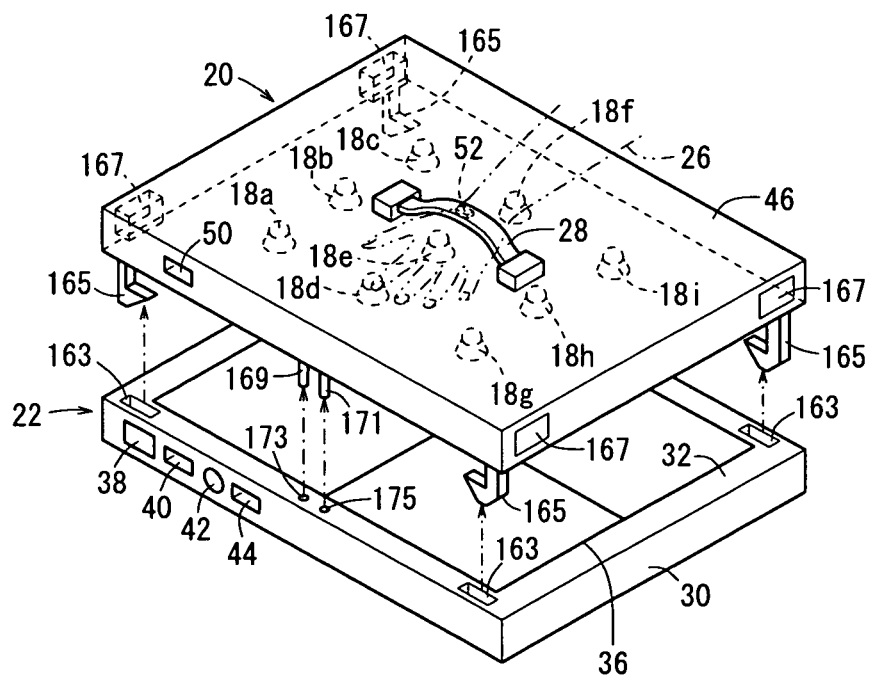

According to a third modification, as shown in FIGS. 17A and 17B, the casing 46 of the radiation output device 20 is of a rectangular shape, the planar area of which is substantially the same as the radiation detecting device 22. The casing 46 houses therein nine radiation sources 18a through 18i. The casing 46 is not required to house all nine of the radiation sources 18a through 18i, but may house at least three radiation sources.

The radiation sources 18a through 18i are arranged in a two-dimensional matrix facing toward the irradiated surface 32, which differs from the above-described linear array of radiation sources 18a through 18c that face toward the irradiated surface 32 (see FIGS. 1, 5A through 6B, 15A and 15B).

Further, the casing 46 has a grip 28 disposed on an upper surface thereof, and also has unlocking buttons 167 on opposite side surfaces thereof for releasing hooks 165, which are mounted on the bottom surface of the casing 46, from openings 163 that are defined respectively in four corners on the upper surface of the housing 30 of the radiation detecting device 22.

Furthermore, the housing 30 has connection terminals 173, 175 disposed on the upper surface thereof outside of the imaging area 36, which serve as jacks, which are capable of interfitting engagement with respective pin-shaped connection terminals 169, 171 mounted on the bottom surface of the casing 46.

In the condition shown in FIG. 17A, the hooks 165 engage respectively in the openings 163, and the connection terminals 169, 171 are held in interfitting engagement respectively with the connection terminals 173, 175, thereby holding the radiation output device 20 and the radiation detecting device 22 integrally with each other. Owing thereto, the doctor 26 can grip the grip 28, or insert his or her hand between the grip 28 and the upper surface of the casing 46, in order to carry the radiation output device 20 and the radiation detecting device 22, which are integrally combined with each other. Further, in such an integrated condition, the battery 76 of the radiation detecting device 22 (see FIG. 7) is capable of charging the battery 68 of the radiation output device 20 via the connection terminals 169, 171, 173, 175.

On the other hand, if the doctor 26 presses the unlocking buttons 167 in order to release the hooks 165 from the respective openings 163, and grips the grip 28 or inserts his or her hand between the grip 28 and the upper surface of the casing 46 so as to separate (lift) the radiation output device 20 from the radiation detecting device 22, then the connection terminals 169, 171 are released from the connection terminals 173, 175, whereby the integrated state between the radiation output device 20 and the radiation detecting device 22 is released. As a result thereof, the battery 76 stops charging the battery 68, and the radiation sources 18a through 18i are made capable of emitting radiation respectively.

According to the third modification, since the radiation sources 18a through 18i are arranged in a two-dimensional matrix, radiographic images of any regions to be imaged of the subject 14 can be captured efficiently. Further, as the casing 46 of the radiation output device 20 is essentially of the same rectangular shape as the housing 30 of the radiation detecting device 22, the radiation output device 20 and the radiation detecting device 22, which are integrally combined with each other, are rendered highly portable, and the radiation output device 20 can easily be positioned with respect to the radiation detecting device 22.

The third modification thus offers the same advantages as those of the first embodiment, as well as the first and second modifications.

[Fourth Modification]

In the above explanation, the photoelectric conversion layer 96, which serves as one of the components of the radiation detector 60, is made of amorphous silicon (a-Si) or the like. However, according to the first embodiment, the photoelectric conversion layer may include an organic photoelectric conversion material.

A radiation detector including a photoelectric conversion layer, which includes an organic photoelectric conversion material according to a fourth modification, will be described below with reference to FIGS. 18 and 19.

Figure 18:
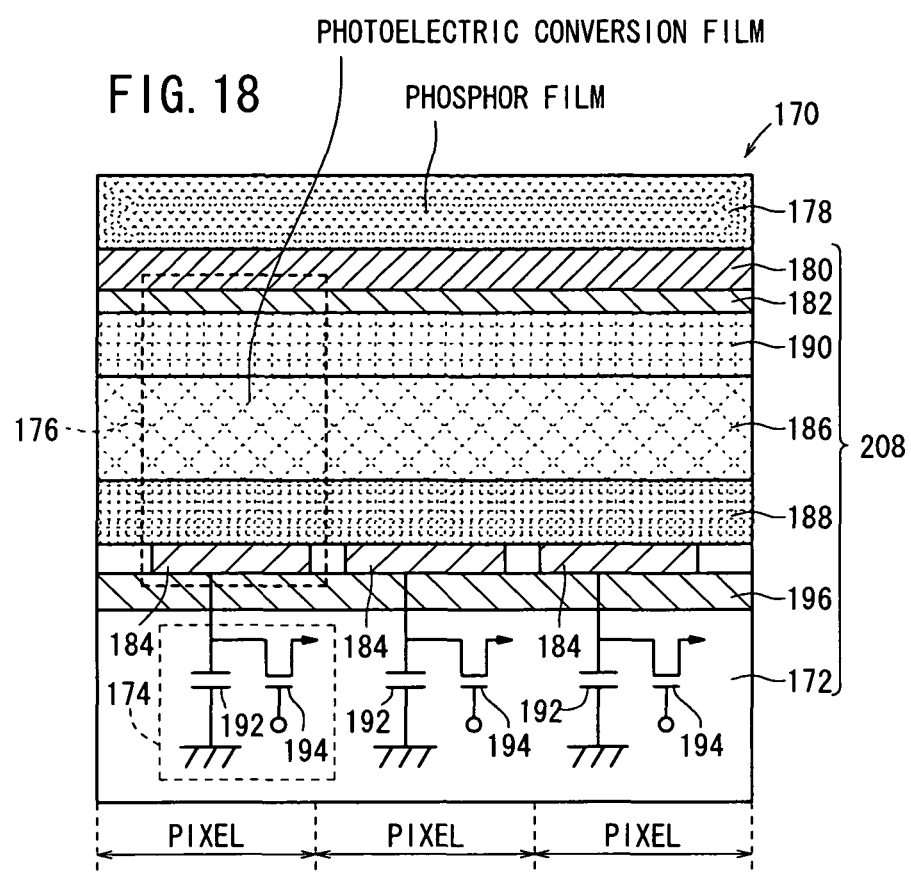
FIG. 18 is a cross sectional view showing a radiographic image capturing system according to a fourth modification.

As shown in FIG. 18, a radiation detector 170 includes a signal output section 174, a sensor 176, and a scintillator 178, which are successively deposited on an insulating substrate 172. The signal output section 174 and the sensor 176 jointly make up a pixel. The radiation detector 170 includes a matrix of pixels arrayed on the substrate 172. In each of the pixels, the signal output section 174 is superposed on the sensor 176.

Figure 19:
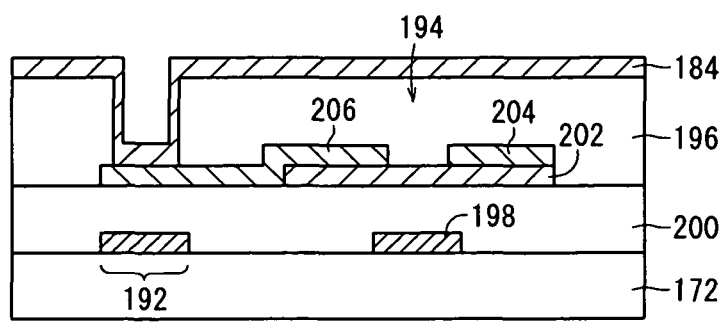
FIG. 19 is a cross sectional view showing in outline the structure of a signal output section of one pixel of a radiation detector of FIG. 18.

More specifically, the radiation detector 170 shown in FIGS. 18 and 19 is a rear surface reading type, i.e., a penetration side sample (PSS) type, of radiation detector, in which the scintillator 178, the sensor 176 and the signal output section 174 are arranged in this order along the direction in which radiation 16a through 16c is applied. Explanations concerning a front surface reading type, i.e., an irradiation side sampling (ISS) type, of radiation detector, in which the signal output section 174, the sensor 176 and the scintillator 178 are arranged in this order along the direction in which radiation 16a through 16c is applied, shall be given subsequently.

The scintillator 178 is disposed over the sensor 176 with a transparent insulating film 180 interposed therebetween. The scintillator 178 is in the form of a film made of phosphor, for emitting light converted from radiation 16a through 16c (see FIGS. 1, 4B through 7, 15A, 15B and 16B) that is applied from above, at a location remote from the substrate 172. The scintillator 178 can absorb radiation 16a through 16c that has passed through the subject 14 and emit light converted therefrom.

Light emitted by the scintillator 178 should preferably have a visible wavelength range from 360 nm to 830 nm. If the radiation detector 170 is used to capture a monochromatic image, then light emitted by the scintillator 178 should preferably include a green wavelength range.

If X-rays are used as the radiation 16a through 16c, then the phosphor used in the scintillator 178 should preferably include cesium iodide (CsI), and particularly preferably, should include CsI(Tl) (thallium-added cesium iodide) which, when irradiated with X-rays, emits light in a wavelength spectrum ranging from 420 nm to 700 nm. Light emitted from CsI(Tl) has a peak wavelength of 565 nm in the visible range. Further, such a phosphor is not limited to CsI (Tl), and other materials such as CsI(Na) (sodium-activated cesium iodide) or GOS ($Gd_2O_2S$:Tb) may also be used.

The sensor 176 includes an upper electrode 182, a lower electrode 184, and a photoelectric conversion film 186 disposed between the upper electrode 182 and the lower electrode 184. The photoelectric conversion film 186 is made of an organic photoelectric conversion material for generating electric charges by absorbing light emitted by the scintillator 178.

Since the light emitted by the scintillator 178 must be applied to the photoelectric conversion film 186, the upper electrode 182 should preferably be made of an electrically conductive material, which is transparent to at least the wavelength of the light emitted by the scintillator 178. More specifically, the upper electrode 182 should preferably be made of a transparent conducting oxide (TCO), which is of a high transmittance with respect to visible light and has a small resistance value. Although the upper electrode 182 may be made of a thin metal film such as of Au or the like, TCO is preferable thereto because Au tends to have an increased resistance value at transmittances of 90% or higher. For example, ITO (Indium Tin Oxide), IZO (Indium Zinc Oxide), AZO (Aluminum doped Zinc Oxide), FTO (Fluorine doped Tin Oxide), $SnO_2$, $TiO_2$, $ZnO_2$, or the like should preferably be used as the material of the upper electrode 182. Among these materials, ITO is the most preferable from the standpoints of process simplification, low resistance, and transparency. The upper electrode 182 may be a single electrode shared by all of the pixels, or may be a plurality of electrodes assigned to respective pixels.

The photoelectric conversion film 186 may be made of a material that absorbs visible light and generates electrical charges, and may utilize the aforementioned amorphous silicon (a-Si) or an organic photoelectric conversion (OPC) material, which absorbs light emitted by the scintillator 178 and generates electric charges depending on the absorbed light.

In the case that the photoelectric conversion film 186 is constituted by amorphous silicon, a structure can be provided so as to absorb over a wide wavelength range visible light that is emitted from the scintillator 178. However, vapor deposition must be carried out in order to form the photoelectric conversion film 186 from amorphous silicon, and in the event that the substrate 172 is a synthetic resin, special consideration must be given to heat resistance of the substrate 172.

On the other hand, in the case that a photoelectric conversion film 186 including an organic photoelectric conversion material is used, the photoelectric conversion film 186 has a sharp absorption spectrum in the visible range and does not absorb electromagnetic waves other than light emitted by the scintillator 178. Therefore, any noise, which would be produced if radiation 16a through 16c such as X-rays were absorbed by the photoelectric conversion film 186, is effectively minimized.

Further, since a photoelectric conversion film 186 made from an organic photoelectric conversion material can be formed using a liquid droplet discharge head such as an inkjet head or the like, in which the organic photoelectric conversion material is made to adhere to a formed body, it is not necessary that the formed body be resistant to heat.

In order for the organic photoelectric conversion material of the photoelectric conversion film 186 to absorb light emitted by the scintillator 178 most efficiently, the absorption peak wavelength thereof should preferably be as close as possible to the light emission peak wavelength of the scintillator 178. Although the absorption peak wavelength of the organic photoelectric conversion material and the light emission peak wavelength of the scintillator 178 should ideally be in agreement with each other, it is possible to sufficiently absorb light emitted by the scintillator 178 if the difference between the absorption peak wavelength and the light emission peak wavelength is sufficiently small. More specifically, the difference between the absorption peak wavelength of the organic photoelectric conversion material and the light emission peak wavelength of the scintillator 178 with respect to the radiation 16a through 16c should preferably be 10 nm or smaller, and more preferably, 5 nm or smaller.

Organic photoelectric conversion materials that meet the above requirements include quinacridone-based organic compounds and phthalocyanine-based organic compounds. Since quinacridone has an absorption peak wavelength of 560 nm in the visible range, if quinacridone is used as the organic photoelectric conversion material and CsI(Tl) as the material of the scintillator 178, the difference between the above peak wavelengths can be reduced to 5 nm or smaller, thus making it possible to substantially maximize the amount of electric charges generated by the photoelectric conversion film 186.

The photoelectric conversion film 186, which is applicable to the radiation detector 170, will be described in specific detail below.

The radiation detector 170 includes an electromagnetic wave absorption/photoelectric conversion region, which is provided by an organic layer including the electrodes 182, 184 and the photoelectric conversion film 186 sandwiched between the electrodes 182, 184. The organic layer may be formed by the superposition or mixture of an electromagnetic wave absorption region, a photoelectric conversion region, an electron transport region, a hole transport region, an electron blocking region, a hole blocking region, a crystallization preventing region, an electrode, and an interlayer contact improving region, etc.

The organic layer should preferably include an organic p-type compound or an organic n-type compound.

An organic p-type semiconductor (compound) is a donor organic compound mainly typified by a hole transport organic compound, and refers to an organic compound that tends to donate electrons. More specifically, in a case where two organic materials are used in contact with each other, one of the organic materials, which has a lower ionization potential, is referred to as a donor organic compound. Any organic compounds that are capable of donating electrons can be used as the donor organic compound.

An organic n-type semiconductor (compound) is an acceptor organic compound mainly typified by an electron transport organic compound, and refers to an organic compound that tends to accept electrons. More specifically, in a case where two organic materials are used in contact with each other, one of the organic materials, which has a larger electron affinity, is referred to as an acceptor organic compound. Any organic compounds that are capable of accepting electrons can be used as the acceptor organic compound.

Materials that can be used as the organic p-type semiconductor and the organic n-type semiconductor, and arrangements of the photoelectric conversion film 186 are disclosed in detail in Japanese Laid-Open Patent Publication No. 2009-032854, and such features will not be described in detail below.

The sensor 176 of each pixel may include at least the lower electrode 184, the photoelectric conversion film 186, and the upper electrode 182. For preventing an increase in dark current, the sensor 176 should preferably additionally include either an electron blocking film 188 or a hole blocking film 190, and more preferably, should include both the electron blocking film 188 and the hole blocking film 190.

The electron blocking film 188 may be disposed between the lower electrode 184 and the photoelectric conversion film 186. In a case where a bias voltage is applied between the lower electrode 184 and the upper electrode 182, the electron blocking film 188 is capable of preventing electrons from being injected from the lower electrode 184 into the photoelectric conversion film 186, thereby preventing dark current from increasing.

The electron blocking film 188 may be made of an organic material capable of donating electrons.

The electron blocking film 188 is actually made of a material that is selected depending on the material of the lower electrode 184 and the material of the photoelectric conversion film 186, which lie adjacent thereto. Preferably, the material should have an electron affinity (Ea) that is at least 1.3 eV greater than the work function (Wf) of the material of the adjacent lower electrode 184, and an ionization potential (Ip) that is equal to or smaller than the Ip of the material of the adjacent photoelectric conversion film 186. Materials that can be used as an organic material, and which are capable of donating electrons, are disclosed in detail in Japanese Laid-Open Patent Publication No. 2009-032854, and such materials will not be described in detail below.

The thickness of the electron blocking film 188 should preferably be in a range from 10 nm to 200 nm, more preferably in a range from 30 nm to 150 nm, and particularly preferably in a range from 50 nm to 100 nm, in order to reliably achieve a dark current reducing capability, and to prevent the photoelectric conversion efficiency of the sensor 176 from being lowered.

The hole blocking film 190 may be disposed between the photoelectric conversion film 186 and the upper electrode 182. In a case where a bias voltage is applied between the lower electrode 184 and the upper electrode 182, the hole blocking film 190 is capable of preventing holes from being injected from the upper electrode 182 into the photoelectric conversion film 186, thereby preventing dark current from increasing.

The hole blocking film 190 may be made of an organic material, which is capable of accepting electrons.

The thickness of the hole blocking film 190 should preferably be in a range from 10 nm to 200 nm, more preferably in a range from 30 nm to 150 nm, and particularly preferably in a range from 50 nm to 100 nm, in order to reliably achieve a dark current reducing capability, and to prevent the photoelectric conversion efficiency of the sensor 176 from being lowered.

The hole blocking film 190 is actually made of a material that is selected depending on the material of the upper electrode 182 and the material of the photoelectric conversion film 186 that lie adjacent thereto. A preferable material should have an ionization potential (Ip) that is at least 1.3 eV greater than the work function (Wf) of the material of the adjacent upper electrode 182, and an electron affinity (Ea) equal to or greater than the Ea of the material of the adjacent photoelectric conversion film 186. Materials that can be used as organic materials capable of accepting electrons are disclosed in detail in Japanese Laid-Open Patent Publication No. 2009-032854, and such materials will not be described in detail below.

In order to set a bias voltage to move holes, from among the electric charges generated in the photoelectric conversion film 186, toward the upper electrode 182, and to move electrons, from among the electric charges generated in the photoelectric conversion film 186, toward the lower electrode 184, the electron blocking film 188 and the hole blocking film 190 may be switched in position. The electron blocking film 188 and the hole blocking film 190 are not both required, but rather, either one of the electron blocking film 188 and the hole blocking film 190 may be included so as to provide a certain dark current reducing capability.

The signal output section 174 is formed on the surface of the substrate 172 beneath the lower electrode 184 of each pixel. FIG. 19 schematically shows structural details of the signal output section 174.

The signal output section 174 includes a capacitor 192, which is aligned with the lower electrode 184, for storing electric charges that have moved to the lower electrode 184, and a field-effect thin film transistor (hereinafter also referred to simply as a "thin film transistor" or TFT) 194 for converting the electric charges stored in the capacitor 192 into electric signals, and outputting the electric signals. The capacitor 192 and the thin film transistor 194 are disposed in a region underlapping the lower electrode 184 as viewed in plan. This structure enables the signal output section 174 and the sensor 176 to be superposed in each pixel in the thickness direction. In order to minimize the planar area of the radiation detector 170 (pixels), it is desirable for the region in which the capacitor 192 and the thin film transistor 194 are disposed to be fully covered with the lower electrode 184.

The capacitor 192 is electrically connected to the lower electrode 184 by an electrically conductive interconnection, which extends through an insulating film 196 interposed between the substrate 172 and the lower electrode 184. The interconnection allows electric charges collected by the lower electrode 184 to migrate toward the capacitor 192.

As shown in FIG. 19, the thin film transistor 194 includes a stacked assembly made up of a gate electrode 198, a gate insulating film 200, and an active layer (channel layer) 202, and a source electrode 204 and a drain electrode 206 disposed on the active layer 202 and spaced from each other with a gap therebetween. In the radiation detector 170, although the active layer 202 may be formed by any of amorphous silicon, an amorphous oxide, an organic semiconductor material, carbon nanotubes or the like, materials capable of forming the active layers are not limited to the foregoing materials.

As an amorphous oxide that constitutes the active layer 202, such an amorphous oxide should preferably be an oxide (e.g., In—O oxide) including at least one of In, Ga, and Zn, more preferably, an oxide (e.g., In—Zn—O oxide, In—Ga—O oxide, or Ga—Zn—O oxide) including at least two of In, Ga, and Zn, and particularly preferably, an oxide including In, Ga, and Zn. An In—Ga-An-O amorphous oxide should preferably be an amorphous oxide, the crystalline composition of which is represented by $InGaO_3 (ZnO)_m$ where m represents a natural number smaller than 6, and more particularly, preferably should be $InGaZnO_4$. However, amorphous oxides capable of forming the active layer 202 are not limited to the foregoing.

Further, as organic semiconductor materials capable of forming the active layer 202, for example, there may be used phthalocyanine compounds, pentacene, vanadyl phthalocyanine or the like, although the present invention is not limited to such materials. Concerning phthalocyanine compounds, details thereof are described in detail in Japanese Laid-Open Patent Publication No. 2009-212389, and detailed explanations of such compounds are omitted.

If the active layer 202 of the thin film transistor 194 is made from any of an amorphous oxide, an organic semiconductor material, carbon nanotubes or the like, then since the active layer 202 does not absorb radiation 16a through 16c such as X-rays or the like, or absorbs only an extremely small amount of radiation 16a through 16c, the active layer 202 is effective to reduce noise generated in the signal output section 174.

Further, if the active layer 202 is formed from carbon nanotubes, the switching speed of the thin film transistor 194 can be increased, and absorption of light in the visible light band in the thin film transistor 194 can be lessened. Moreover, if the active layer 202 is formed from carbon nanotubes, because performance of the thin film transistor 194 is lowered remarkably as a result of being mixed with only extremely small amounts of metallic impurities, it is necessary to form the active layer 202 by separating and extracting carbon nanotubes, which are extremely high in purity, by means of centrifugal separation or the like.

Further, because films formed from organic photoelectric conversion materials and films formed from organic semiconductor materials possess sufficient flexibility, if a structure is constituted by a combination of a photoelectric conversion film 186 formed from an organic photoelectric conversion material and a thin film transistor 194 in which the active layer 202 thereof is formed from an organic semiconductor material, it becomes unnecessary for the TFT substrate 208 to have high rigidity to accommodate as a load the weight of the body of the subject 14.

The amorphous oxide of the active layer 202 of the thin film transistor 194, and the organic photoelectric conversion material of the photoelectric conversion film 186 can be deposited as films at low temperatures. Therefore, the substrate 172 is not limited to a highly heat-resistant substrate, such as a semiconductor substrate, a quartz substrate, a glass substrate, or the like, but may be a flexible substrate made of plastic, a substrate of aramid fibers, or a substrate of bionanofibers. More specifically, the substrate 172 may be a flexible substrate of polyester, such as polyethylene terephthalate, polybutylene phthalate, polyethylene naphthalate, or the like, polystyrene, polycarbonate, polyethersulfone, polyarylate, polyimide, polycycloolefine, norbornene resin, poly(chlorotrifluoro-ethylene), or the like. A flexible substrate fabricated from plastic makes the radiation detector 170 light in weight and hence easier to carry.

The substrate 172 may include an insulating layer for thereby making the substrate 172 electrically insulative, a gas barrier layer for making the substrate 172 impermeable to water and oxygen, and an undercoat layer for making the substrate 172 flat or improving intimate contact between the substrate 172 and the electrode.

Aramid fibers for use as the substrate 172 are advantageous in that, since a high-temperature process at 200° C. is applicable thereto, aramid fibers allow a transparent electrode material to be set at a high temperature for lower resistance, and also allow driver ICs to be automatically mounted thereon by a process including a solder reflow process. Furthermore, since aramid fibers have a coefficient of thermal expansion that is close to ITO (Indium Tin Oxide) and glass, an insulating substrate made of aramid fibers is less likely to suffer from warpage and cracking after fabrication thereof. In addition, an insulating substrate made of aramid fibers may be fabricated thinner than a glass substrate or the like. The substrate 172 may be in the form of a stacked assembly of an ultrathin glass substrate and aramid fibers.

Bionanofibers are made by compounding a bundle of cellulose microfibrils (bacteria cellulose) produced by bacteria (acetic acid bacteria, *Acetobacter xylinum*) and a transparent resin. The bundle of cellulose microfibrils has a width of 50 nm, which is 1/10 of the wavelength of visible light, is highly strong and highly resilient, and is subject to low thermal expansion. Bionanofibers, which contain 60% to 70% fibers and exhibit a light transmittance of about 90% at a wavelength of 500 nm, can be produced by impregnating bacteria cellulose with a transparent resin such as an acrylic resin, an epoxy rein, or the like, and setting the transparent resin. Bionanofibers are flexible, and have a low coefficient of thermal expansion ranging from 3 ppm to 7 ppm, which is comparable to silicon crystals, a high strength of 460 MPa that matches the strength of steel, and a high resiliency of 30 GPa. Therefore, an insulating substrate 172, which is made of bionanofibers, can be thinner than glass substrates or the like.

Since the photoelectric conversion film 186 of the radiation detector 170 is made of an organic photoelectric conversion material, the photoelectric conversion film 186 absorbs almost none of the radiation 16a through 16c. Therefore, in a PSS type of radiation detector 170, even if the radiation 16a through 16c passes through a TFT substrate 208, since the photoelectric conversion film 186 absorbs only a small amount of radiation 16a through 16c, any reduction in sensitivity to the radiation 16a through 16c is minimized. With a PSS type of radiation detector 170, radiation 16a through 16c passes through the TFT substrate 208 and reaches the scintillator 178. However, since the photoelectric conversion film 186 of the TFT substrate 208 is made of an organic photoelectric conversion material, the photoelectric conversion film 186 essentially does not absorb radiation 16a through 16c, and any attenuation in radiation 16a through 16c is minimized. Therefore, a photoelectric conversion film 186, which is made of an organic photoelectric conversion material, is suitable for use in a PSS type radiation detector.

The amorphous oxide of the active layer 202 of the thin film transistor 194 and the organic photoelectric conversion material of the photoelectric conversion film 186 can be deposited as films at low temperatures. Therefore, the substrate 172 may be made of plastic, aramid fibers, or bionanofibers, which absorb only small amounts of radiation 16a through 16c. Since the substrate 172 thus made of plastic, aramid fibers, or bionanofibers absorbs only a small amount of radiation 16a through 16c, the substrate 172 is effective to prevent sensitivity to radiation 16a through 16c from being lowered, even if radiation 16a through 16c passes through the TFT substrate 208 due to being used in a PSS type radiation detector.

According to the fourth modification, the radiation detector 170 may be constituted in the following manner.

(1) The sensor 176 including the photoelectric conversion film 186 made of an organic photoelectric conversion material may be constructed so as to constitute the signal output section 174 using a CMOS sensor. In this case, since only the sensor 176 is made up from an organic photoelectric conversion material, the signal output section 174 including the CMOS sensor does not need to be flexible. Concerning the sensor 176, which is constructed to include an organic photoelectric conversion material, as well as the CMOS sensor, details thereof have been described in Japanese Laid-Open Patent Publication No. 2009-212377, and thus detailed explanations of such features are omitted.

(2) The sensor 176 including the photoelectric conversion film 186 made of an organic photoelectric conversion material may be constructed so as to realize the signal output section 174, which possesses flexibility, by a CMOS circuit equipped with a thin film transistor (TFT) 194 made up from an organic material. In this case, pentacene may be adopted as a material of a p-type organic semiconductor, and fluorinated copper phthalocyanine ($F_{16}CuPc$) may be adopted as an n-type organic semiconductor used by the CMOS circuit. In accordance therewith, a TFT substrate 208 having a certain flexibility with a smaller radius of curvature can be realized.

Further, by constructing the TFT substrate 208 in this manner, the gate insulating film 200 can be made quite thin, thus enabling the drive voltage to be lowered. Furthermore, the gate insulating film 200, the semiconductor body, and each of the electrodes can be manufactured at room temperature or at a temperature of 100° C. or less. Still further, the CMOS circuit may be manufactured directly on such a flexible insulating substrate 172. Additionally, the thin film transistor 194 made from an organic material can be miniaturized by a manufacturing process in accordance with scaling rules. For the substrate 172, if a polyimide precursor is coated on a polyimide substrate and heated using a spin coat method, because the polyimide precursor is converted into a polyimide, a flat substrate free of concave-convex irregularities can be realized.

(3) A self-assembly technique (fluidic self-assembly method) in which a plurality of micron-order device blocks are arranged in specified positions on a substrate may be applied, and the sensor 176 and the signal output section 174 may be arranged on an insulating substrate 172 made up from a resin substrate. In this case, the sensor 176 and the signal output section 174, which are micron-order miniature device blocks, are manufactured on another substrate and thereafter are separated from the substrate. Then, the sensor 176 and the signal output section 174 are dispersed in a liquid and arranged statistically on the substrate 172, which serves as a target substrate. A process may be implemented on the substrate 172 in advance for adapting the substrate 172 to the device blocks, and the device blocks can be selectively arranged on the substrate 172. Accordingly, optimum device blocks (i.e., the sensor 176 and the signal output section 174) made up from optimal materials can be integrated on an optimal substrate (insulating substrate 172), and the sensor 176 and the signal output section 174 can be integrated on a non-crystalline insulating substrate 172 (resin substrate).

[Fifth Modification]

Figure 20A:
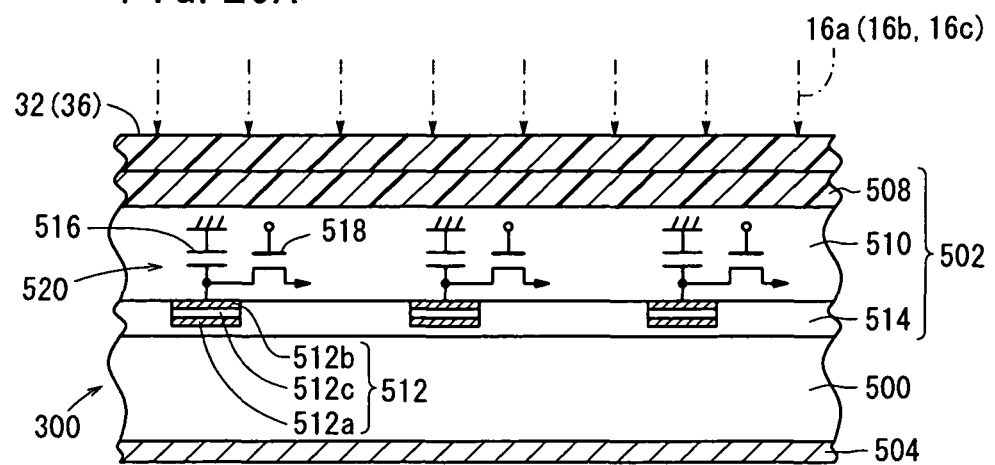
FIG. 20A is an outline explanatory diagram showing schematically an example of a radiographic image capturing system according to a fifth modification.

Next, as a fifth modification of the present invention, an example of an irradiation side sampling (ISS) type of radiation detector 300 including a CsI(Tl) scintillator 500 shall be described with reference to FIGS. 20A and 20B.

The radiation detector 300 comprises an ISS type radiation detector, in which a radiation detecting unit 502, which offers substantially the same functions as the TFT substrate 208 including the signal output section 174 and the sensor 176, and a CsI(Tl) scintillator 500 are arranged in this order with respect to an irradiated surface 32, which is irradiated with radiation 16a through 16c (i.e., along a direction in which radiation 16a through 16c is applied).

In the scintillator 500, the irradiated surface 32 side that is irradiated with radiation 16a through 16c generates and emits light more intensively. In this case, because the radiation detecting unit 502 and the scintillator 500 are arranged in a state of close proximity, compared to a PSS type, an ISS type of radiation detector has a higher ability to resolve the radiographic image, which is obtained through image capturing. Further, the emitted amount of visible light by the radiation detecting unit 502 is increased. Accordingly, more so than a PSS type, an ISS type of radiation detector can enhance the sensitivity of the radiation detector 300 (radiation detecting device 22).

Figure 20B:
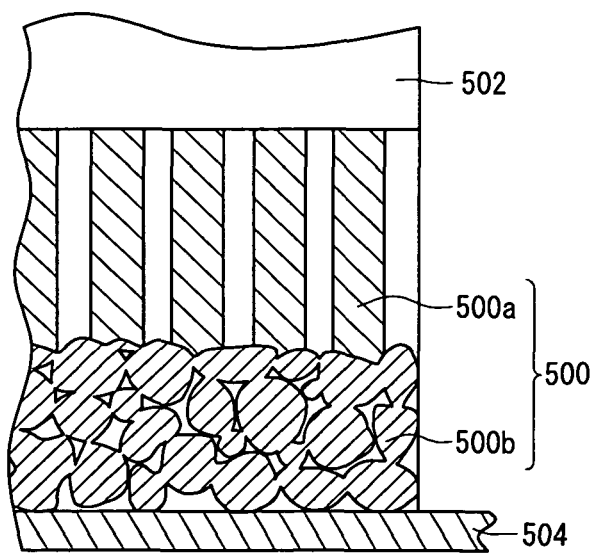
FIG. 20B is an outline explanatory diagram showing an example of a scintillator illustrated in FIG. 20A.

As one example thereof, FIG. 20B shows a case in which a scintillator 500 including a columnar crystalline domain is formed by vapor depositing a material including CsI on a vapor deposition substrate 504.

More specifically, in the scintillator 500 of FIG. 20B, a structure is provided in which a columnar crystalline domain is formed from columnar crystals 500a on the side of the irradiated surface 32 (side of the radiation detecting unit 502), which is irradiated with radiation 16a through 16c, and a non-columnar crystalline domain is formed from non-columnar crystals 500b on a side opposite from the irradiated surface 32. A material of high heat resistance preferably is used as the vapor deposition substrate 504. For example, from the standpoint of lowering costs, aluminum (Al) is preferable. Further, in the scintillator 500, the average diameter of the columnar crystals 500a is substantially uniform over the longitudinal dimension of the columnar crystals 500a.

In the above manner, the scintillator 500 is a structure that is formed by a columnar crystalline domain (columnar crystals 500a) and a non-columnar crystalline domain (non-columnar crystals 500b), and together therewith, the columnar crystalline domain, which is made up from columnar crystals 500a from which light is emitted with high efficiency, are arranged on the side of the radiation detecting unit 502. Owing thereto, visible light emitted by the scintillator 500 progresses within the columnar crystals 500a and is irradiated toward the radiation detecting unit 502. As a result, dispersion of visible light, which is irradiated toward the side of the radiation detecting unit 502, is suppressed, and blurring of the radiographic image, which is detected by the radiation detecting device 22, also is suppressed. Further, since the visible light that reaches the deep portion (i.e., the non-columnar crystalline domain) of the scintillator 500 also is reflected toward the side of the radiation detecting unit 502 by the non-columnar crystals 500b, the emitted amount of visible light incident on the radiation detecting unit 502 (and the detection efficiency of visible light emitted by the scintillator 500) can be enhanced.

If the thickness of the columnar crystalline domain positioned on the side of the irradiated surface 32 of the scintillator 500 is set at t1, and the thickness of the non-columnar crystalline domain positioned on the side of the vapor deposition substrate 504 of the scintillator 500 is set at t2, then preferably, between t1 and t2, the relationship $0.01 \leq (t2/t1) \leq 0.25$ is satisfied.

In this manner, by satisfying the foregoing relationship between the thickness t1 of the columnar crystalline domain and the thickness t2 of the non-columnar crystalline domain, the ratio along the thickness direction of the scintillator 500 between a domain (columnar crystalline domain) of high light emission efficiency for preventing diffusion of visible light and a domain (non-columnar crystalline domain) for reflecting visible light lies within a suitable range, whereby the light emission efficiency of the scintillator 500, the detection efficiency of visible light emitted by the scintillator 500, and the resolution of the radiographic image are improved.

If the thickness t2 of the non-columnar crystalline domain is excessive, a domain is increased in which the light emission efficiency is low, and the sensitivity of the radiation detecting device 22 also is lowered. Therefore, a range in which the quantity t2/t1 is greater than or equal to 0.02 and less than or equal to 0.1 is particularly preferable.

Further, an explanation has been given above concerning a scintillator 500 having a structure in which the columnar crystalline domain and the non-columnar crystalline domain are formed continuously. However, a structure may be provided in which, in place of the aforementioned non-columnar crystalline domain, a light reflective layer is formed from aluminum (Al) or the like, and only the columnar crystalline domain is formed. Other structures apart therefrom may also be provided.

The radiation detecting unit 502 serves to detect visible light that is radiated out from the light-emitting side (columnar crystals 500a) of the scintillator 500. As viewed from the side in FIG. 20A, an insulating substrate 508, a TFT layer 510, and photoelectric conversion devices 512 are stacked in this order with respect to the irradiated surface 32, along the direction in which radiation 16a through 16c is irradiated. A planarization layer 514 is formed on the bottom surface of the TFT layer 510 so as to cover the photoelectric conversion devices 512.

Further, the radiation detecting unit 502 is constituted as a TFT active matrix substrate (hereinafter referred to as a TFT substrate), in which a plurality of pixels 520, each comprising a photoelectric conversion device 512 made from a photodiode (PD) or the like, a storage capacitor 516, and a thin film transistor (TFT) 518, are formed in a matrix as viewed in plan on the insulating substrate 508.

Furthermore, the photoelectric conversion device 512 is constituted by arranging a photoelectric conversion film 512c between a lower electrode 512a on the side of the scintillator 500, and an upper electrode 512b on the side of the TFT layer 510.

Still further, the TFT 518 of the TFT layer 510 includes a stacked assembly made up of a gate electrode, a gate insulating film, and an active layer (channel layer), and a source electrode and a drain electrode disposed on the active layer are spaced from each other with a gap therebetween.

Further, in the radiation detecting unit 502 that makes up the TFT substrate, a planarization layer 514 for making the radiation detecting unit 502 planar in shape is formed on a side opposite to the arrival direction of the radiation 16a through 16c (on the side of the scintillator 500).

In the following descriptions, in the case that the radiation detector 300 of the fifth modification is contrasted with the radiation detector 170 of the fourth modification, respective constituent elements of the radiation detector 300 correspond respectively with each of the constituent elements of the radiation detector 170.

First, the insulating substrate 508 corresponds with the substrate 172. However, the insulating substrate 508 is not limited as long as it is light transmissive, and is made of a material that absorbs only a small amount of radiation 16a through 16c.

In the case that a glass substrate is used as the insulating substrate 508, the thickness of the radiation detecting unit 502 (TFT substrate) overall is on the order of, for example, 0.7 mm. However, according to the fifth modification, considering making the radiation detecting device 22 thinner in profile, a thin profile substrate made from a light transmissive synthetic resin is used as the insulating substrate 508. As a result, the thickness of the radiation detecting unit 502 overall can be made thinner in profile on the order, for example, of 0.1 mm, whereby the radiation detecting unit 502 can be made to possess flexibility. Further, by making the radiation detection unit 502 flexible, resistance to shocks of the radiation detecting device 22 is improved, and it is more difficult for the radiation detecting device 22 to suffer damage if shocks are applied thereto. Further, plastic resins, aramid, bionanofibers and the like tend not to absorb radiation 16a through 16c, and in the case that the insulating substrate 508 is formed from such materials, since only a small amount of radiation 16a through 16c is absorbed by the insulating substrate 508, even with a structure in which radiation 16a through 16c passes through the insulating substrate 508 as a result of being an ISS type of radiation detector, lowering in sensitivity with respect to radiation 16a through 16c can be suppressed.

With the radiation detecting device 22, it is not essential to utilize a synthetic resin as the insulating substrate 508, and although the thickness of the radiation detecting device 22 will be increased, other materials such as a glass substrate or the like may be used as the insulating substrate 508.

The pixel 520 corresponds to the signal output section 174, and the photoelectric conversion device 512 corresponds to the sensor 176. Owing thereto, the storage capacitor 516 of the pixel 520 corresponds to the capacitor 192 of the signal output section 174, and the TFT 518 corresponds to the thin film transistor 194. Further, the lower electrode 512*a* of the photoelectric conversion device 512 corresponds to the upper electrode 182 of the sensor 176, the photoelectric conversion film 512*c* corresponds to the photoelectric conversion film 186, and the upper electrode 512*b* corresponds to the lower electrode 184.

Stated otherwise, each of the constituent elements of the ISS type radiation detector 300 shown in the fifth modification corresponds in general with each of the constituent elements of the PSS type radiation detector 170 shown in the fourth modification. Accordingly, if the materials used for the constituent elements of the radiation detector 170, which have been described in relation to FIGS. 18 and 19, are applied as materials for the constituent elements corresponding to the radiation detector 300 of the fifth modification, then the same effects according to each of the materials explained with reference to FIGS. 18 and 19 can easily be obtained.

However, different from a PSS type, in an ISS type of radiation detector, because radiation 16*a* through 16*c* passes through the radiation detecting unit 502 to arrive at the CsI (Tl) scintillator 500, it is necessary that the radiation detecting unit 502 overall, including the insulating substrate 508, the pixels 520 and the photoelectric conversion devices 512, be constituted from materials that absorb only a slight amount of radiation 16*a* through 16*c*.

Accordingly, in the fifth modification, in the case that the photoelectric conversion film 512*c* is constituted from an organic photoelectric conversion material, since the photoelectric conversion film 512*c* absorbs almost no radiation 16*a* through 16*c*, in an ISS type of radiation detector in which the radiation detecting unit 502 thereof is arranged so as to permit radiation 16*a* through 16*c* to pass therethrough, attenuation of radiation 16*a* through 16*c* that passes through the radiation detecting unit 502 can be suppressed, and lowering in sensitivity with respect to the radiation 16*a* through 16*c* can also be suppressed.

Accordingly, constituting the photoelectric conversion film 512*c* from an organic photoelectric conversion material is preferable, particularly for an ISS type of radiation detector.

[Sixth Modification]

Figure 21A:
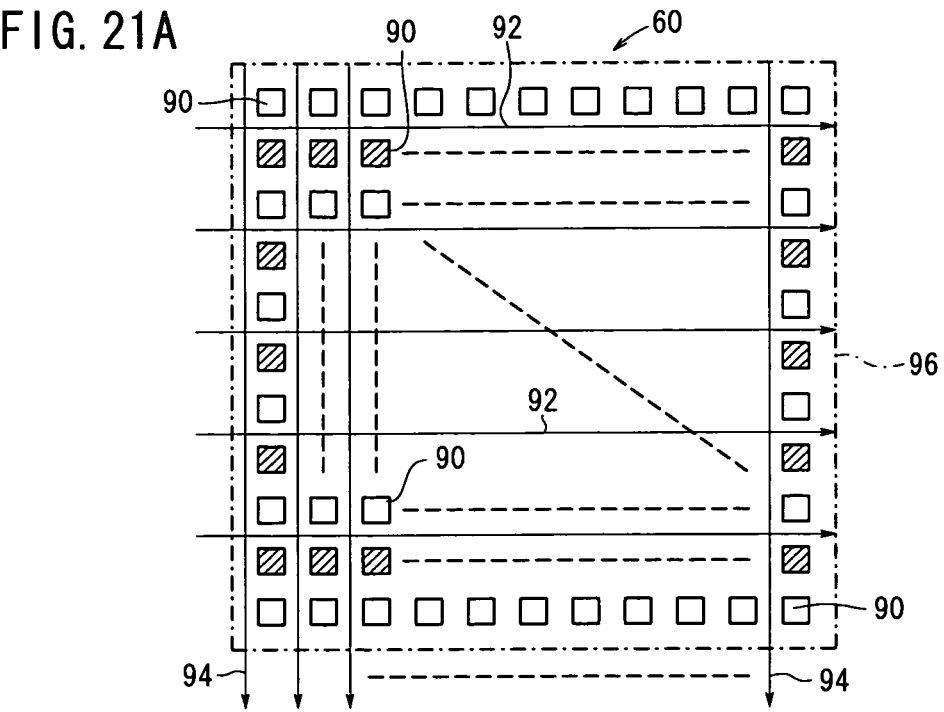
FIGS. 21A and 21B are explanatory diagrams showing a radiographic image capturing system according to a sixth modification.
Figure 21B:
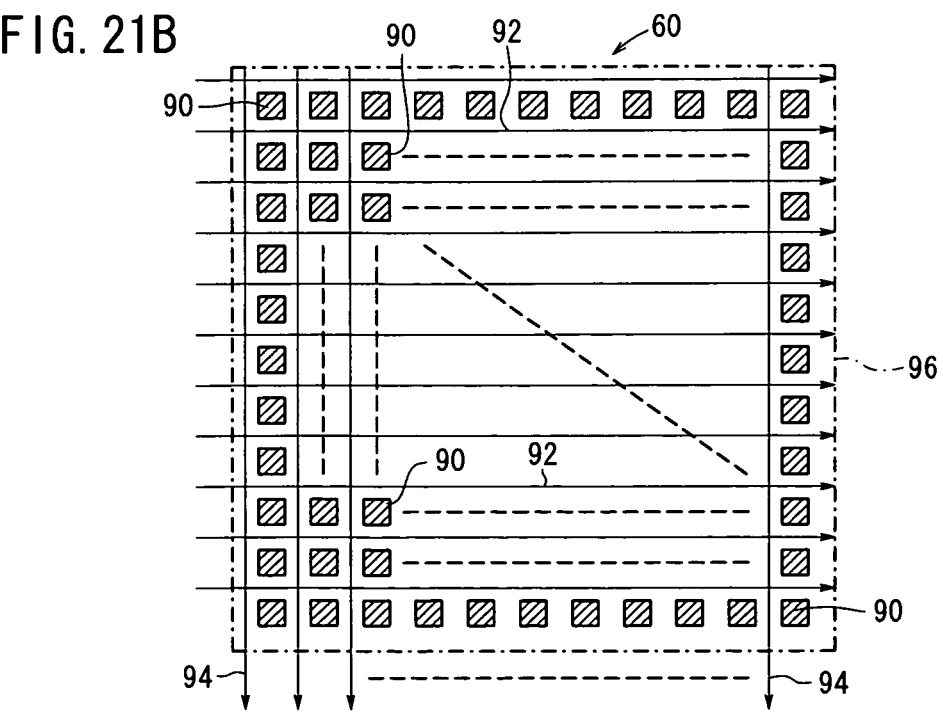

According to a sixth modification, as shown schematically in FIGS. 21A and 21B, after the first image capturing process is performed, as shown in FIG. 21A, image signals from a portion of the pixels 90 indicated by the slanted lines are read out intermittently, to thereby obtain the first radiographic image. Next, after the second image capturing process is carried out, as shown in FIG. 21B, image signals from all of the pixels 90 indicated by the slanted lines are read out, to thereby obtain the second radiographic image. More specifically, concerning reading out of image signals from the pixels 90 for the purpose of acquiring the first radiographic image, the sixth modification differs from the example of FIGS. 1 through 20B, in which the first radiographic image is acquired by reading out image signals from all of the pixels 90.

More specifically, the address signal generator 78 (see FIG. 7) of the cassette controller 74 supplies address signals to the line scanning driver 100 so that only the TFTs 98 (see FIG. 9) connected to the pixels 90 indicated by the slanted lines are turned on, and together therewith, the address signals are supplied to the multiplexer 102 in order to read out the image signals from the pixels 90 indicated by the slanted lines. Accordingly, in the case of FIG. 21A, the first radiographic image can be obtained by supplying control signals via the TFTs 98 only to the gate lines 92 connected to the pixels 90 indicated by the slanted lines, and by reading out image signals from all of the signal lines 94. On the other hand, in the case of FIG. 21B, similar to the case of FIG. 9, the second radiographic image can be obtained by supplying control signals to all of the gate lines 92, and by reading out image signals from all of the signal lines 94.

In this manner, according to the sixth modification, because the image signals are read out intermittently (i.e., in a thinned-out manner), the number of TFTs 98 that are turned on (i.e., subjected to switching) upon acquisition of the first radiographic image is made smaller, and switching noise of the TFTs 98 superimposed in the first radiographic image can be decreased. Accordingly, in the addition processor 148, the radiographic image obtained by carrying out addition processing of the first radiographic image and the second radiographic image is rendered as a radiographic image in which switching noise is small, and which is suitable for diagnostic interpretation by the doctor 26.

[Seventh Modification]

According to a seventh modification, as shown schematically in FIG. 22, the radiation detector 60 is constructed by arranging in order along the direction in which radiation 16*a* through 16*c* is applied, a photoelectric conversion layer 96 (first photoelectric conversion layer) including pixels 90 as first solid state detecting elements and TFTs 98, the scintillator 168, and a photoelectric conversion layer 177 (second photoelectric conversion layer) including pixels 210 as second solid state detecting elements and TFTs 212. In the seventh modification, similar to the case of FIG. 9, each of the pixels 90, 210 are arrayed in a matrix form.

Among the pixels 90, 210, at least the pixels 90 are formed using an organic photoelectric conversion material. As noted above, because the organic photoelectric conversion material does not absorb electromagnetic waves other than light emitted by the scintillator 168 (because it is transmissive to X-rays), the side on which the pixels 90 that utilize the organic photoelectric conversion material are disposed can serve as a side to which radiation 16*a* through 16*c* is applied.

On the other hand, a non-organic photoelectric conversion material such as amorphous silicon or the like possesses the characteristic of absorbing X-rays and becomes deteriorated upon absorption of X-rays. Therefore, concerning the pixels 210, which are arranged on the back surface side in relation to the direction in which radiation 16*a* through 16*c* is applied, such pixels 210 may be formed form a non-organic photoelectric conversion material. In this manner, by forming the pixels 90 from an organic photoelectric conversion material and forming the pixels 210 from a non-organic photoelectric conversion material, the usage life of the pixels 210 can be extended.

Further, because the radiation 16*a* through 16*c* applied to the side of the pixels 90 and which passes through the scintillator 168 is absorbed by the pixels 210 made of a non-organic photoelectric conversion material, the amount of radiation 16*a* through 16*c* that is leaked from the back surface side (side of the pixels 210) can be made small. Furthermore, because the pixels 90 formed by an organic photoelectric conversion material are provided on the side (front surface side) irradiated with radiation 16*a* through 16*c*, attenuation of the radiation 16*a* through 16*c* by the pixels 90 can be decreased. Accordingly, radiation 16a through 16c can be made incident on the scintillator 168 without undue attenuation thereof.

In the seventh modification in which the radiation detector 60 is constructed in the manner described above, the address signal generator 78 (see FIG. 7) of the cassette controller 74 acquires the first radiographic image by reading out image signals from all of the pixels 210 after the first image capturing process, and next acquires the second radiographic image by reading out image signals from all of the pixels 90 after the second image capturing process.

More specifically, immediately after the first image capturing process, image signals are not read out from the pixels 90. On the other hand, immediately after the second image capturing process, image signals are not read out from the pixels 210, and the second radiographic image, which is read out from all of the pixels 90, becomes the radiographic image suitable for diagnostic interpretation by the doctor 26. Accordingly, with the seventh modification, the addition process of the addition processor 148 is unnecessary.

Stated otherwise, the first radiographic image read out from the pixels 210 becomes a radiographic image used only for the purpose of the radiation dose weighting of the radiation 16a through 16c in the second image capturing process. Accordingly, the respective pixels 210 function as monitor pixels for acquiring the second radiographic image.

In the foregoing manner, according to the seventh modification, because the addition process of the addition processor 148 is unneeded, imposition of switching noise, which occurs upon reading out the first image signal, on the second radiographic image (the radiographic image suitable for diagnostic interpretation by the doctor 26) can be avoided. Owing thereto, switching noise in the radiographic image that is used for diagnostic interpretation can be further reduced.

As noted above, because the respective pixels 210 function as monitor pixels, the photoelectric conversion layer 177 including the pixels 210 may make use of a photoelectric conversion layer having defective pixels therein, a photoelectric conversion layer having coarse pixels, or a photoelectric conversion layer having a diminished photoelectric conversion function.

[Eighth Modification]

Figure 23:
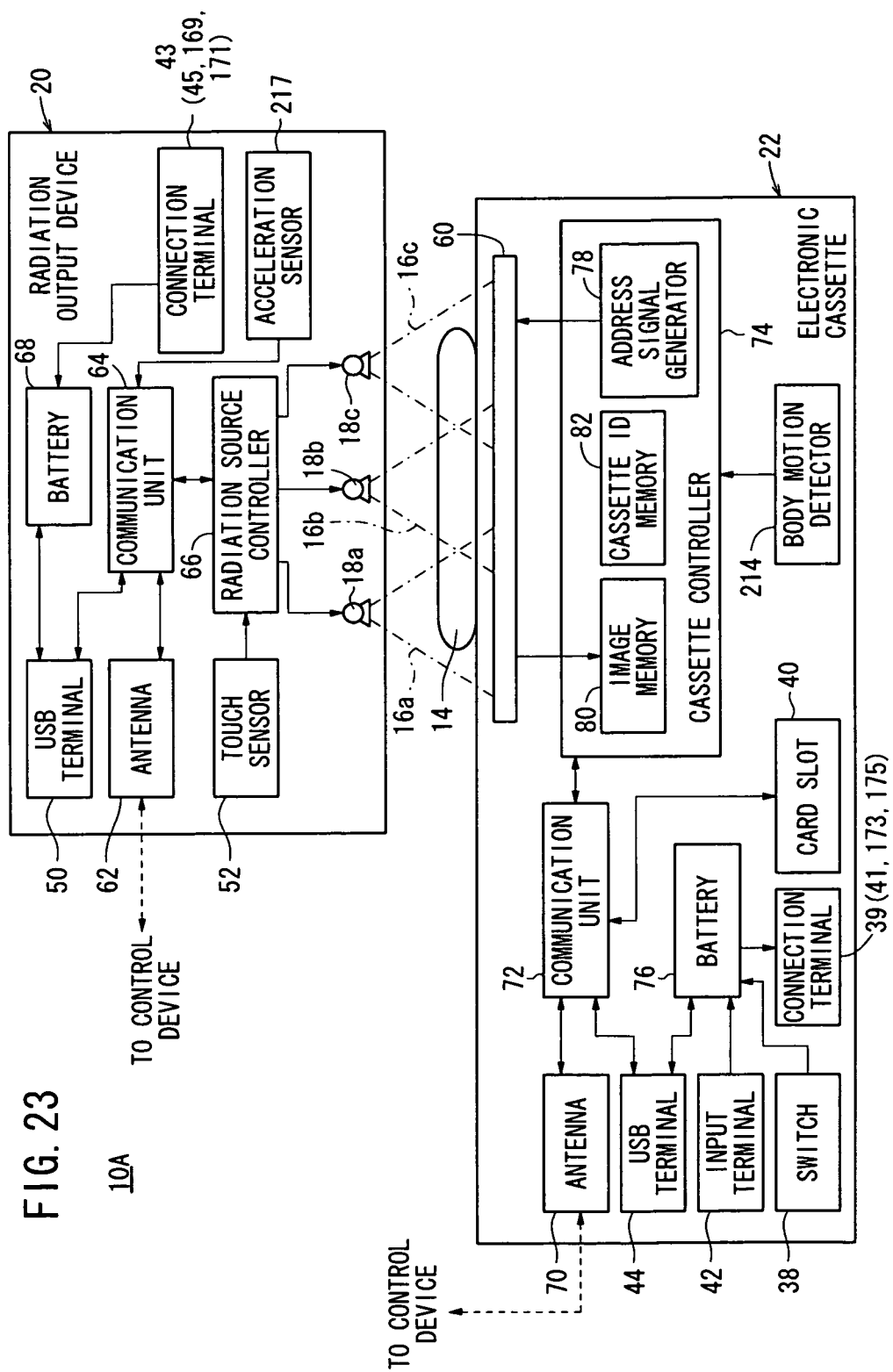
FIG. 23 is a block diagram showing a radiographic image capturing system according to an eighth modification.
Figure 24:
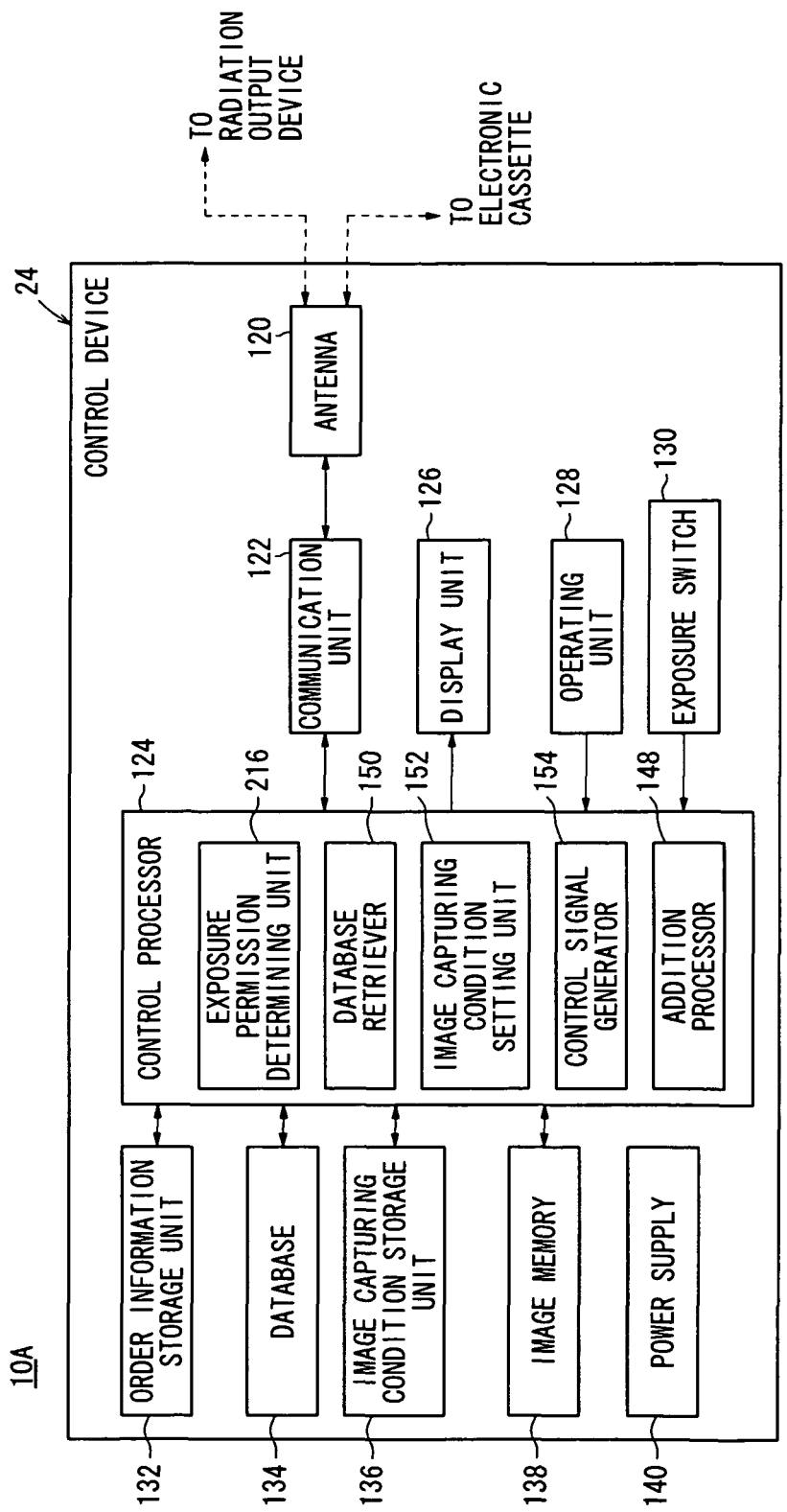
FIG. 24 is a block diagram showing a radiographic image capturing system according to an eighth modification.

According to an eighth modification, as shown in FIGS. 23 and 24, the radiation detecting device 22 further includes a body motion detector 214, and the radiation output device 20 additionally incorporates an acceleration sensor 217 therein, and the control processor 124 of the control device 24 further includes an exposure permission determining unit 216.

The body motion detector 214 detects body movements of (the region to be imaged of) the subject 14, who is positioned with respect to the imaging area 36 (see FIGS. 2A through 3B). The acceleration sensor 217 detects acceleration of the radiation output device 20. The exposure permission determining unit 216 determines whether emission of radiation 16a through 16c from the radiation sources 18a through 18c (application of radiation 16a through 16c to the region to be imaged) is permitted or interrupted, based on the detection result of the body motion detector 214 or the detection result of the acceleration sensor 217.

More specifically, the body motion detector 214 may be at least one of (1) a pressure sensor for detecting pressure imposed on the radiation detecting device 22 from (the region to be imaged of) the subject 14 that is positioned, (2) a vibration sensor for detecting vibration of the radiation detecting device 22 caused by movement of the region to be imaged of the subject 14, and (3) a contact sensor for detecting contact of the subject 14 with respect to the radiation detecting device 22. The physical value detected by the body motion detector 214 is a physical value related to motion of (the region to be imaged of) the subject 14. In addition, the body motion detector 214 sends the detection signal representing the physical value to the control device 24 by way of wireless communications from the communication unit 72 via the antenna 70.

In the case that the doctor 26 retains the radiation output device 20 by gripping the grip 28, the acceleration sensor 217 sequentially detects the acceleration of the radiation output device 20, and sends a detection signal representing the detected acceleration to the control device 24 via a wireless link via the communication unit 64 and the antenna 62. The acceleration, which is detected by the acceleration sensor 217, is a physical quantity corresponding to wobbling movements of the radiation output device 20 retained by the doctor 26.

On the other hand, in the case that the exposure permission determining unit 216 judges that the change of the pressure with time, the size of the vibration, the contact area between the subject 14 and the radiation detecting device 22, or the acceleration of the radiation output device 20, which relate to physical quantities indicative of detection signals received respectively via the antenna 120 and the communication unit 122, have exceeded predetermined thresholds, image capturing of the radiographic image with respect to the subject 14 is suspended, and the display unit 126 (notification unit) notifies the doctor 26 that image capturing has been suspended.

Next, operations of the eighth embodiment shall be explained with reference to the flowchart of FIG. 25.

During the first image capturing process, the body motion detector 214 sequentially detects the physical quantity concerning movement of the region to be imaged of the subject 14, and detection signals of the detected physical quantity are sent sequentially via wireless communications to the control device 24. Further, the acceleration sensor 217 sequentially detects the acceleration of the radiation output device 20, and sequentially sends the detection signal indicative of the detected acceleration (physical quantity) wirelessly to the control device 24. The exposure permission determining unit 216 sequentially registers data of each of the physical quantities indicative of the sequentially received detection signals.

In addition, in step S30, after step S8 (see FIG. 13) in which the first image capturing process is completed, the exposure permission determining unit 216 determines whether or not data of the physical quantities exist, which are in excess of predetermined thresholds among the registered data of the respective physical quantities. In the case that data of a physical quantity is discovered, which is in excess of a predetermined threshold (step S30: YES), then the exposure permission determining unit 216 judges that motion of the region to be imaged of the subject 14 or wobbling movement of the radiation output device 20 has occurred, which could adversely influence the first radiographic image captured during the first image capturing process.

Motions of the region to be imaged of the subject 14 or wobbling movements of the radiation output device 20, which may adversely influence the first radiographic image, are defined, for example, as body motions in which the region to be imaged is wobbled, or as wobbling movements of the radiation output device 20, to such an extent that the region to be imaged cannot be identified upon attempting to identify the region to be imaged of the subject 14 that is reflected in the first radiographic image, or alternatively, are defined as body motions in which the region to be imaged in the radiographic image is wobbled, or as wobbling movements of the radiation output device 20, to such an extent that weighting processing cannot reliably be carried out upon weighting on the doses of radiation 16*a* through 16*c*.

Next, in step S31, the exposure permission determining unit 216 notifies the doctor 26 via the display unit 126 that the second image capturing step has been suspended. Further, the exposure permission determining unit 216 indicates (step S32) via the display unit 126 that recapturing of the radiographic image (carrying out of the first image capturing process again) should be implemented. By visual confirmation of the content displayed on the display unit 126, the doctor 26 can grasp that the first image capturing process has failed, and step S2 is returned to in preparation for recapturing the first radiographic image.

On the other hand, in step S30, if it is judged that data of the physical quantities do not exist that are in excess of predetermined thresholds among the data of the physical quantities registered in the exposure permission determining unit 216 (step S30: NO), the exposure permission determining unit 216 determines that movement of the region to be imaged or wobbling of the radiation output device 20 has not occurred during the first image capturing process, which could adversely influence the first radiographic image. As a result, in the control device 24, implementation of the process of step S9 is enabled, and preparations can progress toward the second image capturing process.

In this manner, according to the eighth modification, body movements of the region to be imaged of the subject 14 or wobbling of the radiation output device 20 during the first image capturing process are detected, and if such body movements or wobbling of the radiation output device 20 are of such an extent as to adversely influence the radiographic image, then a notification (indication) is made to suspend the second image capturing process and to carry out recapturing, i.e., to perform the first image capturing process again. Therefore, a radiographic image, which is suitable for diagnostic interpretation thereof by the doctor 26, can be acquired reliably.

The eighth modification is not limited by the foregoing explanations. For example, the exposure permission determining unit 216 may function as a wobbling movement amount calculator for calculating an amount of wobbling of the region to be imaged of the subject 14 in the first radiographic image, such that if the wobbling amount exceeds a predetermined threshold, a notification (indication) may be given to suspend the second image capturing process and to perform recapturing of the first radiographic image. More specifically, in this case, the exposure permission determining unit 216 functions doubly as a body motion detector for detecting movements of the region to be imaged of the subject 14.

[Ninth Modification]

Figure 26:
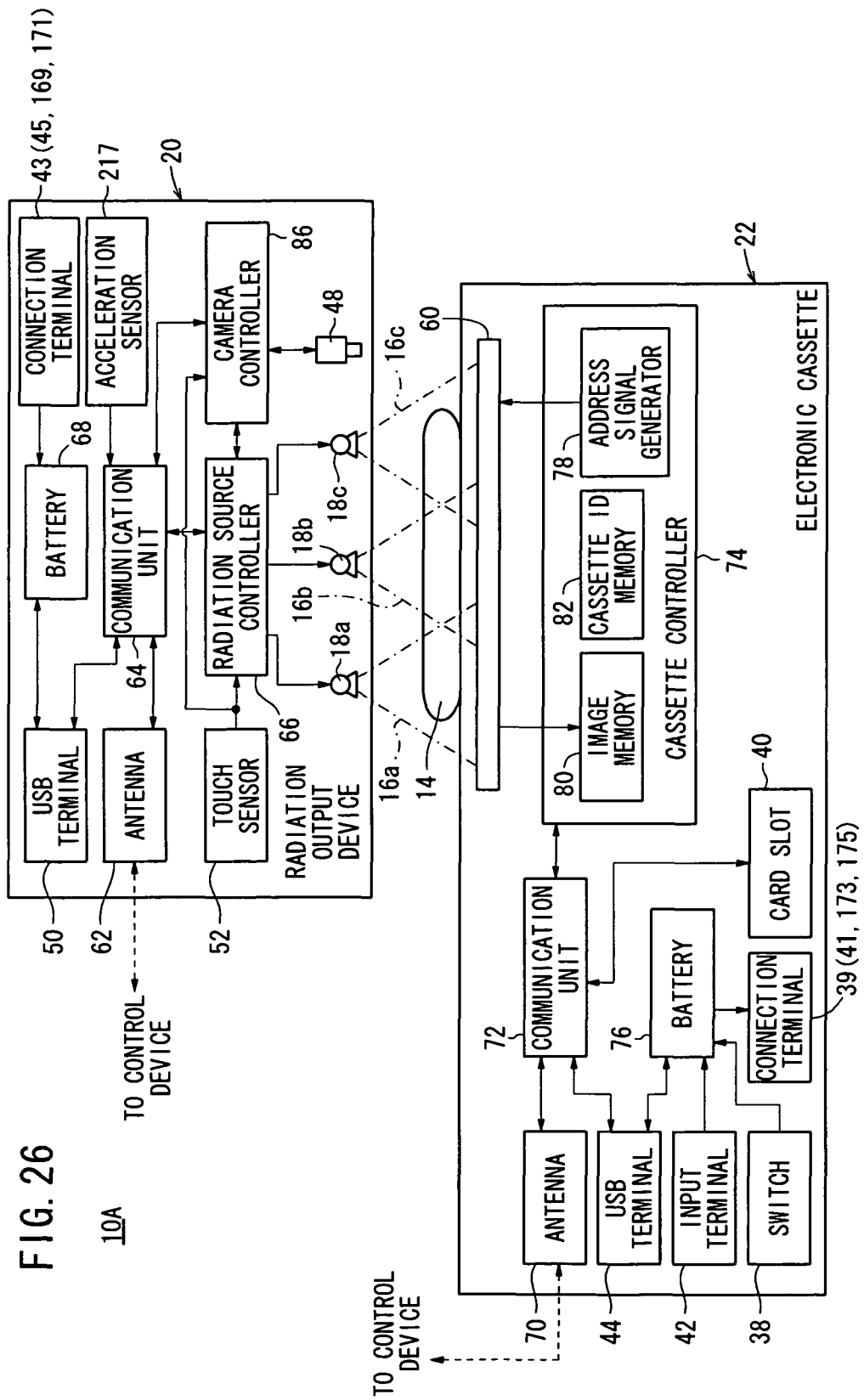
FIG. 26 is a block diagram showing a radiographic image capturing system according to the ninth modification.
Figure 27A:
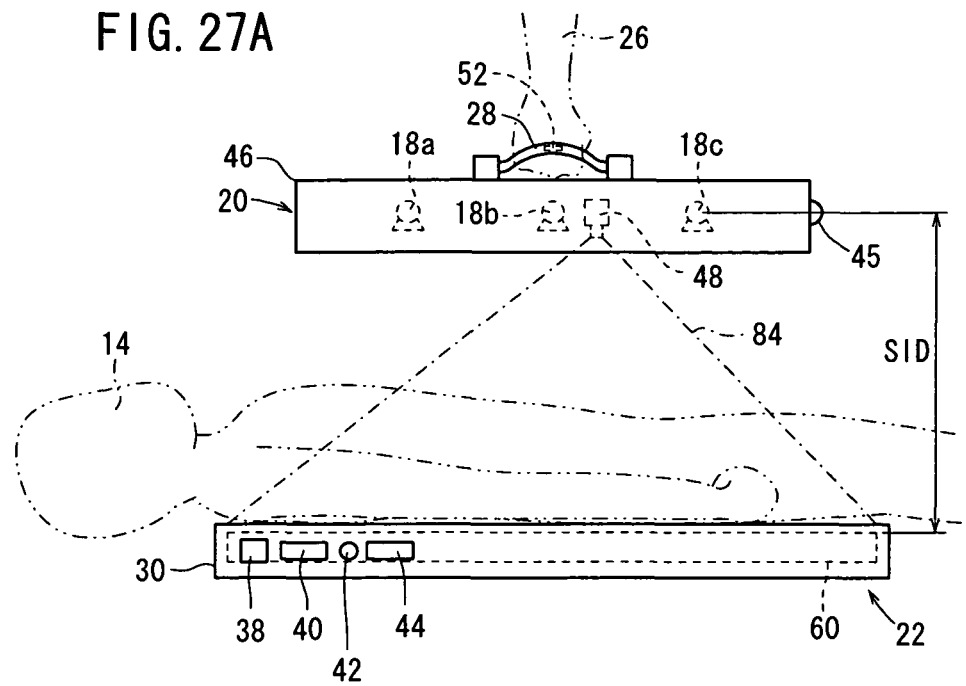
FIGS. 27A and 27B are side elevational views showing image capturing by a camera with respect to a region to be imaged of the subject.
Figure 27B:
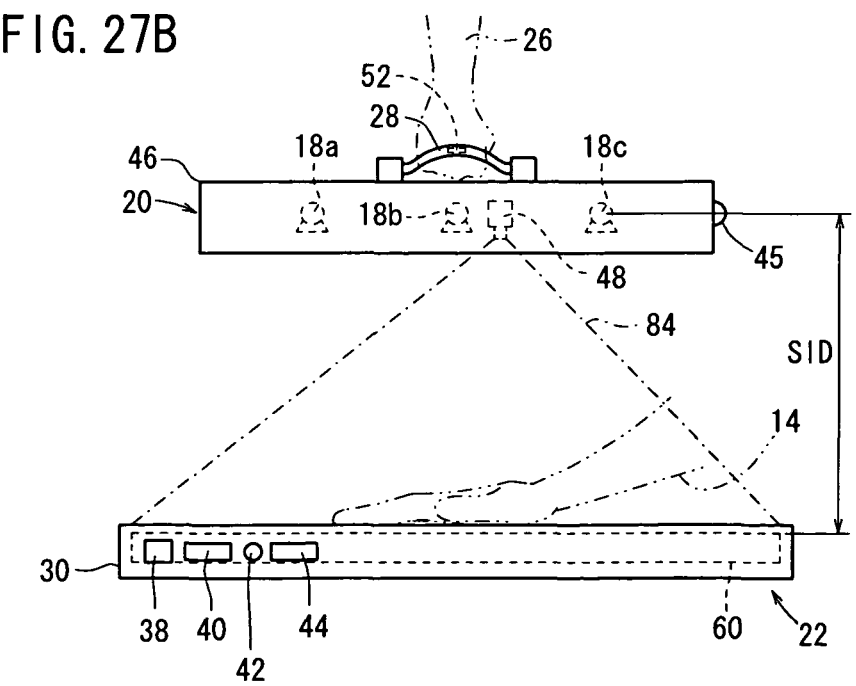

According to a ninth modification, as shown in FIGS. 26 through 27B, image capturing is performed by means of a web camera 48, which is disposed in the radiation output device 20, in order to capture a region to be imaged of the subject 14 having been positioned with respect to the imaging area 36. Based on the camera image of the region to be image captured by the web camera 48, the exposure permission determining unit 216 (see FIG. 23) determines whether to allow or prohibit output of radiation (application of radiation 16*a* through 16*c* with respect to the region to be imaged) from the radiation sources 18*a* through 18*c*.

Features of the web camera 48 shall be described in further detail below.

The web camera 48 serves for imaging a predetermined imaging range 84 in order to acquire a camera image (optical image) thereof. In this case, the radiation output device 20 and the web camera 48 are integrally combined with each other.

Integral combination of the radiation output device 20 and the web camera 48 is not limited to an arrangement in which the web camera 48 is housed in the radiation output device 20, but refers to any arrangement in which the web camera 48 is integrally joined (connected) to the radiation output device 20, at least when the radiographic image capturing system 10A is in use. For example, integral combination of the radiation output device 20 and the web camera 48 includes (1) an arrangement in which the web camera 48 and the radiation output device 20 are connected to each other by a cable provided by the radiographic image capturing system 10A, (2) an arrangement in which the web camera 48 and the radiation output device 20 are connected to each other by a cable provided by a doctor 26, and (3) an arrangement in which the radiation output device 20 and the web camera 48 are joined to each other when the radiographic image capturing system 10A is in use, and wherein the radiation output device 20 and the web camera 48 can be disconnected (separated) from each other when the radiographic image capturing system 10A is undergoing maintenance or is not in use.

To make the web camera 48 disconnectable from the radiation output device 20 when the radiographic image capturing system 10A is undergoing maintenance or is not in use, the web camera 48 may be joined to the radiation output device 20 by a joining means such as a clip or the like. The web camera 48 may be joined to the radiation output device 20 by the joining means only when the radiographic image capturing system 10A is in use. The joining means may incorporate a ball joint for enabling the orientation of the web camera 48, which is joined to the radiation output device 20, to be freely changed. If the web camera 48 is joined to the radiation output device 20 by the joining means, then it is necessary for the web camera 48 and the radiation output device 20 to be electrically connected to each other via a wired link, e.g., a USB cable, or a wireless link.

If the radiation output device 20 and the web camera 48 are connected to each other by a cable, then since the web camera 48 can independently be placed in a desired position within a range defined by the length of the cable, the web camera 48 can be positioned with greater freedom than if the web camera 48 were housed in the radiation output device 20.

Further, in the radiation output device 20, the web camera 48 is positioned closely to the radiation source 18*b*. Additionally, if a detection signal is output from the touch sensor 52, the radiation output device 20 enables a camera image to be captured with respect to an imaging range 84 of the web camera 48. More specifically, the radiation output device 20 includes a camera controller 86, such that if the detecting signal is input to the camera controller 86, the camera controller 86 controls the web camera 48 to initiate image capturing of the imaging range 84, and the camera image taken by the web camera 48 is sent to the control device 24 via wireless communications through the communication unit 64 and the antenna 62.

Accordingly, if the doctor 26 grips the grip 28 and orients the radiation output device 20 toward the radiation detecting device 22, image capturing of the imaging range 84, which includes therein the imaging area 36, is enabled. If the region to be imaged of the subject 14 is positioned with respect to the imaging area 36, because the region to be image is positioned inside of the imaging range 84, the web camera 48 can capture a camera image in which the region to be imaged is reflected.

The web camera 48 is capable of continuously capturing images of the imaging range 84 so as to capture successive camera images (a moving image), is capable of intermittently capturing images of the imaging range 84 at predetermined time intervals so as to acquire camera images (still images) which are captured intermittently, or can acquire a camera image (still image) which is captured at a certain time.

FIG. 27A shows the manner in which the web camera 48 captures an image of the chest of the subject 14, which is a comparatively large region to be imaged, whereas FIG. 27B shows the manner in which the web camera 48 captures a radiographic image of the hand of the subject 14, which is a comparatively small region to be imaged.

The web camera 48 sends the camera image of the region to be imaged of the subject 14 wirelessly to the control device 24 via the communication unit 64 and the antenna 62. In the case it is judged that the movement amount (physical value) of the region to be imaged of the subject 14 in the camera image, which is received via the antenna 120 and the communication unit 122, has exceeded a predetermined threshold, the exposure permission determining unit 216 suspends image capturing of the radiographic image with respect to the subject 14, and notifies the doctor 26 through the display unit 126 (notification means) that image capturing was suspended.

Figure 25:
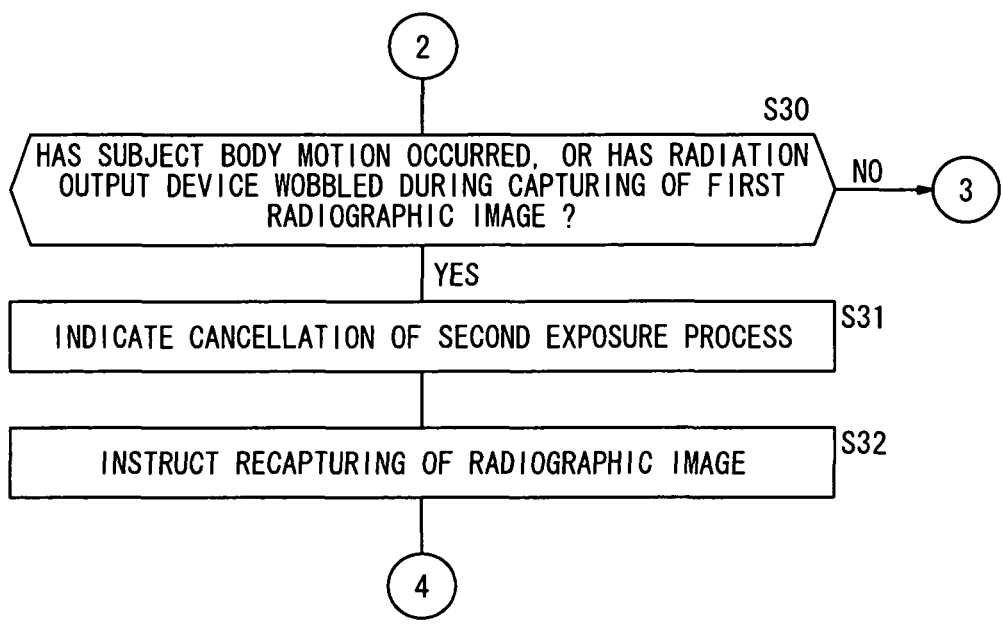
FIG. 25 is a flowchart of an operation sequence of the radiographic image capturing system according to eighth and ninth modifications.

Additionally, in the ninth modification, as shown in the flowchart of FIG. 25, during the first image capturing process, the web camera 48 captures a camera image of the imaging range 84, and sends the camera image to the control device 24 by way of wireless communications. The exposure permission determining unit 216 records the received data of the camera image in the image memory 138.

After step S8 (see FIG. 13) in which the first image capturing process is completed, the exposure permission determining unit 216 determines whether or not data of the movement amount of a region to be imaged exists, which is in excess of a predetermined threshold among data of the recorded camera images. In the case that data of the movement amount is discovered, which is in excess of the predetermined threshold (step S30: YES), then the exposure permission determining unit 216 judges that body motion of the region to be imaged of the subject 14 has occurred, which could adversely influence the first radiographic image captured in the first image capturing step, and processing from step S31 and steps subsequent thereto are implemented. On the other hand, in the case that data of the movement amount is not discovered that is in excess of the predetermined threshold among data of the camera images recorded in the exposure permission determining unit 216 (step S30: NO), the exposure permission determining unit 216 determines that movement of the region to be imaged has not occurred during the first image capturing process which could adversely influence the first radiographic image captured in the first image capturing step, whereupon the control device 24 implements the process of step S9.

In this manner, in the ninth modification as well, because body motion of the region to be imaged of the subject 14 during the first image capturing process is detected by using the camera image, the same effects as those of the eighth modification can be achieved. Further, in the ninth modification, although the descriptions thereof have centered on operations of the web camera 48, because the acceleration sensor 217 is incorporated in the radiation output device 20, in addition to the movement amount of the region to be imaged in the camera image captured by the web camera 48, using the acceleration of the radiation output device 20 detected by the acceleration sensor 217, the occurrence of movement of the region to be imaged, as well as the occurrence of wobbling motions of the radiation output device 20 may also be determined in the exposure permission determining unit 216.

[Other Structures of the Eighth and Ninth Modifications]

In the foregoing explanations of the eighth and ninth modifications, after the first image capturing process, it is determined whether or not movement of the region to be imaged of the subject 14 during the first image capturing process has occurred, and in the case that such movement is determined to have occurred, the second image capturing process is suspended, and recapturing of the first radiographic image is implemented.

However, the eight and ninth modifications are not limited by the foregoing explanations, and in the case that the region to be imaged of the subject 14 is already moving, or if wobbling of the radiation output device already occurs during preparations for the first image capturing process (prior to application of radiation 16a through 16c), the first image capturing process may be delayed or suspended, and thereafter, the first image capturing process can be enabled once such body movements or wobbling have settled down.

Figure 28:
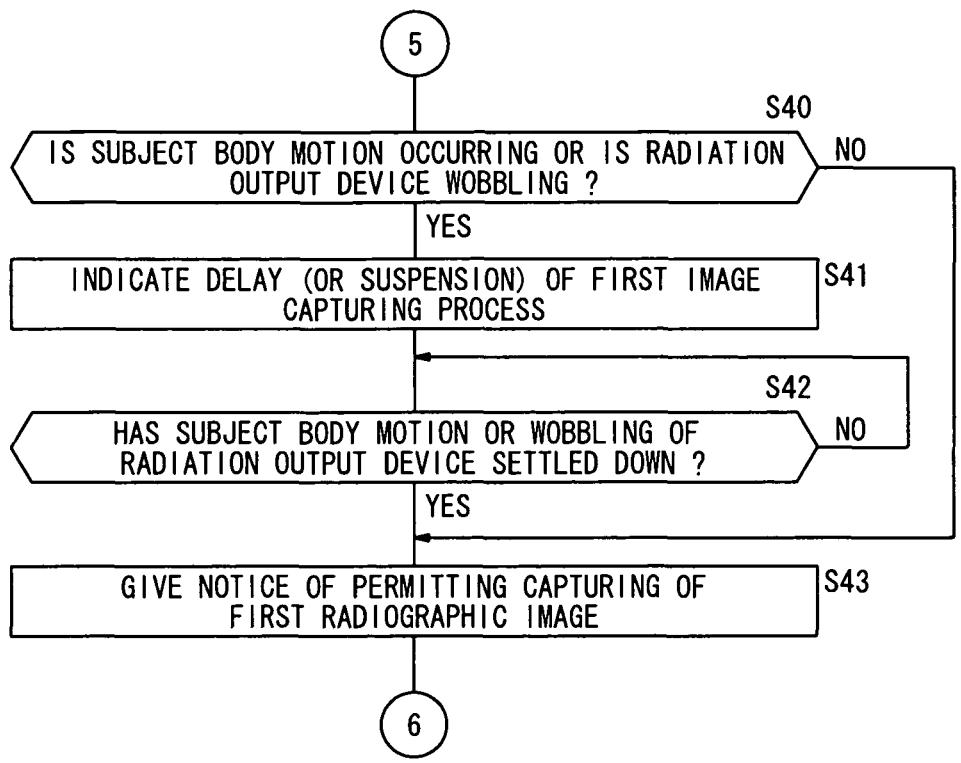
FIG. 28 is a flowchart of another operation sequence of the radiographic image capturing system according to the eighth and ninth modifications.

More specifically, as shown in the flowchart of FIG. 28, the acceleration (physical quantity) of the radiation output device 20 is detected by the acceleration sensor 217 (see FIGS. 23 and 26) during preparation for the first image capturing process, and a detection signal indicative of the detected acceleration is sent wirelessly to the control device 24. Together therewith, a physical quantity relating to the body movement of the region to be imaged of the subject 14 is detected by the body motion detector 214, and a detection signal indicative of the physical quantity is sent wirelessly to the control device 24. Alternatively, the web camera 48 captures an image of the imaging range 84, and the camera controller 86 sends the camera image of the imaging range 84 wirelessly to the control device 24. In the above cases, in step S40 after step S2 (see FIG. 13), the exposure permission determining unit 216 determines whether or not the physical quantity indicated by the received detection signal, or the movement amount of the region to be imaged in the received camera image is in excess of a predetermined threshold.

In the case that the physical quantity or the movement amount has exceeded the aforementioned thresholds, the exposure permission determining unit 216 determines that movement of the region to be captured of the subject 14, or wobbling of the radiation output device 20 has occurred, which could adversely influence the first radiographic image (step S40: YES), and it is determined to delay or suspend the first image capturing process.

In the following step S41, the exposure permission determining unit 216 notifies the doctor 26 through the display unit 126 that the first image capturing process has been delayed or suspended.

After the notification of step S41, the acceleration sensor 217 sequentially detects the acceleration of the radiation output device 20, and continuously sends wirelessly to the control device 24 the detection signal indicative of such acceleration. Together therewith, the body motion detector 214 sequentially detects the physical quantity related to movement of the region to be imaged of the subject 14, and continuously sends wirelessly to the control device 24 the detection signal indicative of the physical quantity. Alternatively, the web camera 48 captures an image of the imaging range 84, and the camera controller 86 continuously sends wirelessly to the control device 24 the camera image of the imaging range 84.

Accordingly, in step S42, the exposure permission determining unit 216 determines whether or not the physical quantity indicated by the received detection signal, or the received amount of movement of the region to be imaged in the camera is less than the predetermined threshold, and more specifically, it is determined whether movement of the region to be imaged of the subject 14, or wobbling of the radiation output device 20 has settled down or not. If the physical quantity or the movement amount is less than the threshold value, and it is judged that the body motion or wobbling has settled down (step S42: YES), then the exposure permission determining unit 216 releases the suspension or delay of the first image capturing process, and displays on the display unit 126 a notification to the effect that the first image capturing process is permitted (step S43). By visually confirming the content displayed on the display unit 126, the doctor 26 grasps that permission has been granted for the first image capturing process, and then it is possible for step S3 to be implemented.

In step S40, in the event that body movement of the region to be imaged of the subject 14, or wobbling of the radiation output device 20 does not occur, since body motion or wobbling does not occur that could adversely influence the first radiographic image, the exposure permission determining unit 216 judges that there is no problem for the first image capturing process to be carried out (step S40: NO), and implements the process of step S43.

By applying the process steps shown in FIG. 28 to the eighth modification and the ninth modification, because the first radiographic image can reliably be acquired, in effect, this enables acquisition of the second radiographic image, and acquisition of a radiographic image suitable for diagnostic interpretation, to reliably be carried out.

[Tenth Modification]

Figure 29:
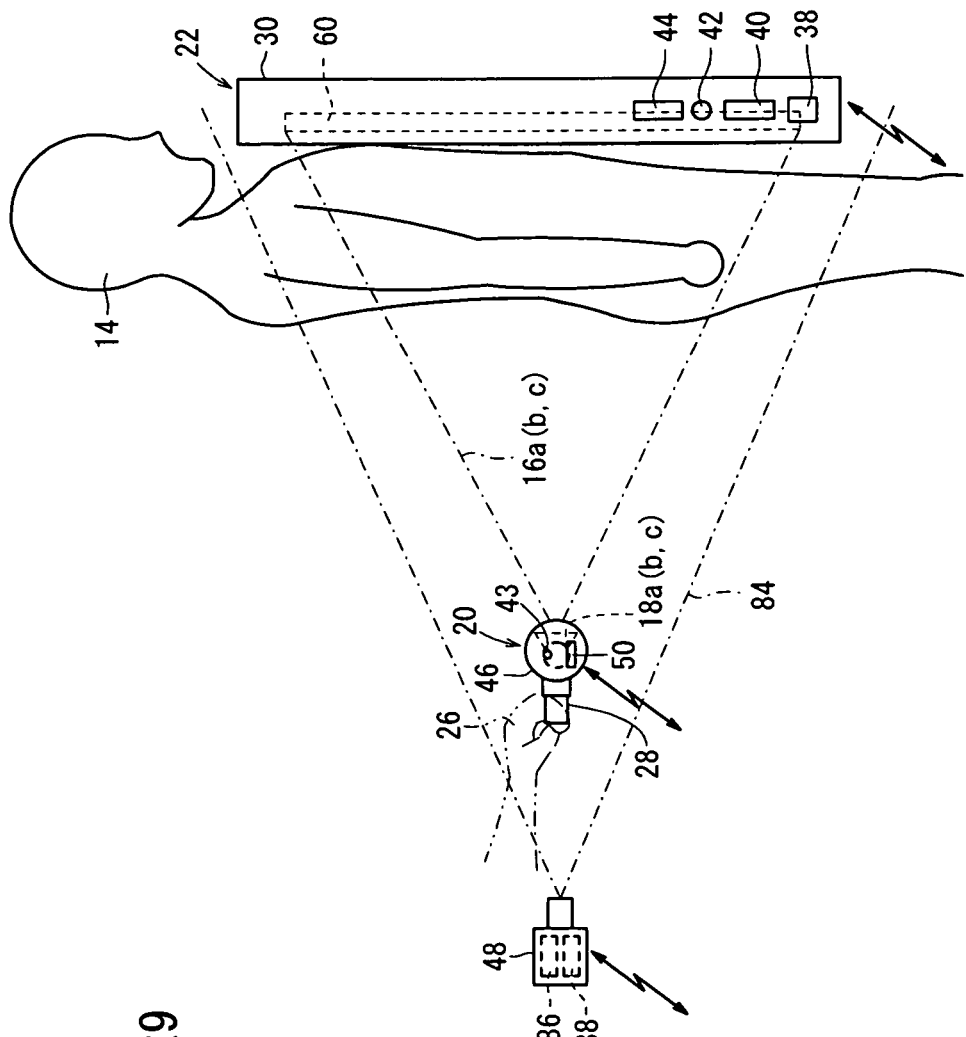
FIG. 29 is a side elevational view showing a radiographic image capturing system according to a tenth modification.

According to a tenth modification, as shown in FIG. 29, the web camera 48 is separate from the radiation output device 20 and the radiation detecting device 22. In this case, the web camera 48 captures a camera image of the radiation output device 20, the region to be imaged of the subject 14, and the radiation detecting device 22. The web camera 48 includes a camera controller 86 and a communication unit 88 for sending signals to and receiving signals from an external circuit wirelessly. In this case, if the control processor 124 of the control device 24 (see FIG. 8) receives an activation signal from the radiation output device 20, the control processor 124 sends a control signal to the communication unit 88 via a wireless link. The camera controller 86 controls the web camera 48 in order to start capturing the imaging range 84, based on the control signal received via the communication unit 88. In addition, the camera controller 86 sends to the control device 24 wirelessly from the communication unit 88 the camera image captured by the web camera 48. According to the ninth modification, inasmuch as the radiation output device 20, the radiation detecting device 22, the control device 24, and the web camera 48 are connected wirelessly over the same wireless link, no cables are required in order for such devices to send and receive signals.

Accordingly, in the tenth modification as well, the same effects as those of the ninth modification can easily be obtained.

[Eleventh Modification]

According to a eleventh modification, as shown in FIG. 30, the web camera 48 is incorporated in a control device 24 in the form of a portable terminal, so that the web camera 48 and the control device 24 are integrally combined with each other.

The portable control device 24 comprises a laptop or notebook type of personal computer (PC) including a main body 114, which incorporates an operating unit 128 and a communication unit 122, a cover body 118 incorporating therein a display unit 126 and the web camera 48, and a hinge 116 interconnecting the main body 114 and the cover body 118. Therefore, the control device 24 and the web camera 48 are integrally combined with each other.

Integral combination of the control device 24 and the web camera 48, similar to integral combination of the radiation output device 20 and the web camera 48, is not limited to an arrangement in which the web camera 48 is housed in the control device 24, but refers to any arrangement in which the web camera 48 is integrally joined (connected) to the control device 24, at least when the radiographic image capturing system 10A is in use. For example, integral combination of the control device 24 and the web camera 48 includes (1) an arrangement in which the web camera 48 and the control device 24 are connected to each other by a cable provided by the radiographic image capturing system 10A, (2) an arrangement in which the web camera 48 and the control device 24 are connected to each other by a cable provided by the doctor 26, and (3) an arrangement in which the control device 24 and the web camera 48 are joined to each other when the radiographic image capturing system 10A is in use, and wherein the web camera 48 can be disconnected (separated) from the control device 24 when the radiographic image capturing system 10A is undergoing maintenance or is not in use.

To make the web camera 48 disconnectable from the control device 24 when the radiographic image capturing system 10A is undergoing maintenance or is not in use, the web camera 48 may be joined to the control device 24 by a joining means such as a clip or the like. The web camera 48 may be joined to the control device 24 by such a joining means only when the radiographic image capturing system 10A is in use. The joining means may incorporate a ball joint for freely changing the orientation of the web camera 48 that is joined to the control device 24. If the web camera 48 is joined to the control device 24 by such a joining means, then it is necessary for the web camera 48 and the control device 24 to be electrically connected to each other by a wired link (e.g., a USB cable) or a wireless link.

If the control device 24 and the web camera 48 are connected to each other by a cable, then since the web camera 48 can independently be placed at a desired position within a range defined by the length of the cable, the web camera 48 can be positioned with greater freedom than if the web camera 48 were housed in the control device 24.

One side of the main body 114 has an input terminal 142 for connection to an AC adapter, a card slot 144 for receiving a memory card (not shown) therein, and a USB terminal 146 for connection to a USB cable (not shown).

In a state in which the control device 24 is arranged, such that the cover body 118 is turned away from the main body 114 about the hinge 116 in order to orient the web camera 48 toward the radiation output device 20, the region to be imaged of the subject 14, and the radiation detecting device 22, in the event that the control processor 124 (see FIG. 8) receives an activation signal from the radiation output device 20, the control processor 124 outputs a control signal to the camera controller 86. Based on the control signal, the camera controller 86 controls the web camera 48 in order to start capturing a camera image of the imaging range 84. The camera controller 86 then outputs the camera image captured by the web camera 48 to the control processor 124.

In this case, since the web camera 48 is incorporated in the control device 24, the control device 24 can reliably acquire a camera image captured by the web camera 48. If the control processor 124 incorporates therein the function of the camera controller 86, then the control processor 124 can directly control the web camera 48. According to the eleventh modification, inasmuch as the radiation output device 20, the radiation detecting device 22, and the control device 24 are connected wirelessly over the same wireless link, no cables are required for such devices to send and receive signals therebetween.

Thus, in the eleventh modification as well, the various effects and advantages of the ninth and tenth modifications can easily be obtained.

[Structures of Second Embodiment]

Next, a radiographic image capturing system 10B according to a second embodiment, in relation to a radiographic image capturing method, will be described with reference to FIGS. 31 through 39.

In the second embodiment, structural elements thereof, which are the same as those of the first embodiment (see FIGS. 1 through 30) are designated by the same reference numerals, and detailed explanations of such features are omitted. Further, where necessary, in the description of the second embodiment, explanations shall also be made with reference to FIGS. 1 through 30.

In outline form, the radiographic image capturing system 10B according to the second embodiment differs from the first embodiment in the following points.

Figure 31A:
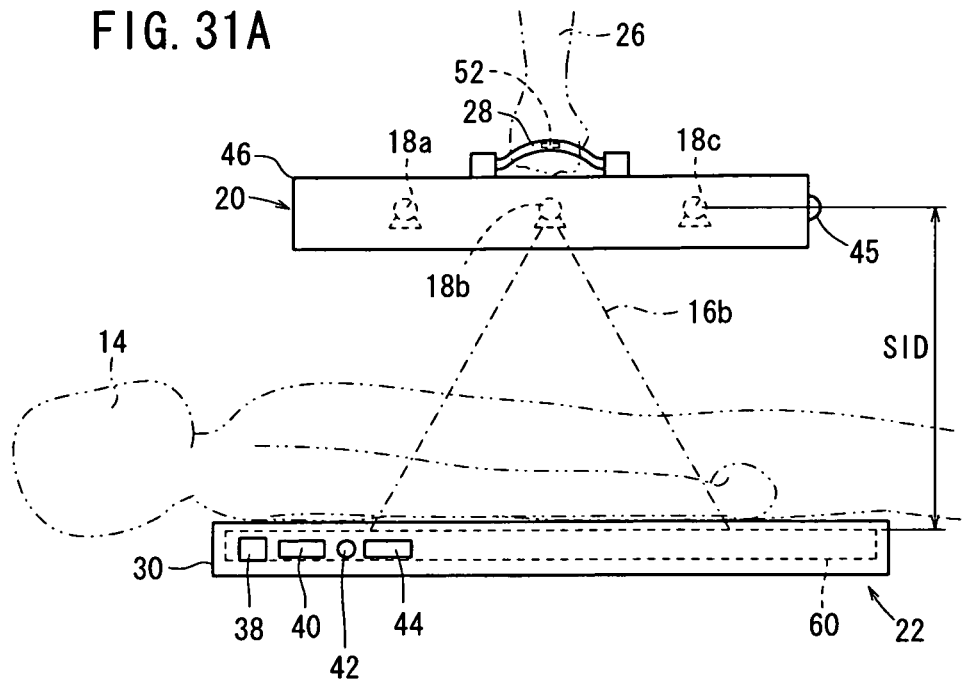
FIGS. 31A and 31B are side elevational views showing application of radiation with respect to a region to be imaged of the subject.
Figure 31B:
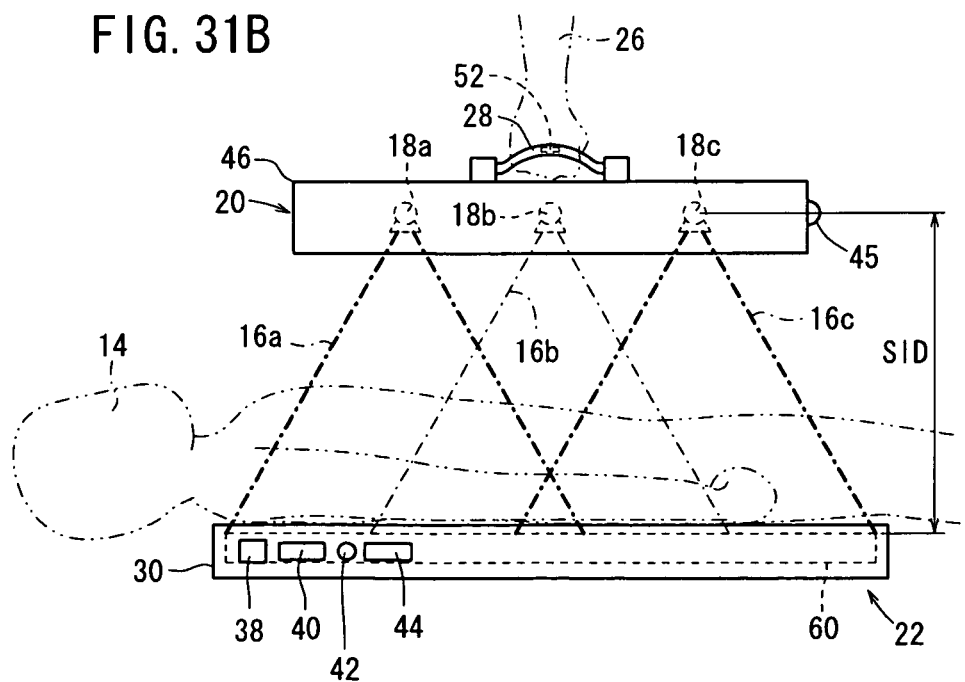
Figure 32A:
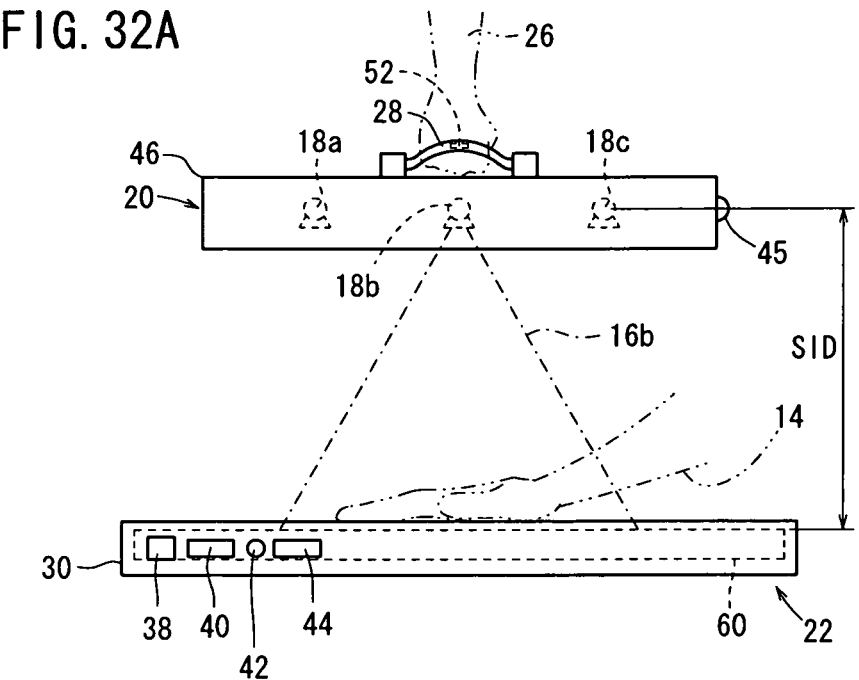
FIGS. 32A and 32B are side elevational views showing application of radiation with respect to a region to be imaged of the subject.

More specifically, as shown in FIGS. 31A through 32B, in the second embodiment, in the case that a radiographic image is captured with respect to the subject 14, at first, a pre-exposure process (first image capturing process) is carried out, in which a comparatively small dose of radiation (radiation 16b as shown in FIGS. 31A and 32A) is applied to the subject 14 from at least one of the radiation sources (the central radiation source 18b shown in FIGS. 31A and 32A) from among the at least two radiation sources. Using the radiation detector 60, by detecting at least one source of radiation that has passed through the subject 14, a pre-exposure image (first radiographic image) is acquired as a radiographic image during the pre-exposure process. Next, a region to be imaged of the subject 14, which is included in the acquired pre-exposure image, is identified, and based on the identified region to be imaged of the subject 14, radiation doses are weighted with respect to all of the radiation sources housed in the radiation output device 20. Thereafter, radiation is applied (main exposure process, second image capturing process) with respect to the subject 14 from the respective radiation sources in accordance with the aforementioned weightings, whereby a main exposure image (second radiographic image), which is a radiographic image by the main exposure process, is acquired.

The first embodiment differs from the second embodiment basically as described above. Next, the structure of the second embodiment shall be described in further detail below.

Figure 32B:
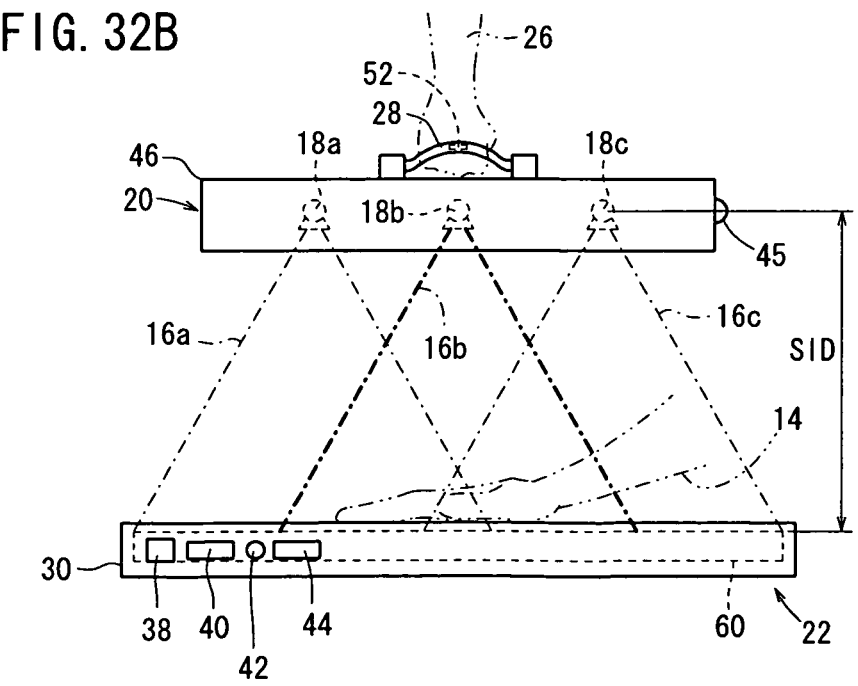

Concerning the second embodiment, FIGS. 31A and 31B show a case in which a chest region of the subject 14, as a comparatively large region to be imaged, is captured, whereas FIGS. 32A and 32B show a case in which a hand (right hand) region of the subject 14, as a comparatively small region to be imaged, is captured.

In the second embodiment, similar to the first embodiment, in the case that a portable radiation output device 20 is operated inside a hospital or at a location outside of the hospital, because securing a power supply may be difficult, preferably, each of the radiation sources 18a through 18c is a battery driven field-emission type radiation source. Accordingly, the respective radiation sources 18a through 18c are small in size and lightweight, and together therewith, the radiation output from the radiation sources 18a through 18c has a small radiation dose. Thus, at the location where image capturing is performed, the doctor 26 must locate the radiation output device 20 as closely as possible to the subject 14, such that capturing of radiographic images is carried out with respect to the subject 14 in a state where the source-to-image distance (SID) is short. As a result, because the radiation 16a through 16c emitted from the respective radiation sources 18a through 18c is applied within a narrow irradiation range, and exposure dose to the subject 14 is small, cases occur in which radiographic images (main exposure images) of an exposure dose suitable for diagnostic interpretation by the doctor 26 cannot be obtained.

Further, if it were possible to apply radiation to the subject 14 having a dose (exposure dose), which is suitable corresponding to the region to be imaged of the subject 14 and the thickness thereof, then a radiographic image suitable for diagnostic interpretation by the doctor 26 can be obtained, and unnecessary exposure of the subject 14 to such radiation can be avoided.

Consequently, according to the second embodiment, at least two radiation sources (three radiation sources 18a through 18c as shown in FIGS. 31A through 32B) are disposed in the radiation output device 20. In addition, upon capturing a radiographic image of the subject 14, first, a pre-exposure process is carried out, during which radiation (radiation 16b in FIGS. 31A and 32A) is applied at a comparatively small dose to the subject 14 from at least one radiation source (the central radiation source 18b shown in FIGS. 31A and 32A) from among the at least two radiation sources. Owing thereto, at least one source of radiation, which has passed through the subject 14, is detected by the radiation detector 60 and converted into a pre-exposure image as a radiation image taken during the pre-exposure process. Next, the region to be imaged of the subject 14 reflected in the obtained pre-exposure image is identified.

The radiation 16b of a comparatively small dose is defined as radiation of a dose sufficiently smaller than the exposure dose suitable for diagnostic interpretation by the doctor 26, and is a radiation dose of a degree that enables one to identify which region to be imaged among regions of the subject 14 is the region to be imaged of the subject 14 that is reflected in the pre-exposure image. In this manner, because pre-exposure is carried out only by the radiation 16b from one of the radiation sources 18b, the exposure dose applied to the region to be imaged of the subject 14 during the pre-exposure process can be minimized.

Further, during a pre-exposure process performed with respect to a comparatively large region to be imaged (the chest) shown in FIG. 31A, because radiation 16b is applied only to a portion of the chest, only the portion of the chest is reflected in the acquired pre-exposure image. However, assuming that a characteristic region (e.g., the lungs) of the chest is reflected in the pre-exposure image, since the chest region can be distinguished from other regions to be imaged of the subject 14, the region to be imaged shown in the pre-exposure image can be identified as being the chest region.

In the pre-exposure process with respect to a comparatively large region to be imaged, so that the region to be imaged of the subject 14 in the pre-exposure process can be identified more reliably, (1) the radiation source 18a may also be driven while radiation 16a, 16b of a comparatively small radiation dose is applied, (2) the radiation source 18c may be driven while radiation 16b, 16c of a comparatively small radiation dose is applied, or (3) all of the radiation sources 18a through 18c may be driven while radiation 16a through 16c of a comparatively small radiation dose is applied to the subject 14. Owing thereto, a pre-exposure image can be acquired in which the entire chest region is reflected. Further, as described later, by weighting the radiation doses during the main exposure process, the main exposure process can be carried out more reliably.

On the other hand, in a case where a pre-exposure image is taken with respect to a comparatively small region to be imaged (e.g., the right hand) as shown in FIG. 32A, because radiation 16b is applied to the entire right hand as a whole, the right hand is reflected properly and reliably in the acquired pre-exposure image. Accordingly, it is possible to easily identify that the region to be imaged shown in the pre-exposure image is the right hand. Further, even during a pre-exposure process, which is performed with respect to a comparatively small region to be imaged, naturally, the pre-exposure process can be carried out as in situations (1) through (3) above, to thereby acquire the pre-exposure image.

Next, according to the second embodiment, based on the region to be imaged of the subject 14 identified in the pre-exposure image, radiation doses are weighted with respect to all of the radiation sources housed in the radiation output device 20. Thereafter, radiation is applied (main exposure process) with respect to the subject 14 from the respective radiation sources in accordance with the aforementioned weightings, whereby a main exposure image, which is a radiographic image by the main exposure process, is acquired. More specifically, weighting of the radiation doses in the second embodiment is based roughly on the same concept by which the radiation doses were weighted in the first embodiment, however, as described below, the second embodiment differs in that weighting is carried out on the doses of radiation in a main exposure process, based on the region to be imaged of the subject 14 identified by the pre-exposure image.

More specifically, during image capturing (main exposure process) of the main exposure image with respect to a comparatively large region to be imaged (the chest) as shown in FIG. 31B, so that radiation 16a through 16c is applied to the entire chest region as a whole, it is required that radiation 16a through 16c be applied over a comparatively wide range (i.e., the entire imaging area 36). Additionally, concerning the cumulative exposure dose applied to the subject 14 in the main exposure process, an optimum radiation dose is needed (i.e., an exposure dose suitable for enabling diagnostic interpretation by the doctor 26) corresponding to the aforementioned chest region and the thickness thereof.

Consequently, with the second embodiment, during a main exposure process carried out with respect to a comparatively large region to be imaged as shown in FIG. 31B, weighting is carried out such that the doses of radiation 16a, 16c emitted from the radiation sources 18a, 18c at both ends are maximum (shown by the thick one-dot-dashed line in FIG. 31B), whereas the dose of radiation 16b emitted from the central radiation source 18b is smaller, of a degree sufficient to supplement any shortage of the maximum dose level (shown by the thin one-dot-dashed line in FIG. 31B). In accordance with such weightings, radiation 16a through 16c from the respective radiation sources 18a through 18c is irradiated simultaneously or sequentially.

In this case, as a matter of course, portions of the irradiation ranges of radiation (radiation 16a through 16c shown in FIG. 31B) emitted from adjacent radiation sources overlap mutually with each other, so that radiation is applied without gaps with respect to the region to be imaged of the subject 14.

On the other hand, with a main exposure image being captured (main exposure process) with respect to a comparatively small region (the right hand) as shown in FIG. 32B, since the right hand is positioned in a central portion inside of the imaging area 36, radiation 16a through 16c may be applied reliably only to a comparatively narrow area that includes the aforementioned central portion. In this case, the cumulative exposure dose with respect to the subject 14 during the main exposure process must be an optimum dose (i.e., an exposure does suitable for diagnostic interpretation by the doctor 26) corresponding to the right hand, the thickness thereof, etc.

Consequently, with the second embodiment, in the main exposure process with respect to the comparatively small region to be imaged shown in FIG. 32B, weighting is carried out such that the dose of radiation 16b at the central radiation source 18b is maximum (shown by the bold one-dot-dashed line in FIG. 32B), whereas the doses of radiation 16a, 16c emitted from the radiation sources 18a, 18c at both ends are smaller, of a degree sufficient to supplement any shortage of the maximum dose level (shown by the fine one-dot-dashed line in FIG. 32B). In accordance with such weightings, radiation 16a through 16c from the respective radiation sources 18a through 18c is irradiated simultaneously or sequentially.

In the above explanations, the maximum radiation dose is defined as a radiation dose that is comparatively largest in the case that the doses of radiation 16a through 16c are compared, and the small radiation dose is defined as a radiation dose that is comparatively smaller in the case that the doses of radiation 16a through 16c are compared, such that none of the doses is in excess of the optimum radiation dose. More specifically, according to the second embodiment, in the main exposure process of FIGS. 31B and 32B, the doses of radiation 16a through 16c emitted from the respective radiation sources 18a through 18c are weighted, such that the cumulative exposure dose, at the time that the subject 14 is exposed to radiation by respectively applying the radiation 16a through 16c, becomes the optimum dose.

Furthermore, according to the second embodiment, in the same manner as the first embodiment, since the time needed for image capturing of the subject 14 is shortened thereby, it is preferable for radiation 16a through 16c to be applied simultaneously from the respective radiation sources 18a through 18c. However, cases are known to occur in which it is difficult for radiation 16a through 16c to be applied simultaneously, in accordance with the ability to supply electric power to the radiation sources 18a through 18c (consumption of electric power in the radiation output device 20), or the image capturing conditions (number of images to be captured) of the subject 14.

In such cases, the radiation sources 18a through 18c may sequentially apply radiation 16a through 16c respectively, so as to reliably capture a radiographic image of the subject 14. If the radiation sources 18a through 18c sequentially apply radiation 16a through 16c respectively, then a central portion of the region to be imaged, which has been positioned, may be irradiated initially, and thereafter, other portions may be irradiated, with the aim of lessening blurring of the radiographic image, which may be caused by movement of the region to be imaged during the image capturing process. Alternatively, the region to be imaged may be irradiated initially with radiation, as indicated by the thick one-dot-dashed lines in FIGS. 31B and 32B, and then be irradiated with radiation, as indicated by the thin one-dot-dashed lines.

Accordingly, with the second embodiment, the ability to supply electric power with respect to each of the radiation sources 18a through 18c may be selected simultaneously or sequentially, responsive to the image capturing conditions of the subject 14.

In the case that radiation 16a through 16c, the doses of which have been weighted in the foregoing manner, is applied to the region to be imaged of the subject 14, radiation 16a through 16c that has passed through the region to be imaged is detected by the radiation detector 60 and converted into the main exposure image.

Figure 33:
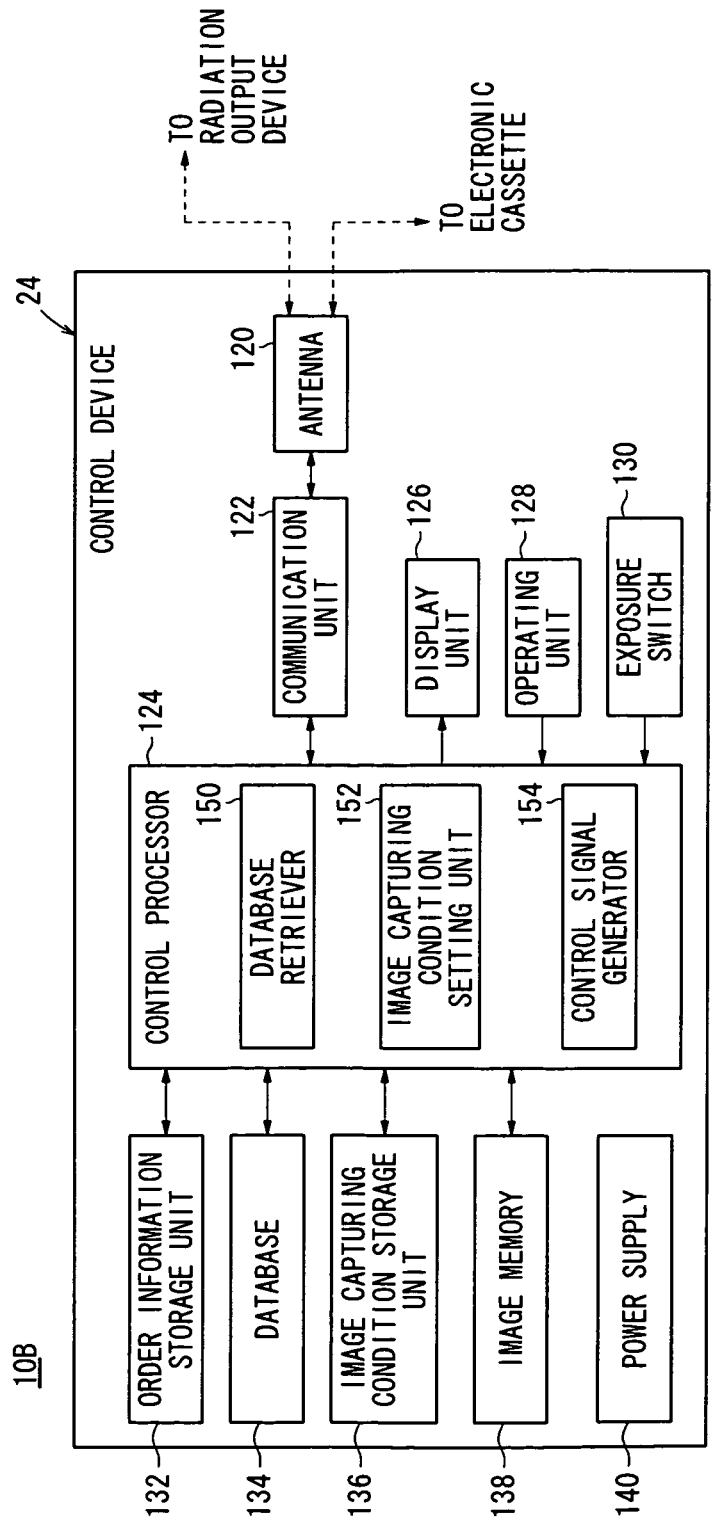
FIG. 33 is a block diagram of a control device of the second embodiment.

Among the radiation output device 20, the radiation detecting device 22 and the control device 24 that constitute the radiographic image capturing system 10B according to the second embodiment, the control device 24, as shown in FIG. 33, differs from the control device 24 of the radiographic image capturing system 10A according to the first embodiment, in that the addition processor 148 (see FIG. 8) is not included therein. In other aspects, the structure of the radiation output device 20 and the radiation detecting device 22 are the same as that of the radiation output device 20 and the radiation detecting device 22 (see FIG. 7) according to the first embodiment.

According to the second embodiment, pre-exposure conditions and main exposure conditions, which are exposure conditions for applying radiation 16a through 16c to the region to be imaged, are stored in the image capturing condition storage unit 136 of the control device 24. Further, the pre-exposure image and the main exposure image, which are radiographic images transmitted wirelessly from the radiation detecting device 22, are stored in the image memory 138. In the second embodiment as well, order information is stored in the order information storage unit 132, and various types of data relating to weighting of the radiation 16a through 16c are stored in the database 134. In particular, the object data and the tables shown in FIGS. 10 through 12 are stored in the database 134.

In the event that image capturing of a region to be imaged is carried out according to the second embodiment, the database retriever 150 performs the following processes.

First, in the pre-exposure process, the database retriever 150 also automatically retrieves, from the table shown in FIG. 11, optimum radiation dose data corresponding to the region to be imaged of the subject 14, the thickness thereof, and the image capturing technique therefor which are included in the order information, and the database retriever 150 determines an exposure dose, which is sufficiently smaller than the optimum exposure dose indicated by the retrieved optimum radiation dose data, as a radiation dose for the radiation 16b in the pre-exposure process. The database retriever 150 also outputs to the image capturing condition setting unit 152 data indicative of the determined radiation dose, and order information including the region to be imaged used for retrieval, the thickness thereof, and the image capturing technique therefor.

The database retriever 150 may display on the display unit 126, the optimum dose data, and the order information retrieved from the database 134. In this case, while confirming the content displayed on the display unit 126, the doctor 26 operates the operating unit 128 in order to enter the dose of the radiation 16b used during pre-exposure, whereupon the database retriever 150 outputs to the image capturing condition setting unit 152 the data (i.e., the dose of the radiation 16b used during pre-exposure) input by the doctor 26 and the order information.

On the other hand, during the main exposure process, the database retriever 150 automatically retrieves, from the database 134, object data that matches with the region to be imaged reflected in the pre-exposure image, and identifies the region to be imaged, which is indicated in the object data that matches with the aforementioned region to be imaged, as a region to be imaged of the subject 14 during the main exposure process. More specifically, the database retriever 150, using a known pattern matching method, carries out matching between the region to be imaged reflected in the pre-exposure image and each of the object data, and if the relationship (degree of matching) between the two images exceeds a predetermined threshold, then the region to be imaged, which is indicated by the object data for which the aforementioned threshold was exceeded, is identified as the region to be imaged of the subject 14 during the main exposure process.

In the case that a plurality of object data are retrieved from the database 134, for which there is a high possibility of matching with the region to be imaged reflected in the pre-exposure image (i.e., object data for which the degree of matching exceeded the aforementioned threshold), then the pre-exposure image and the plural object data may be displayed on the display unit 126. In this case, the doctor 26 confirms the content displayed on the display unit 126, and operates the operating unit 128 in order to select object data that appear to agree most closely with the region to be imaged. The database retriever 150 may then identify the region to be imaged indicated by the selected object data as the region to be imaged of the subject 14.

The database retriever 150 also identifies the thickness of the region to be imaged of the subject 14, and an image capturing technique therefor. More specifically, if the region to be imaged of the subject 14, which is included in the order information, and the identified region to be imaged of the subject 14 are in agreement with each other, then the database retriever 150 identifies the thickness of the region to be imaged of the subject 14 and the image capturing technique therefor, which are included in the order information, as the thickness of the region to be imaged of the subject 14 and the image capturing technique therefor in the main exposure process.

If the identified region to be imaged is not in agreement with the region to be imaged of the subject 14 that is included in the order information, or if the thickness of the region to be imaged and the image capturing technique therefor are desired to be reset, then the database retriever 150 may display the identified region to be imaged of the subject 14 and the order information on the display unit 126. In this case, the doctor 26 confirms the displayed content, and operates the operating unit 128 in order to enter a thickness of the region to be imaged and an image capturing technique therefor. Consequently, the database retriever 150 identifies the entered thickness of the region to be imaged of the subject 14 and the entered image capturing technique therefor, as the thickness of the region to be imaged of the subject 14 and the image capturing technique therefor in the main exposure process. The database retriever 150 can also store the identified region to be imaged and the identified thickness thereof, and the identified image capturing technique therefor as part of the order information in the order information storage unit 132, thereby editing the order information.

The database retriever 150 also automatically retrieves, from the table shown in FIG. 11, optimum radiation dose data corresponding to the identified region to be imaged of the subject 14, the thickness thereof, and the image capturing technique therefor. Further, the database retriever 150 automatically retrieves optimum weighting data based on the region to be imaged of the subject 14, the image capturing technique therefor, and the number of radiation sources used in the radiation output device 20. In addition, the database retriever 150 outputs to the image capturing condition setting unit 152 the retrieved optimum radiation dose data and weighting data, together with the order information including the region to be imaged of the subject, the thickness of the region to be imaged, and the imaging technique therefor, which have been used for retrieval.

If the database retriever 150 retrieves from the database 134 a plurality of candidates for the optimum radiation dose data and the weighting data, then the database retriever 150 may display the plural candidates and the order information on the display unit 126. The doctor 26, while confirming the content displayed on the display unit 126, can operate the operating unit 128 in order to select data that appears to be most optimum for the main exposure process. In this case, the database retriever 150 outputs to the image capturing condition setting unit 152 the optimum radiation dose data and the weighting data, which the doctor 26 has selected from among the plural candidates, and the order information.

Further, during the pre-exposure process, the image capturing condition setting unit 152 automatically sets image capturing conditions with respect to the region to be imaged of the subject 14 in the pre-exposure process as pre-exposure conditions, based on data indicative of the radiation dose determined by the database retriever 150, and the order information, and then stores the set pre-exposure conditions in the image capturing condition storage unit 136. Further, during the main exposure process, the image capturing condition setting unit 152, based on the optimum dose data and the weighting data retrieved by the database retriever 150, and the order information, automatically sets the image capturing conditions with respect to the region to be imaged of the subject 14 in the main exposure process as main exposure conditions, and stores the set main exposure conditions in the image capturing condition storage unit 136.

During the pre-exposure process, the image capturing condition setting unit 152 may display on the display unit 126 data indicative of the radiation dose and the order information. In this case, the doctor 26, while confirming the content displayed on the display unit 126, can operate the operating unit 128 so as to change the radiation dose corresponding to the order information, the state of the subject 14, or the image capturing technique, and the image capturing condition setting unit 152 sets the pre-exposure conditions based on the changed radiation dose.

Further, during the main exposure process, the image capturing condition setting unit 152 may display on the display unit 126 the order information, together with the optimum radiation dose data and the weighting data retrieved by the database retriever 150. In this case, the doctor 26, while confirming the content displayed on the display unit 126, can operate the operating unit 128 so as to change the optimum radiation dose data and the weighting data, corresponding to the order information, the state of the subject 14 or the image capturing technique, and the image capturing condition setting unit 152 sets the main exposure conditions based on the changed optimum radiation dose and the changed weighting data.

In the foregoing description, a case has been explained in which the database retriever 150 retrieves optimum radiation dose data from the database 134, and the image capturing condition setting unit 152 sets the main exposure capturing conditions based on the retrieved optimum radiation dose data and the like. However, in place of this explanation, after the region to be imaged of the subject 14, which is reflected in the pre-exposure image, has been identified, the database retriever 150 can calculate the optimum radiation dose corresponding to the region to be imaged, based on the image, which shows therein the identified region to be imaged. In this case, the database retriever 150 outputs to the image capturing condition setting unit 152 optimum radiation dose data indicated by the calculated optimum radiation dose, the weighting data retrieved from the database 134, and information indicative of the region to be imaged of the subject 14, whereupon the image capturing condition setting unit 152 sets the main exposure conditions based on such information.

[Operations of the Second Embodiment]

The radiographic image capturing system 10B according to the second embodiment is basically constructed as described above. Next, operations (a radiographic image capturing method) of the radiographic image capturing system 10B shall be described below with reference to the flowcharts shown in FIGS. 34 and 35.

Figure 34:
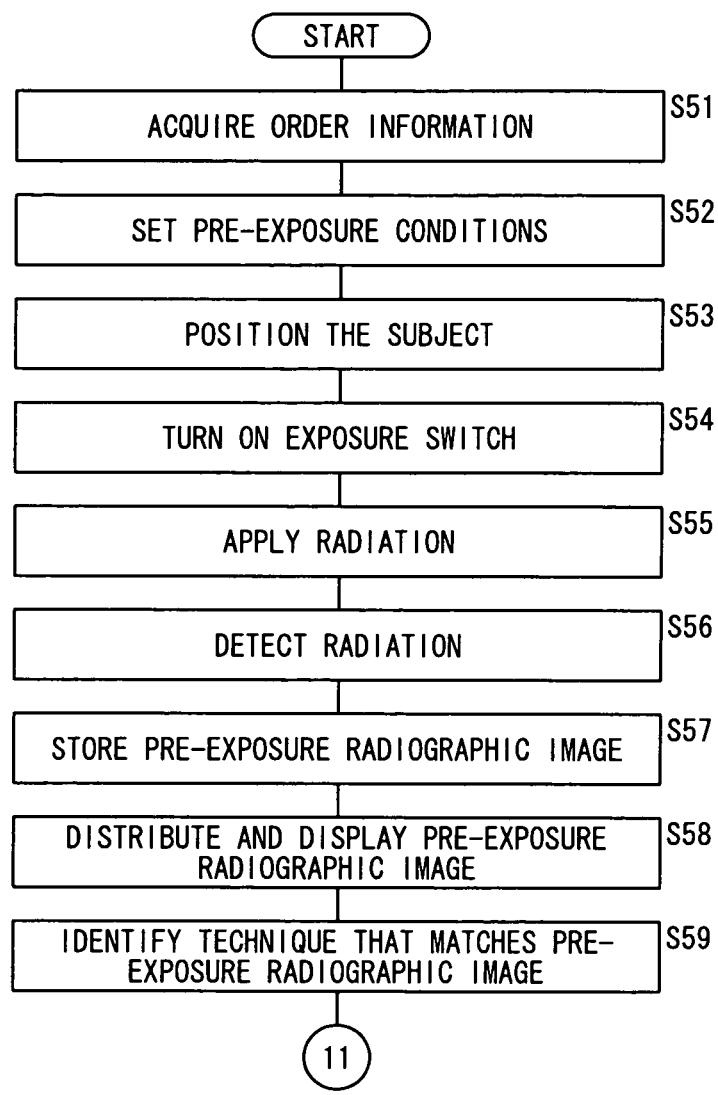
FIG. 34 is a flowchart of an operation sequence of the radiographic image capturing system according to the second embodiment.

In step S51 of FIG. 34, the control processor 124 (see FIG. 33) of the control device 24, similar to step S1 of FIG. 13, acquires order information from an external source, and the acquired order information is stored in the order information storage unit 132.

In step S52, the database retriever 150 automatically retrieves the region to be imaged, the thickness thereof, and the image capturing technique therefor, corresponding to the region to be imaged, the thickness, and the image capturing technique of the subject 14 (see FIGS. 1, 3A, 3B, 7, and 31A through 32B), which are included in the order information stored in the order information storage unit 132, and the optimum radiation dose data corresponding to such information, and determines an exposure dose, which is sufficiently smaller than the optimum radiation dose indicated by the retrieved optimum radiation dose data, as the dose of the radiation 16b in the pre-exposure process. Next, the image capturing condition setting unit 152 sets the pre-exposure conditions, based on the radiation dose determined by the database retriever 150 and the order information, and stores the set pre-exposure conditions in the image capturing condition storage unit 136.

If the order information does not include the thickness of the region to be imaged and the image capturing technique therefor in step S52, then the doctor 26 operates the operating unit 128 in order to enter the thickness of the region to be imaged and the image capturing technique therefor. The order information storage unit 132 stores the entered thickness of the region to be imaged and the entered image capturing technique as part of the order information, thereby editing the order information.

Further, in step S52, the database retriever 150 may display on the display unit 126 the retrieved optimum radiation dose data, and the order information. Owing thereto, the doctor 26, while confirming the content displayed on the display unit 126, can operate the operating unit 128 to enter the radiation dose of the radiation 16b applied in the pre-exposure process.

Furthermore, in step S52, the image capturing condition setting unit 152 may also display on the display unit 126 data indicative of the dose during pre-exposure, and the order information. Owing thereto, the doctor 26, while confirming the content displayed on the display unit 126, can operate the operating unit 128 to change the radiation dose corresponding to the order information, the state of the subject 14, and the image capturing technique.

Next, in step S53, similar to the case of step S3, in a case where the doctor 26 turns on the switch 38 of the radiation detecting device 22, the battery 76 supplies electric power to various components inside the radiation detecting device 22, thereby activating the radiation detecting device 22 in its entirety. Owing thereto, the cassette controller 74 sends an activation signal, which notifies that the radiation detecting device 22 has been activated, via a wireless link to the control device 24. The battery 76 also applies a bias voltage Vb to the respective pixels 90 of the radiation detector 60.

Based on receipt of the activation signal via the antenna 120 and the communication unit 122, the control processor 124 of the control device 24 sends the pre-exposure conditions, which are stored in the image capturing condition storage unit 136, to the radiation detecting device 22 via wireless communications. The cassette controller 74 records therein the image capturing conditions, which have been received via the antenna 70 and the communication unit 72.

In the case that the radiation output device 20 and the radiation detecting device 22 are placed in an integral condition and carried to a site, although at this time, the battery 76 is charging the battery 68 through the connection terminals 39, 41, 43, 45, in order for the doctor 26 to carry out positioning of the region to be imaged of the subject 14, the doctor 26 releases the connection terminals 39, 43 from interfitting engagement with each other, and also releases the connection terminals 41, 45 from interfitting engagement with each other. The radiation output device 20 then becomes separated from the radiation detecting device 22, whereby the radiation output device 20 and the radiation detecting device 22 are released from the integral condition, and at this time, the battery 76 stops charging the battery 68.

Then, the doctor 26 positions the region to be imaged of the subject 14, such that the central position of the region to be imaged of the subject 14 and the central position of the imaging area 36 become aligned with each other, and the region to be imaged of the subject 14 is included within the imaging area 36 (see FIGS. 3A and 3B). Thereafter, the doctor 26 grips the grip 28 and orients the radiation output device 20 toward the region to be imaged of the subject 14, so that the distance between the radiation output device 20 and the radiation detecting device 22 become equal to a distance depending on the SID, whereupon the touch sensor 52 outputs a detection signal to the radiation source controller 66. The radiation source controller 66 controls the battery 68 in order to supply electric power to various components of the radiation output device 20, thereby activating the radiation output device 20 in its entirety. Further, the radiation source controller 66 sends an activation signal, which notifies that the radiation output device 20 has been activated, via a wireless link to the control device 24. The control processor 124, based on receipt of the activation signal via the antenna 120 and the communication unit 122, sends wirelessly to the radiation output device 20 the pre-exposure conditions, which are stored in the image capturing condition storage unit 136. The radiation source controller 66 records therein the pre-exposure conditions received via the antenna 62 and the communication unit 64.

Provided that the above preparatory actions for the pre-exposure process have been completed, the doctor 26 grips the grip 28 with one hand and turns on the exposure switch 130 with the other hand (step S54). The control signal generator 154 generates an exposure control signal for starting emission of radiation 16b from the radiation source 18b, and sends the exposure control signal via a wireless link to the radiation output device 20 and the radiation detecting device 22. The exposure control signal at the time of pre-exposure is a synchronization control signal for capturing the pre-exposure image of the region to be imaged of the subject 14, as a result of synchronizing start of emission of radiation 16b from the radiation source 18b, and the detection and conversion of such radiation 16b into a radiographic image by the radiation detector 60.

Upon receipt of the exposure control signal by the radiation source controller 66, the radiation source controller 66 controls the radiation source 18b in order to apply a prescribed dose of radiation 16b to the subject 14 according to the pre-exposure conditions. The radiation source 18b emits radiation 16b, which is output from the radiation output device 20 and applied to the region to be imaged of the subject 14, for a given exposure time (irradiation time) based on the pre-exposure conditions (step S55).

In this case, if the region to be imaged is a chest region, as shown in FIG. 31A, then radiation 16b of a dose sufficiently smaller than the optimum radiation dose is applied to a portion of the chest region of the subject 14 from the central radiation source 18b. Further, if the region to be imaged is a right hand, as shown in FIG. 32A, then radiation 16b of a dose sufficiently smaller than the optimum radiation dose is applied to the right hand of the subject 14 as a whole from the central radiation source 18b.

In step S56, radiation 16b passes through the subject 14 and reaches the radiation detector 60 in the radiation detecting device 22. If the radiation detector 60 is of an indirect conversion type, then the scintillator of the radiation detector 60 emits visible light having an intensity depending on the intensity of the radiation 16b. The pixels 90 of the photoelectric conversion layer 96 convert the visible light into electric signals and store the electric signals as electric charges therein. The electric charges, which are stored in the pixels as representing a radiographic image (pre-exposure image) of the subject 14, are read as address signals, which are supplied from the address signal generator 78 of the cassette controller 74 to the line scanning driver 100 and the multiplexer 102.

Reading operations of the pre-exposure image are substantially the same as the reading operations for the radiographic image of step S6, and thus detailed explanation of such operations is omitted.

In step S57, the pre-exposure image, after having been stored in the image memory 80 of the cassette controller 74, and the cassette ID information, which is stored in the cassette ID memory 82, are sent to the control device 24 wirelessly via the communication unit 72 and the antenna 70. The control processor 124 of the control device 24 stores the pre-exposure image and the cassette ID information, which are received via the antenna 120 and the communication unit 122, in the image memory 138, and displays the pre-exposure image on the display unit 126 (step S58). Consequently, the doctor 26, by observing the displayed content on the display unit 126, can confirm that the pre-exposure image has been obtained.

Next, in step S59, the database retriever 150 retrieves automatically from the database 134 object data that matches with the region to be imaged, which is reflected in the pre-exposure image, and the region to be imaged, which is indicated by the object data that agree with the aforementioned region to be imaged, is identified as a region to be imaged of the subject 14 in the main exposure process.

Next, the database retriever 150 identifies the thickness and the image capturing technique in relation to the identified region to be imaged of the subject 14. In this case, if the region to be imaged of the subject 14 included in the order information stored in the order information storage unit 132 and the region to be imaged of the subject 14 identified by the database retriever 150 agree with one another, then the database retriever 150 identifies, as is, the thickness and the image capturing technique within the order information as the thickness and image capturing technique for the region to be imaged of the subject 14 in the main exposure process.

In step S59, if a plurality of object data are retrieved, having a degree of coincidence with the region to be imaged reflected in the pre-exposure image that has exceeded a predetermined threshold value, then the database retriever 150 may display the pre-exposure image and the plural object data on the display unit 126. The doctor 26 may confirm the content displayed on the display unit 126, and can operate the operating unit 128 in order to select object data that appear to be in agreement most closely with the region to be imaged in the pre-exposure image. The database retriever 150 then identifies the region to be imaged, which is represented by the object data selected by the doctor 26, as the region to be imaged of the subject 14.

Further, in step S59, if the region to be imaged of the subject 14, which is reflected in the pre-exposure image, is not in agreement with the region to be imaged of the subject 14 that is included in the order information, or if the thickness of the region to be imaged of the subject 14 and the image capturing technique therefor are to be reset, then the database retriever 150 may display on the display unit 126 the identified region to be imaged of the subject 14 and the order information. The doctor 26 can then confirm the content displayed on the display unit 126, and operate the operating unit 128 in order to enter the thickness of the region to be imaged of the subject 14, and an image capturing technique therefor. As a consequence, the database retriever 150 can identify the entered thickness of the region to be imaged of the subject 14 and the entered image capturing technique therefor, as the thickness of the region to be imaged of the subject 14 and the image capturing technique therefor in the main exposure process. Further, the database retriever 150 can store the identified region to be imaged, the thickness thereof and the image capturing technique therefor, as part of the order information in the order information storage unit 132, thereby editing the order information.

In step S60, the database retriever 150 automatically retrieves from the database 134, a region to be imaged of the subject 14, a thickness thereof, and an image capturing technique therefor, which correspond to the region to be imaged of the subject 14, the thickness thereof, and the image capturing technique therefor, which were identified in step S59, along with optimum radiation dose data corresponding to such items of information. Further, the database retriever 150 also automatically retrieves from the database 134 weighting data corresponding to the region to be imaged of the subject 14 that has been identified in step S59, and the image capturing technique therefor. Additionally, in step S61, the database retriever 150 outputs to the image capturing condition setting unit 152, as various data necessary for the main exposure process, the retrieved optimum dose data and the weighting data, and order information including the region to be imaged of the subject 14 used for retrieval, and the thickness and image capturing technique for the region to be imaged.

In step S60, if the database retriever 150 retrieves a plurality of candidates for the optimum radiation dose data and the weighting data, then the database retriever 150 displays the plural candidates and the order information on the display unit 126. In this case, the doctor 26 confirms the contents displayed on the display unit 126, and operates the operating unit 128 in order to select a candidate (data) that appears to be most optimum for the main exposure process. The database retriever 150 then outputs to the image capturing condition setting unit 152 the optimum radiation dose data and the weighting data, which the doctor 26 has selected, and the order information, as various data necessary for the main exposure process (step S61).

In step S62, the image capturing condition setting unit 152 sets main exposure conditions under which the region to be imaged of the subject 14 is to be irradiated with radiation 16*a* through 16*c* emitted from the radiation sources 18*a* through 18*c*, based on the entered optimum radiation dose data, the entered weighting data, and the order information.

If the region to be imaged of the subject 14 is a chest region as shown in FIG. 31B, then the image capturing condition setting unit 152 sets the main exposure conditions (tube voltages, tube currents, and irradiation times), such that the doses of radiation 16*a*, 16*c* emitted from the radiation sources 18*a*, 18*c* at both ends are of a maximum dose level, whereas the dose of radiation 16*b* emitted from the radiation source 18*b* at the center is of a lower dose level, sufficient to supplement any shortage of the maximum dose level, and stores the set main exposure conditions in the image capturing condition storage unit 136.

Further, if the region to be imaged of the subject 14 is a hand (right hand) as shown in FIG. 32B, then the image capturing condition setting unit 152 sets the main exposure conditions (tube voltages, tube currents, and irradiation times), such that the dose of radiation 16*b* emitted from the radiation source 18*b* at the center is of a maximum dose level, and the doses of radiation 16*a*, 16*c* emitted from the radiation sources 18*a*, 18*c* at both ends are of a lower dose level, sufficient to supplement any shortage of the maximum dose level, and stores the set main exposure conditions in the image capturing condition storage unit 136.

In addition, the control processor 124 sends the set main exposure conditions to the radiation output device 20 and the radiation detecting device 22 wirelessly via the communication unit 122 and the antenna 120. The radiation source controller 66 of the radiation output device 20 registers the main exposure conditions received via the antenna 62 and the communication unit 64, whereas the cassette controller 74 of the radiation detecting device 22 registers the main exposure conditions received via the antenna 70 and the communication unit 72.

In step S62, the image capturing condition setting unit 152 may display the entered optimum radiation dose data, the entered weighting data, and the order information on the display unit 126. The doctor 26 may then confirm the content displayed on the display unit 126, and by operating the operating unit 128, can change details of the optimum radiation dose data and the weighting data depending on the order information, the state of the subject 14, or the image capturing technique for the subject 14, as well as setting desired main exposure conditions in accordance with the contents of such data, which have been changed. In this case, the image capturing condition setting unit 152 stores the set main exposure conditions in the image capturing condition storage unit 136.

Further, in the case that, in step S60, the database retriever 150, after having identified the region to be imaged of the subject 14 reflected in the pre-exposure image, calculates an optimum radiation dose corresponding to the region to be imaged based on the image in which the region to be imaged is shown, and retrieves weighting data from the database 134, then in step S62, the image capturing condition setting unit 152 sets the main exposure conditions based on the information indicative of the region to be imaged of the subject 14, the optimum radiation dose data indicative of the calculated optimum radiation dose, and the retrieved weighting data.

Provided that the above preparatory actions for the main exposure process have been completed, the doctor 26 grips the grip 28 with one hand and turns on the exposure switch 130 again with the other hand (step S63). The control signal generator 154 generates an exposure control signal for starting emission of radiation 16*a* through 16*c* from the radiation sources 18*a* through 18*c*, and sends the exposure control signal via a wireless link to the radiation output device 20 and the radiation detecting device 22. The exposure control signal of the main exposure process is a synchronization control signal for capturing a main exposure image of the region to be imaged of the subject 14, as a result of synchronizing start of emission of radiation 16*a* through 16*c* from the radiation sources 18*a* through 18*c*, and the detection and conversion of such radiation 16*a* through 16*c* into a radiographic image by the radiation detector 60.

Upon receipt of the exposure control signal, the radiation source controller 66 controls the radiation sources 18*a* through 18*c* in order to apply prescribed doses of radiation 16*a* through 16*c* to the subject 14 according to the main exposure conditions. The radiation sources 18*a* through 18*c* emit radiation 16*a* through 16*c* respectively, which is output from the radiation output device 20 and applied to the region to be imaged of the subject 14, for a given exposure time (irradiation time) based on the main exposure conditions (step S64).

In this case, if the region to be imaged is a chest region as shown in FIG. 31B, then large doses of radiation 16*a*, 16*c* are applied to the chest region of the subject 14 from the radiation sources 18*a*, 18*c* at both ends, whereas a smaller dose of radiation 16*b* sufficient to compensate for any shortage of the large radiation dose is applied to the region to be imaged from the central radiation source 18*b*.

Further, if the region to be imaged is a right hand as shown in FIG. 32B, then a large dose of radiation 16*b* is applied to the region to be imaged of the subject 14 from the central radiation source 18*b*, whereas smaller doses of radiation 16*a*, 16*c* sufficient to compensate for any shortage of the large radiation dose are applied to the right hand of the subject 14 from the radiation sources 18*a*, 18*c* at both ends.

Additionally, in step S65, after the radiation 16*a* through 16*c* has passed through the subject 14 and reached the radiation detector 60 of the radiation detecting device 22, in the case that the radiation detector 60 is a detector of an indirect conversion type, the scintillator constituting the radiation detector 60 emits visible light of an intensity corresponding to the intensity of the radiation 16*a* through 16*c*, whereupon the respective pixels 90 of the photoelectric conversion layer 96 convert the visible light into electric signals, which are stored as charges. Then, the electric charge information, which is stored in each of the pixels 90 as representing a radiographic image (main exposure image) of the subject 14, is read by address signals, which are supplied from the address signal generator 78 of the cassette controller 74 to the line scanning driver 100 and the multiplexer 102.

The main exposure image, which is made up of the read electric charge information, is stored in the image memory 80 of the cassette controller 74 (step S66), and the main exposure image, which is stored in the image memory 80, and the cassette ID information, which is stored in the cassette ID memory 82, are sent to the control device 24 wirelessly via the communication unit 72 and the antenna 70. The control processor 124 of the control device 24 stores the radiographic image and the cassette ID information, which are received via the antenna 120 and the communication unit 122, in the image memory 138, and displays the main exposure image on the display unit 126 (step S67).

The processes of steps S65 through S67 related to the main exposure image are substantially the same as the processes of steps S56 through S58 related to the pre-exposure image. More specifically, since the explanation of steps S65 through S67 can be reproduced simply by replacing terms related to the pre-exposure image in the explanation of steps S56 through S58 with terms related to the main exposure image, detailed explanation of steps S65 through S67 has been omitted herein.

After having confirmed that a main exposure image has been obtained by visually checking the content displayed on the display unit 126, the doctor 26 releases the subject 14 from the positioned condition, and removes the hand from the grip 28. Owing thereto, the touch sensor 52 stops outputting the detection signal, and the radiation source controller 66 stops supplying electric power from the battery 68 to the various components of the radiation output device 20. As a result, the radiation output device 20 is brought into a sleep mode or is shut down. Further, if the doctor 26 presses (turns off) the switch 38, then the battery 76 stops supplying electric power to the various components of the radiation detecting device 22, and thus the radiation detection device 22 is brought into a sleep mode or is shut down.

Then, the doctor 26 brings the connection terminals 39, 43 into interfitting engagement with each other, and also brings the connection terminals 41, 45 into interfitting engagement with each other, thereby holding the radiation output device 20 between the holders 35, 37, so as to integrally combine the radiation output device 20 and the radiation detecting device 22 with each other (see FIG. 2A).

[Advantages of the Second Embodiment]

As described above, with the radiographic image capturing system 10B and the radiographic image capturing method according to the second embodiment, among the at least two radiation sources (i.e., the three radiation sources 18*a* through 18*c* shown in FIGS. 31A through 32B) housed in the radiation output device 20, the pre-exposure process is carried out with respect to the subject 14 by at least one of the radiation sources (i.e., the radiation source 18*b* shown in FIGS. 31A through 32B). Based on the pre-exposure image obtained by the pre-exposure process, weighting is carried out on radiation (radiation 16*a* through 16*c*) emitted respectively from at least two radiation sources during the main exposure process.

In the foregoing manner, according to the second embodiment, an irradiation range of the radiation is not set simply by enabling the region to be imaged of the subject 14 to be covered, but rather, based on the pre-exposure image, which is acquired by a pre-exposure process carried out prior to the main exposure process, the respective radiation doses of radiation emitted from the respective radiation sources are weighted during the main exposure process. In addition, since the region to be imaged of the subject 14 is reflected in the pre-exposure image, weighting can be performed on each of the radiation doses in accordance with the region to be imaged.

Accordingly, with the second embodiment, even if image capturing of a radiographic image (main exposure process) is carried out with respect to the subject 14 at a short SID using field-emission radiation sources, the irradiation range of the radiation can easily be enlarged, and radiation can be applied at an optimum radiation dose (exposure dose) with respect to the subject 14. In this manner, with the second embodiment, because radiation can be applied to the subject 14 at an optimum dose corresponding to the subject 14, a radiographic image (main exposure image) suitable for diagnostic interpretation by a doctor can be obtained, and unnecessary exposure of the subject 14 to radiation can be avoided.

Further, the database retriever 150 identifies the region to be imaged of the subject 14, which is represented by the object data that agree with the region to be imaged of the subject 14 and which is reflected in the pre-exposure image, as a region to be imaged of the subject 14 for the main exposure process. The database retriever 150 then retrieves optimum radiation dose data depending on the identified region to be imaged, the thickness thereof, and the image capturing technique therefor, and together therewith, retrieves weighting data depending on the region to be imaged of the subject 14 and the image capturing technique. Thereafter, the database retriever 150 outputs the retrieved optimum radiation dose data, the retrieved weighting data, and the order information to the image capturing condition setting unit 152. The image capturing condition setting unit 152 is thus capable of setting the main exposure conditions accurately and efficiently. As a result, as long as the radiation output device 20 applies radiation 16a through 16c from the respective radiation sources 18a through 18c to the region to be imaged of the subject 14 according to the main exposure conditions, capturing of a main exposure image can be performed at an optimum exposure dose with respect to the region to be imaged of the subject 14.

Further, after the database retriever 150 has identified the region to be imaged of the subject 14 reflected in the pre-exposure image, because it is possible to calculate an optimum radiation dose corresponding to the region to be imaged based on the image in which the identified region to be imaged is shown, in the case that the optimum radiation dose data is not stored in the database 134, or even if desired optimum radiation dose data cannot be retrieved from the database 134, the optimum radiation dose for the main exposure process can be identified, and based on the identified optimum radiation dose, the main exposure conditions can be set in the image capturing condition setting unit 152.

Furthermore, the database retriever 150, based on the order information, determines a radiation dose for the radiation 16b during the pre-exposure process, which is sufficiently smaller than the optimum exposure dose during the main exposure process, and the image capturing condition setting unit 152 sets pre-exposure conditions based on the radiation dose determined by the database retriever 150 and the order information. Owing thereto, if the radiation output device 20 applies radiation 16b to the region to be imaged of the subject 14 from the radiation source 18b in accordance with the pre-exposure conditions, capturing of the pre-exposure image can be performed at a sufficiently small exposure dose with respect to the region to be imaged of the subject 14. Moreover, during pre-exposure, by applying the radiation 16b from the one radiation source 18b to the region to be imaged of the subject 14, the exposure dose with respect to the region to be imaged during the pre-exposure process can be minimized.

Further, assuming that the region to be imaged of the subject 14 is positioned at a center portion of the imaging area 36 (see FIGS. 3A and 3B), during the pre-exposure process, radiation 16b is applied toward the region to be imaged of the subject 14 from the central radiation source 18b of the radiation output device 20 that confronts the aforementioned center portion. Thus, a pre-exposure image can reliably be acquired in which the region to be imaged is reflected.

Furthermore, by changing the content of the optimum dose data and the weighting data, which were retrieved by the database retriever 150 corresponding to the order information, the condition of the subject 14 or the image capturing technique for the subject 14, more accurate main exposure conditions can be set corresponding to the actual image capturing technique for the subject 14.

Still further, with the second embodiment, in the case that three radiation sources 18a through 18c are housed in the radiation output device 20, during the main exposure process, weighting of the radiation doses of radiation 16a through 16c emitted respectively from the radiation sources 18a through 18c corresponding to the region to be imaged of the subject 14 is carried out in the following manner.

In a case where the main exposure process is carried out with respect to a comparatively large region to be imaged (e.g., the chest region of the subject 14), as shown in FIG. 31B, weighting on the radiation 16a through 16c emitted respectively from the radiation sources 18a through 18c is carried out such that maximum doses of radiation 16a, 16c are applied from the radiation sources 18a, 18c at both ends, whereas a smaller dose of radiation 16b is applied from the central radiation source 18b.

In a case where the main exposure process is carried out with respect to a comparatively small region to be imaged (e.g., a hand of the subject 14), as shown in FIG. 32B, weighting on the radiation 16a through 16c emitted respectively from the radiation sources 18a through 18c is carried out such that a large dose of radiation 16b is applied from the central radiation source 18b, whereas smaller doses of radiation 16a, 16c are applied from the radiation sources 18a, 18c at both ends.

By carrying out weighting in the foregoing manner, even if image capturing of a radiographic image is carried out with respect to the subject 14 at a short SID using field-emission radiation sources 18a through 18c, the irradiation range of the radiation 16a through 16c can easily be enlarged, and radiation 16a through 16c can be applied at an optimum radiation dose (exposure dose) with respect to the subject 14. In this manner, because radiation 16a through 16c can be applied to the subject 14 at an optimum dose corresponding to the subject 14, a radiographic image suitable for diagnostic interpretation by a doctor 26 can be obtained, and unnecessary exposure of the subject to radiation can be avoided.

Further, in the example of FIG. 31B, a radiographic image can be captured highly efficiently with respect to a comparatively large region to be imaged, whereas in the example of FIG. 32B, a radiographic image can be captured highly efficiently with respect to a comparatively small region to be imaged.

The radiographic image capturing system 10B according to the second embodiment is constituted by the same structural elements as the radiographic image capturing system 10A according to the first embodiment, and therefore, by providing such structural elements, it is a matter of course that the same advantages and effects of the first embodiment can be obtained.

For example, the second embodiment can be applied to a construction in which two radiation sources 18a, 18b are accommodated in the radiation output device 20, as in the first modification (see FIGS. 15A and 15B).

In this case, in a case where image capturing of the chest shown in FIG. 15A, and image capturing of the hand shown in FIG. 15B are performed, during the pre-exposure process, (1) radiation 16a is applied to the subject 14 from the radiation source 18a, (2) radiation 16b is applied to the subject 14 from the radiation source 18b, or (3) radiation 16a, 16b is applied to the subject 14 respectively from each of the radiation sources 18a, 18b. In cases (1) and (2), although only a portion of the region to be imaged (the chest, the hand) is reflected in the obtained pre-exposure image, assuming that a characteristic location of the region to be imaged is included therein, the region to be imaged can be distinguished from other regions to be imaged of the subject 14. Further, in case (3), since the entire region to be imaged is reflected in the pre-exposure image, it is easy to identify the region to be imaged.

On the other hand, during the main exposure process, radiation 16a, 16b may be applied to the subject 14 respectively from each of the radiation sources 18a, 18b. During the main exposure process, it is a matter of course that weighting should be carried out respectively on the radiation 16a, 16b based on the pre-exposure image.

In this manner, even in the case that the second embodiment is applied to the first modification, in which only two radiation sources 18a, 18b are housed in the radiation output device 20, by carrying out the pre-exposure process to thereby acquire a pre-exposure image, it is a matter of course that the advantages and effects of the second embodiment can be obtained.

As described above, according to the second embodiment, as examples thereof, cases have been described in which a pre-exposure image is acquired, and doses of radiation emitted from two radiation sources 18*a*, 18*b* or three radiation sources 18*a* through 18*c* are weighted. However, even with four or more radiation sources, by applying the principles of the second embodiment, the advantages and effects of the second embodiment can easily be obtained.

[Modifications of Second Embodiment]

Next, modifications of the second embodiment (twelfth and thirteenth modifications) are explained with reference to FIGS. 36 through 39.

In the following modifications, structural elements thereof, which are the same as those shown in FIGS. 1 through 35, are designated by the same reference numerals and detailed description of such features is omitted.

[Twelfth Modification]

Figure 36:
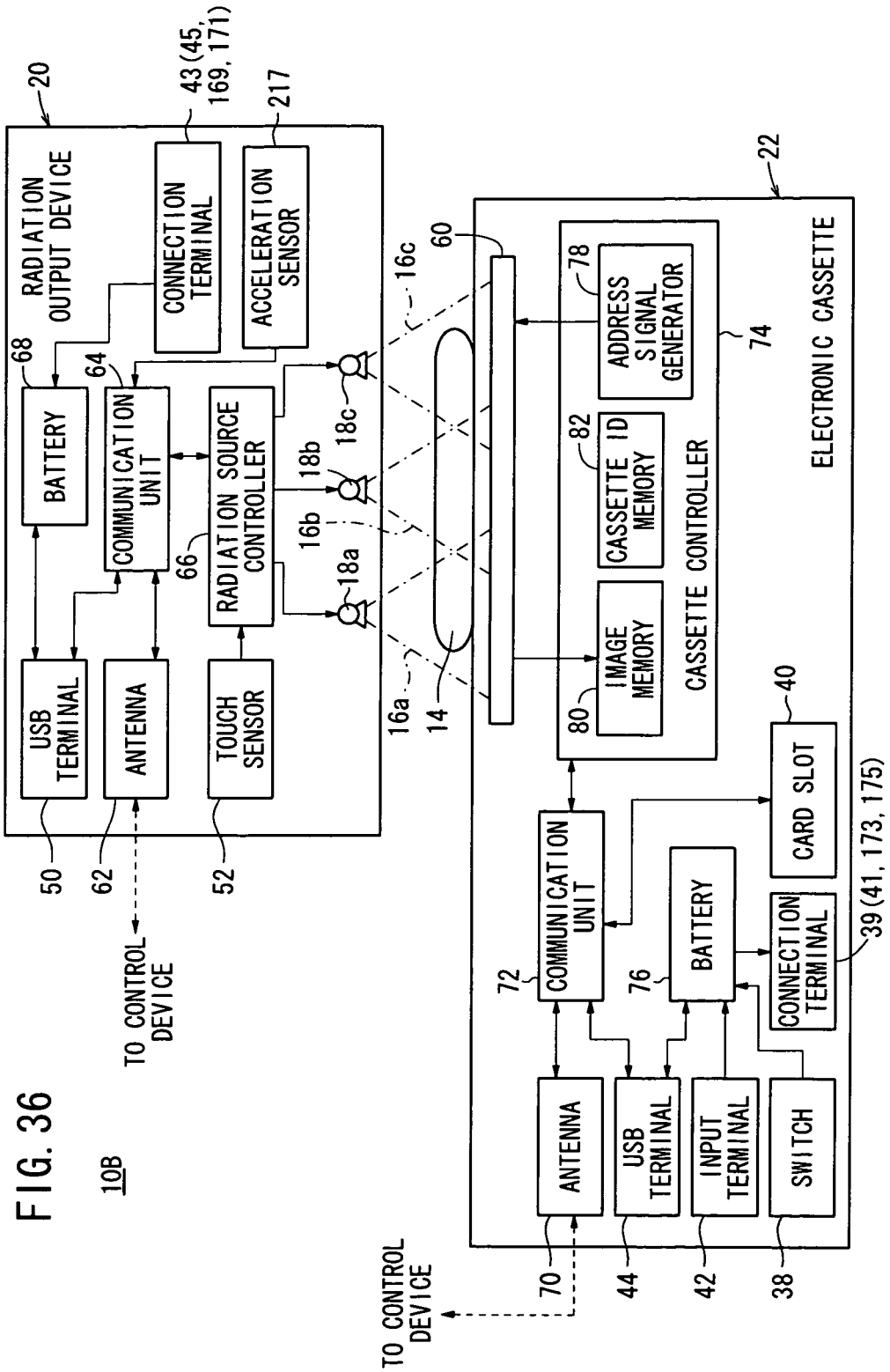
FIG. 36 is a block diagram showing a radiographic image capturing system according to a twelfth modification.
Figure 37:
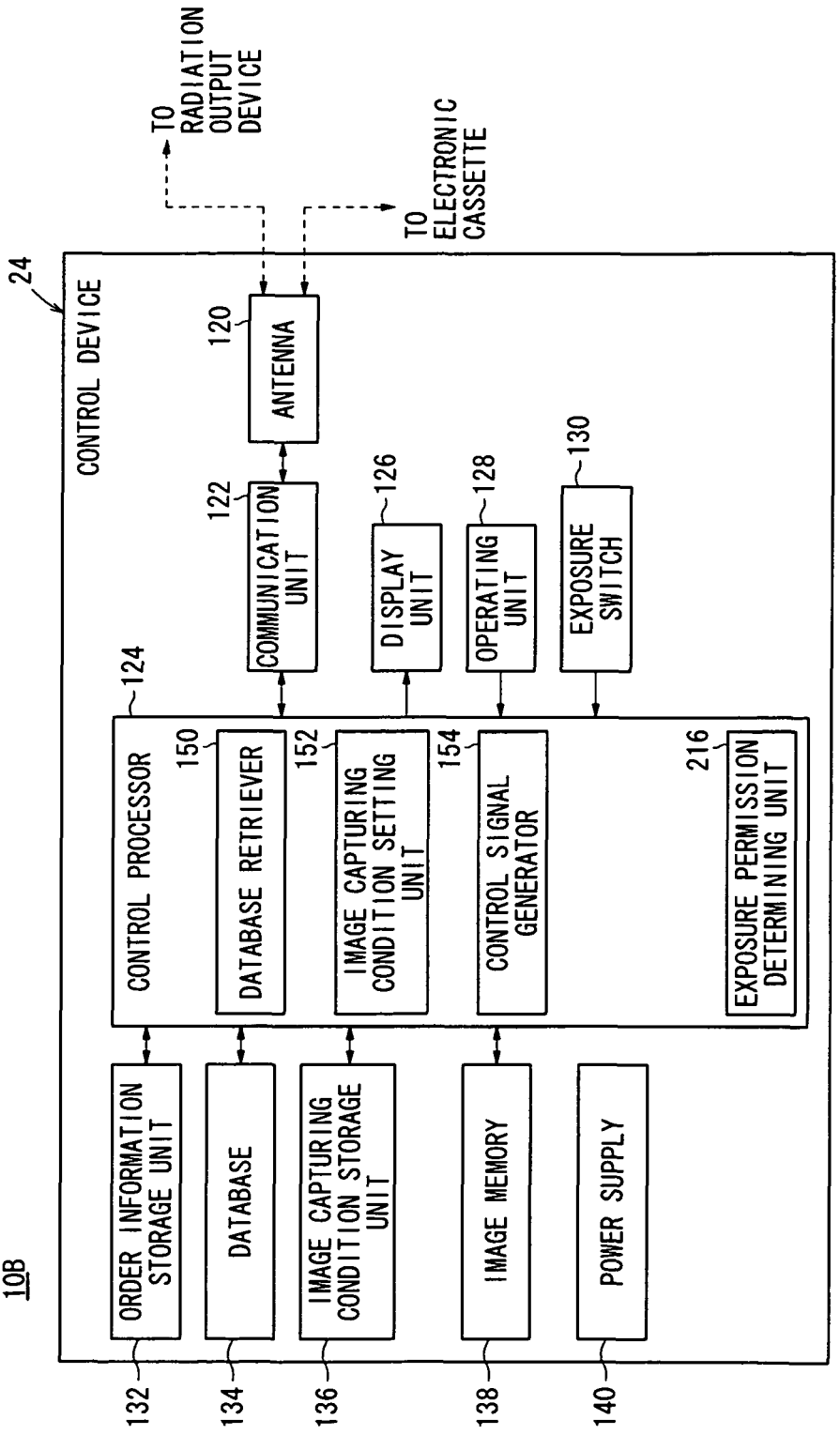
FIG. 37 is a block diagram showing a radiographic image capturing system according to a twelfth modification.

According to a twelfth modification, as shown in FIGS. 36 and 37, an acceleration sensor 217 is incorporated in the radiation output device 20. In addition, the control processor 124 of the control device 24 further includes an exposure permission determining unit 216.

In this case, based on acceleration of the radiation output device 20, which is indicated by a detection signal of the acceleration sensor 217 sent to the control device 24, the exposure permission determining unit 216 determines whether emission (pre-exposure) of radiation 16*a* through 16*c* from each of the radiation sources 18*a* through 18*c* is permitted or interrupted. In this case, in the event that the exposure permission determining unit 216 determines that the acceleration indicated by the detection signal received via the antenna 120 and the communication unit 122 has exceeded a predetermined threshold, it is determined to interrupt the pre-exposure process, and the doctor 26 is notified through the display unit 126 of interruption of the pre-exposure process. The aforementioned threshold is defined as an acceleration that is large enough to be indicative of wobbling of the radiation output device 20, of a degree such that the pre-exposure process cannot accurately or reliably be carried out.

Furthermore, the exposure permission determining unit 216 is capable of calculating an amount of wobbling (blurring) of the region to be imaged of the subject 14 in the pre-exposure image. In the event that the amount of blurring is determined to have exceeded a predetermined threshold, the exposure permission determining unit 216 may report (indicate) that the main exposure process should be interrupted and that the pre-exposure process should be carried out again. The threshold is defined as an amount of wobbling (blurring) of the region to be imaged of a degree such that the region to be imaged cannot be identified in identifying of the region to be imaged of the subject 14 reflected in the pre-exposure image, or an amount of wobbling (blurring) of the region to be imaged of a degree such that the weighting process cannot reliably be performed in a case where weighting is carried out on the respective doses of radiation 16*a* through 16*c*. Further, wobbling of the region to be imaged in the pre-exposure image includes a situation in which the region to be imaged in the pre-exposure image becomes blurred due to wobbling of the radiation output device 20 during the pre-exposure process.

Next, the twelfth modification shall be described in detail with reference to the flowchart of FIGS. 38 and 39.

Figure 38:
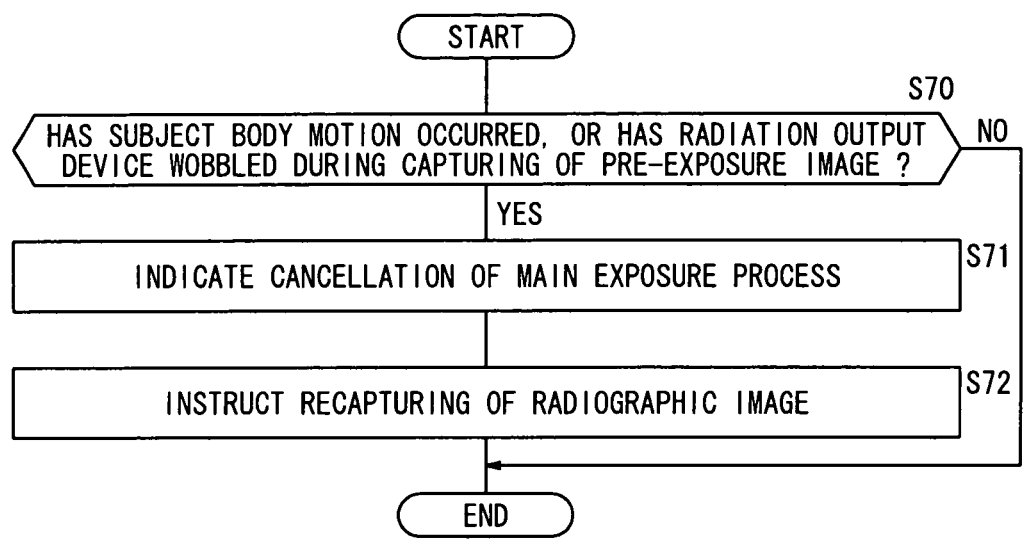
FIG. 38 is a flowchart of an operation sequence of the radiographic image capturing system according to the twelfth modification.

In FIG. 38, after the pre-exposure process, it is determined in the exposure permission determining unit 216 whether or not to interrupt the main exposure process and to carry out recapturing of the pre-exposure image, based on the acceleration of the radiation output device 20 during the pre-exposure process, or the amount of wobbling (blurring) of the region to be imaged of the subject 14 as reflected in the pre-exposure image.

During the pre-exposure process, the acceleration sensor 217 sequentially detects the acceleration of the radiation output device 20, and sequentially sends detection signals representing the detected acceleration to the control device 24 wirelessly. The exposure permission determining unit 216 sequentially registers data of the acceleration indicated by the sequentially received detection signals.

Additionally, in step S70 after completion of the pre-exposure process, the exposure permission determining unit 216 determines whether or not acceleration data exists among the registered acceleration data, which is in excess of a predetermined threshold. Further, the exposure permission determining unit 216 calculates the amount of wobbling (blurring) of the region to be imaged of the subject 14 in the pre-exposure image, and determines whether the calculated amount of wobbling has exceeded a predetermined threshold.

In the case that acceleration data is found in excess of the predetermined threshold, or if the amount of wobbling of the region to be imaged exceeds the predetermined threshold (step S70: YES), then the exposure permission determining unit 216 determines that wobbling of the radiation output device 20, or wobbling (movement) of the region to be imaged of the subject 14 has occurred during the pre-exposure process, which could adversely influence the pre-exposure image.

In step S71, the exposure permission determining unit 216 notifies the doctor 26 through the display unit 126 that the pre-exposure process has been suspended. Further, the exposure permission determining unit 216 indicates via the display unit 126 that the pre-exposure process should be carried out again (step S72). The doctor 26, by visually confirming the content displayed on the display unit 126, grasps that the pre-exposure process has failed, step S52 (see FIG. 34) is returned to, and the doctor 26 undertakes preparations to recapture the pre-exposure image.

On the other hand, in step S70, if acceleration data does not exist among the acceleration data registered in the exposure permission determining unit 216, which is in excess of a predetermined threshold, or if the amount of wobbling of the region to be imaged does not exceed the predetermined threshold (step S70: NO), then the exposure permission determining unit 216 determines that wobbling of the radiation output device 20 or movement of the region to be imaged has not occurred that could adversely influence the pre-exposure image. As a result, in the control device 24, implementation of step S59 is enabled, and the routine proceeds to undertake preparations for carrying out the main exposure process.

In this manner, with reference to the flowchart of FIG. 38, if the degree of acceleration of the radiation output device 20 during the pre-exposure process, or wobbling of the region to be imaged of the subject 14 during the pre-exposure process is of a degree that could adversely influence the pre-exposure image, then a notification (instruction) is issued to suspend the main exposure process and to carry out the pre-exposure process again, and thus the main exposure image can be acquired reliably.

Figure 39:
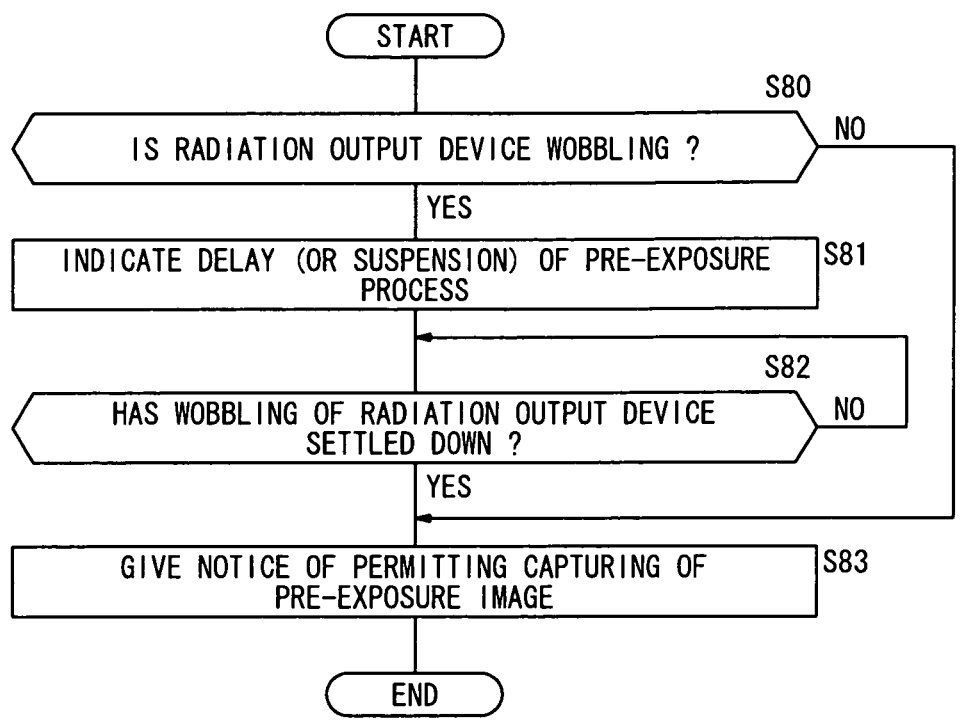
FIG. 39 is a flowchart of another operation sequence of the radiographic image capturing system according to the twelfth modification.

In FIG. 39, in the case that wobbling of the radiation output device 20 already occurs during preparations for the pre-exposure process (prior to application of radiation 16*a* through 16c), the pre-exposure process may be delayed or suspended, and thereafter, the pre-exposure process can be permitted once such wobbling has settled down.

More specifically, as shown in the flowchart of FIG. 39, the acceleration sensor 217 detects the acceleration of the radiation output device 20 during preparations for the pre-exposure process, and a detection signal indicative of the detected acceleration is sent wirelessly to the control device 24. In this case, in step S80, the exposure permission determining unit 216 determines whether or not the acceleration indicated by the received detection signal has exceeded a predetermined threshold.

In a case where the acceleration has exceeded the predetermined threshold, the exposure permission determining unit 216 determines that wobbling of the radiation output device 20 has occurred that could adversely influence the pre-exposure image (step S80: YES), and then determines that the pre-exposure process should be delayed or suspended.

Next, in step S81, the exposure permission determining unit 216 notifies the doctor 26 through the display unit 126 that the pre-exposure process has been delayed or suspended.

After the notification of step S81, the acceleration sensor 217 sequentially detects the acceleration, and the detection signal indicative of the acceleration is transmitted via a wireless link continuously to the control device 24.

Accordingly, in step S82, the exposure permission determining unit 216 determines whether or not the acceleration indicated by the received detection signal is lower than the predetermined threshold, and more specifically, determines whether wobbling of the radiation output device 20 held by the doctor 26 has settled down sufficiently. If the acceleration is lower than the aforementioned threshold and it is determined that wobbling has settled down (step S82: YES), then the exposure permission determining unit 216 displays on the display unit 126 a notification to the effect that delay or suspension of the pre-exposure process has been released, and capturing of the pre-exposure image is permitted (step S83). The doctor 26, by confirming the content displayed on the display unit 126, grasps that permission has been granted to perform the pre-exposure process, and that implementing of step S53 (see FIG. 34) is enabled.

Further, in step S80, in the case that wobbling of the radiation output device 20 is not generated, then since wobbling that could adversely influence the pre-exposure image has not occurred, the exposure permission determining unit 216 judges that there is no problem for the pre-exposure process to be carried out (step S80: NO) and implements the process of step S83.

According to the flowchart of FIG. 39, because a pre-exposure image can be acquired reliably, as a result thereof, capturing and acquisition of the main exposure image can be performed reliably as well.

[Thirteenth Modification]

Figure 40A:
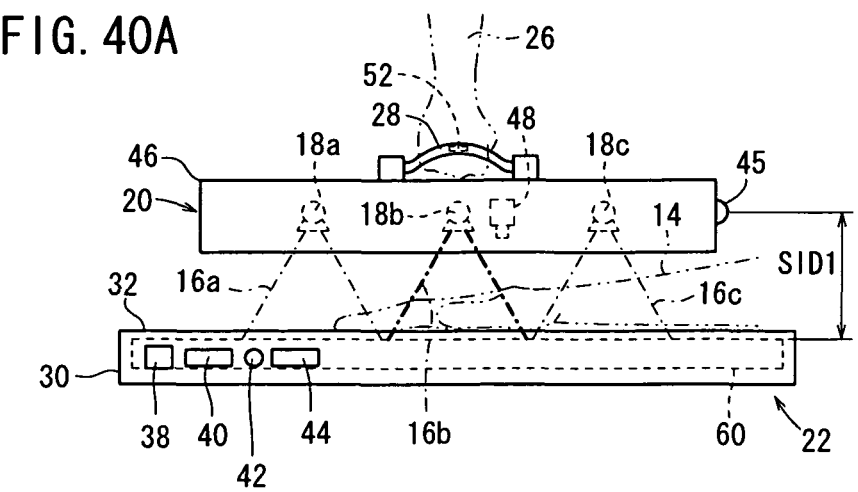
FIGS. 40A and 40B are side elevational views illustrating a situation in which a thirteenth modification is applied to the first and second embodiments, whereby application of radiation is implemented with respect to a region to be imaged of the subject.
Figure 40B:
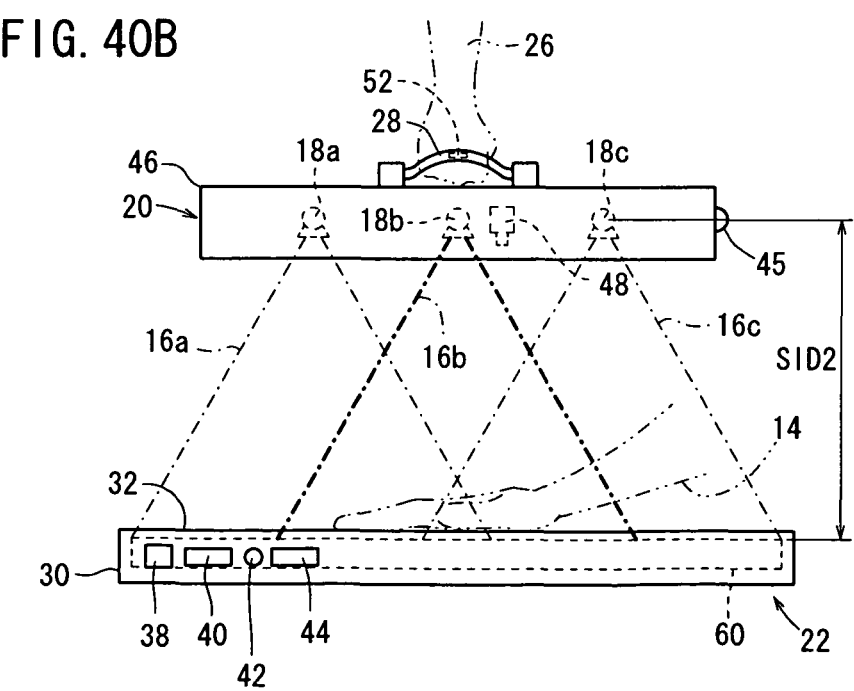

Incidentally, in the first and second embodiments, in the case that the SID is set by moving the radiation output device 20 while the grip 28 is being gripped by the doctor 26, if the radiation output device 20 is made to approach the subject 14 too closely, then as shown in FIG. 40A, the SID (the distance SID1 shown in FIG. 40A) becomes too short, and cases occur in which image capturing cannot be carried out with respect to the subject 14 except within a comparatively narrow range. Further, if the SID is too short, then the respective irradiation ranges of the radiation 16a through 16c will not be overlapped on the irradiated surface 32, resulting in the possibility that image capturing with respect to the subject 14 will fail.

Consequently, according to the thirteenth modification, the structure of the eighth, ninth and twelfth modifications (see FIGS. 23, 24, 26, 36 and 37) is utilized, whereby based on the acceleration of the radiation output device 20 detected by the acceleration sensor 217, an amount of movement of the radiation output device 20 is calculated, and it is judged whether or not the SID is set at an appropriate distance based on the calculated amount of movement. Then, application of radiation 16a through 16c is permitted, or application of radiation 16a through 16c is started at a point in time that the SID becomes set at the appropriate distance.

More specifically, in the case that the doctor 26 grips the grip 28 and thereby adjusts the SID, the acceleration sensor 217 detects the acceleration of the radiation output device 20 successively, and the control processor 124 calculates the amount of movement of the radiation output device 20 based on the acceleration detected by the acceleration sensor 217. In the exposure permission determining unit 216, in the event that the amount of movement calculated by the control processor 124 reaches a movement amount corresponding to an appropriate SID (e.g., the source-to-image distance SID2 shown in FIG. 40B) for capturing an image of the subject 14, output of radiation 16a through 16c (the recapturing process in the first embodiment or the main exposure process in the second embodiment) from each of the radiation sources 18a through 18c is permitted. Consequently, image capturing over a comparatively wide range can be carried out with respect to the subject 14, and image capturing failures with respect to the subject 14 can be avoided.

According to the thirteenth modification, (1) output of radiation 16a through 16c from the respective radiation sources 18a through 18c may be started by the doctor 26 pressing the exposure switch 130 after the recapturing process or the main exposure process has been permitted by the exposure permission determining unit 216, or (2), since the SID2 is set at a point in time when the recapturing process or the main exposure process is permitted, output of radiation 16a through 16c from the respective radiation sources 18a through 18c may be started automatically once permission has been granted.

Further, until the source-to-image distance (SID) reaches the SID2, the doctor 26 may be notified and prompted by the display unit 126 or the like to move the radiation output device 20, and may be notified and prompted to stop movement of the radiation output device 20 at a point in time that the SID2 is reached. As a result, in accordance with the notification content to stop movement, at a point in time that the doctor 26 stops moving the radiation output device 20 (i.e., when the acceleration detected by the acceleration sensor 217 is of a zero level), the exposure permission determining unit 216 can grant permission to initiate the recapturing process or the main exposure process, and thus capturing of images with respect to the subject 14 can be carried out immediately.

In the foregoing description of the thirteenth modification, a case has been explained in which recapturing of images or main exposure of radiation is carried out, however, it is a matter of course that the same effects and advantages can be obtained in a case where the thirteenth modification is applied to the case of the first image capturing process of the first embodiment, or the pre-exposure process of the second embodiment.

[Fourteenth Modification]

Incidentally, during image capturing with respect to the subject 14, because the center position of the image capturing region of the subject 14 substantially matches the center position of the imaging area 36, and further, since the image capturing region is positioned so as to fit within the imaging area 36, a large number of cases occur in which the region of interest (ROI) is positioned at the center of the imaging area 36. Owing thereto, cases are frequent in which, during actual image capturing, the dose of radiation 16b from the radiation source 18b in the center of the radiation output device 20 is large, whereas the doses of radiation 16a, 16c from both of the radiation sources 18a, 18c are set at smaller doses, of a degree sufficient to compensate the radiation 16b, and image capturing is carried out with respect to the subject 14.

Stated otherwise, during actual image capturing, the control processor 124 performs weighting on each of the radiation doses, such that the dose of radiation 16b from the radiation source 18b in the center of the radiation output device 20 is made maximum, whereas the doses of radiation 16a, 16c from both of the radiation sources 18a, 18c are set at smaller doses, of a degree sufficient to compensate the maximum radiation dose, and in accordance with such weighting, radiation 16a through 16c from each of the radiation sources 18a through 18c is applied simultaneously or sequentially.

In accordance with the aforementioned weighting, upon continued driving of the respective radiation sources 18a through 18c, only the center radiation source 18b is subject to degradation. Accordingly, from the standpoint of service life management of the radiation output device 20, it is desirable that dosage management is carried out, so that the cumulative doses (cumulative exposure doses) from each of the radiation sources 18a through 18c are respectively the same, and prolonged usage life of the radiation output device 20 including the respective radiation sources 18a through 18c can be realized.

Figure 35:
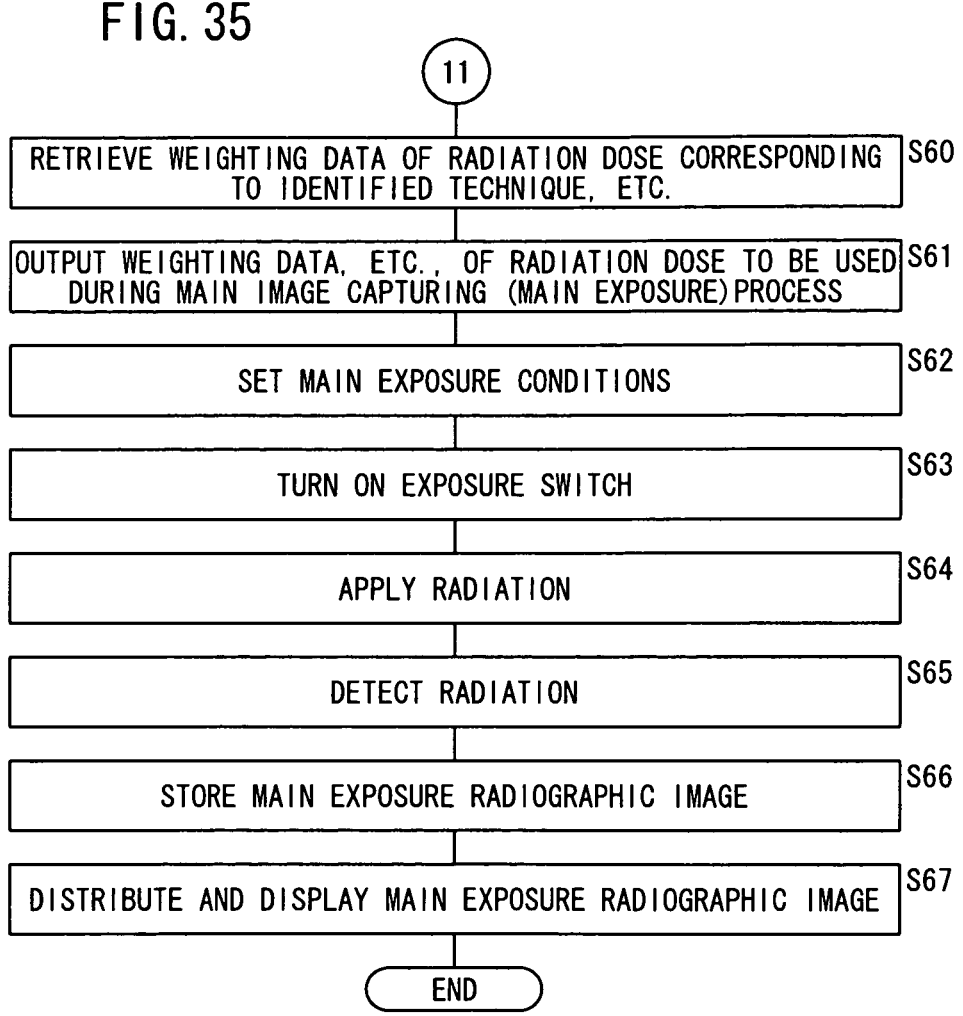
FIG. 35 is a flowchart of an operation sequence of the radiographic image capturing system according to the second embodiment.

Consequently, according to the fourteenth modification, for example, with the first embodiment, in step S13 and step S19 of FIG. 14, or with the second embodiment, in step S61 and step S67 of FIG. 35, data of the doses of radiation 16a through 16c (dose data on which weighting has been carried out) corresponding to optimal radiation dosage data retrieved by the database retriever 150 are stored in the database 134, and the stored data of the respective radiation doses may serve to assist radiation dosage management and management of service life.

As a result, concerning the cumulative exposure dose of radiation 16a through 16c, which is output from the respective radiation sources 18a through 18c, in the event that the cumulative exposure dose of the radiation 16b is more prominent than the cumulative exposure dose of the radiation 16a and 16c, there is a possibility that the radiation source 18b may degrade more rapidly than the radiation sources 18a and 18c. Consequently, based on comparing each of the cumulative exposure doses, weighting of the respective radiation doses is changed, such that the doses of radiation 16a, 16c output from each of the radiation sources 18a, 18c at both ends are made maximum with respect to capturing of images having a large SID, whereas the dose of radiation 16b output from the central radiation source 18b is of a smaller dose, of a degree for compensating the aforementioned maximum dose.

In this manner, as a material for determining the respective cumulative exposure doses, by changing the weighting of the doses of radiation 16a through 16c output from each of the radiation sources 18a through 18c, degradation of only the radiation source 18b can be avoided, and prolonged usage life of the radiation output device 20 including the respective radiation sources 18a through 18c can be realized.

Although certain preferred embodiments of the present invention have been shown and described in detail, it should be understood that various changes and modifications may be made to the embodiments without departing from the scope of the invention as set forth in the appended claims.

What is claimed is:

1. A radiographic image capturing system comprising:
    a radiation output device housing therein at least two radiation sources capable of emitting radiation with respect to a subject,
    a radiation detecting device for detecting radiation that has passed through the subject and converting the detected radiation into a radiographic image, and
    a control device for controlling the radiation output device and the radiation detecting device, wherein:
    in a case that a first image capturing process is carried out, in which radiation is applied to the subject from at least one radiation source from among the at least two radiation sources, the radiation detecting device detects radiation that has passed through the subject, thereby acquiring a first radiographic image by the first image capturing process; and
    the control device carries out weighting on doses of radiation to be emitted from the at least two radiation sources based on the first radiographic image, and controls the radiation output device to carry out a second image capturing process, in which the respective radiation is applied to the subject from the at least two radiation sources, in accordance with the weighting,
    wherein the control device carries out weighting on the doses of radiation to be emitted from the at least two radiation sources so as to supplement an insufficiency in the doses of radiation, in a case that the dose of radiation by the first image capturing process shown in the first radiographic image does not reach an optimum dose with respect to the subject.

2. The radiographic image capturing system according to claim 1, wherein the control device comprises an addition processor for producing a radiographic image for use in image interpretation of the subject, by adding together digital data of the first radiographic image and digital data of a second radiographic image in a case that the radiation detecting device has acquired the second radiographic image.

3. The radiographic image capturing system according to claim 2, wherein the radiation detecting device comprises:
    a radiation detector for acquiring the radiographic image by converting the radiation into visible light and then converting the converted visible light into electric signals, or by directly converting the radiation into electric signals; and
    a detector controller for controlling the radiation detector, wherein a plurality of solid-state detecting elements for converting the visible light or the radiation into the electric signals are arranged in a matrix in the radiation detector, and
    wherein the detector controller acquires the radiographic image by reading out the electrical signals respectively from the solid-state detecting elements.

4. The radiographic image capturing system according to claim 2, wherein the control device comprises:
    a database storing optimum radiation dose data indicative of optimum radiation doses corresponding respectively to a plurality of regions to be imaged and respective thicknesses of the regions to be imaged, and weighting data for weighting of the doses of radiation to be emitted from the respective radiation sources;
    a database retriever for, after a region to be imaged of the subject shown in the first radiographic image has been identified, retrieving optimum radiation dose data for a region to be imaged and a thickness which match the identified region to be imaged and the thickness of the identified region to be imaged, and weighting data for the region to be imaged which matches the identified region to be imaged, from the database;

an image capturing condition setting unit for setting second image capturing conditions for irradiating the region to be imaged with the radiation in the second image capturing process, based on the insufficiency in the doses of radiation, the region to be imaged of the subject and the thickness of the region to be imaged, and the optimum radiation dose data and the weighting data retrieved by the database retriever, in a case that the dose of radiation during the first image capturing process does not reach the optimum radiation dose indicated by the optimum radiation dose data retrieved by the database retriever; and a control processor for controlling the radiation output device and the radiation detecting device according to the second image capturing conditions.

5. The radiographic image capturing system according to claim 1, wherein, in a case that the radiation output device houses therein three radiation sources, the control device carries out, based on the first radiographic image, weighting on the doses of radiation to be emitted from the three radiation sources, such that the dose of the radiation emitted from a central one of the radiation sources is of a maximum dose level, and the doses of radiation emitted from the radiation sources at opposite ends are of a lower dose level, or such that the doses of radiation emitted from the radiation sources at opposite ends are of a maximum dose level, and the dose of the radiation emitted from the central one of the radiation sources is of a lower dose level.

6. The radiographic image capturing system according to claim 5, wherein in a case that the region to be imaged of the subject shown in the first radiographic image represents a hand, the control device carries out weighting on the doses of the radiation to be emitted from the three radiation sources, such that the dose of the radiation emitted from the central one of the radiation sources is of the maximum dose level, and the doses of the radiation emitted from the radiation sources at the opposite ends are of the lower dose level, and in a case that the region to be imaged of the subject shown in the first radiographic image represents a chest, the control device carries out weighting on the doses of the radiation to be emitted from the three radiation sources, such that the doses of the radiation emitted from the radiation sources at the opposite ends are of the maximum dose level and the dose of the radiation emitted from the central one of the radiation sources is of the lower dose level.

7. The radiographic image capturing system according to claim 1, wherein the radiation output device simultaneously or sequentially applies the radiation from the at least two radiation sources to the subject.

8. The radiographic image capturing system according to claim 1, wherein:
the radiation output device and the radiation detecting device comprise portable devices; and
the control device comprises a portable terminal or a console installed in a medical organization.

9. The radiographic image capturing system according to claim 1, wherein:
the radiation output device includes a grip on a side thereof opposite from a side on which the radiation is emitted;
the grip incorporates therein a gripped state sensor for outputting a detection signal indicating that the grip is gripped; and
the radiation output device permits the at least two radiation sources to emit radiation if the gripped state sensor outputs the detection signal.

10. The radiographic image capturing system according to claim 1, further comprising a body motion detector for detecting body motion of the subject which has been positioned with respect to the radiation detecting device,
wherein the control device includes an exposure permission determining unit for determining whether radiographic image capturing with respect to the subject is permitted or interrupted, based on the detection result of the body motion detector.

11. A radiographic image capturing method comprising the steps of:
in a case that at least two radiation sources are housed in a radiation output device, performing a first image capturing process, in which radiation is applied to a subject from at least one radiation source from among the at least two radiation sources;
acquiring a first radiographic image by the first image capturing process, by detecting, with a radiation detecting device, radiation that has passed through the subject;
carrying out weighting on respective doses of radiation to be emitted from the at least two radiation sources based on the first radiographic image;
in accordance with the weighting, carrying out a second image capturing process, in which the respective radiation is applied to the subject from the at least two radiation sources;
acquiring a second radiographic image by the second image capturing process, by detecting, with the radiation detecting device, the respective radiation that has passed through the subject; and
carrying out weighting on respective doses of radiation to be emitted from the at least two radiation sources so as to supplement an insufficiency in the doses of radiation, in a case that the dose of radiation by the first image capturing process shown in the first radiographic image does not reach an optimum dose with respect to the subject.

* * * * *